United States Patent
Aifantis et al.

(10) Patent No.: US 10,206,930 B2
(45) Date of Patent: Feb. 19, 2019

(54) METHODS FOR TREATING T-CELL ACUTE LYMPHOBLASTIC LEUKEMIA

(71) Applicant: New York University, New York, NY (US)

(72) Inventors: Iannis Aifantis, Brooklyn, NY (US); Panagiotis Ntziachristos, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/237,049

(22) Filed: Aug. 15, 2016

(65) Prior Publication Data

US 2017/0042904 A1 Feb. 16, 2017

Related U.S. Application Data

(60) Provisional application No. 62/205,407, filed on Aug. 14, 2015.

(51) Int. Cl.
| | |
|---|---|
| *C12N 15/11* | (2006.01) |
| *A61K 31/55* | (2006.01) |
| *C12N 15/113* | (2010.01) |
| *A61K 45/06* | (2006.01) |
| *A61K 31/713* | (2006.01) |

(52) U.S. Cl.
CPC ............ *A61K 31/55* (2013.01); *A61K 31/713* (2013.01); *A61K 45/06* (2013.01); *C12N 15/1137* (2013.01); *C12Y 114/11* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| 2012/0202843 A1* | 8/2012 | Munger | C12Q 1/6886 514/293 |
| 2014/0121201 A1* | 5/2014 | Littman | G01N 33/505 514/217.01 |

FOREIGN PATENT DOCUMENTS

| WO | 2012052390 A1 | 4/2012 | |
| WO | 2013143597 A1 | 10/2013 | |
| WO | WO-2014053491 A1 * | 4/2014 | ........... A61K 31/444 |

OTHER PUBLICATIONS

Agger et al, UTX and JMJD3 are histone H3K27 demethylases involved in HOX gene regulation and development, 2007, Nature, vol. 449: 731-735.*
Agger et al., "The H3K27me3 Demethylase JMJD3 Contributes to the Activation of the INK4A-ARF Locus in Response to Oncogene- and Stress-induced Senescence," Genes & Development 23:1171-1176 (2009).
Barradas et al., "Histone Demethylase JMJD3 Contributes to Epigenetic Control of INK4a/ARF by Oncogenic RAS," Genes & Development 23:1177-1182 (2009).
Ntziachristos et al., "Mechanisms of Epigenetic Regulation of Leukemia Onset and Progression," Adv. Immunol. 117:1-38 (2013).
Ntziachristos et al., "Contrasting Roles for Histone 3 Lysine 27 Demethylases in Acute Lymphoblastic Leukemia," Nature 514:513-517 (2014).
Ntziachristos et al., "Genetic Inactivation of the PRC2 Complex in T-cell Acute Lymphoblastic Leukemia," Nat. Med. 18(2):298-301 (2012).
Kruidenier et al., "A Selective Jumonji H3K27 Demethylase Inhibitor Modulates the Proinflammatory Macrophage Response," Nature 488:404-408 (2012).

* cited by examiner

*Primary Examiner* — Ekaterina Poliakova-Georgantas
(74) *Attorney, Agent, or Firm* — LeClairRyan PLLC

(57) ABSTRACT

The present invention is directed to methods of treating T-ALL that involve administering an inhibitor of jumonji D3 (JMJD3) demethylase. Another embodiment of the invention relates to methods inhibiting T-ALL cell proliferation and/or survival that involves administering an inhibitor of jumonji D3 (JMJD3) demethylase to a population of T-ALL cells.

14 Claims, 55 Drawing Sheets

Specification includes a Sequence Listing.

SEQUENCE LISTING

<160> NUMBER OF SEQ ID NOS: 61

<210> SEQ ID NO 1
<211> LENGTH: 6704
<212> TYPE: DNA
<213> ORGANISM: Homo sapiens

<400> SEQUENCE: 1

```
ggcaacatgc cagccccgta gcactgccca ccccacccac tgtggtctgt tgtacccac      60 tgctggggtg gtggttccaa tgagacaggg cacaccaaac tccatctggc tgttactgag    120
gcggagacac gggtgatgat tggctttctg gggagagagg aagtcctgtg attggccaga    180
tctctggagc ttgccgacgc ggtgtgagga cgctcccacg gaggccggaa ttggctgtga    240
aaggactgag gcagccatct gggggtagcg ggcactctta tcagagcggc tggagccgga    300
ccatcgtccc agagagctgg ggcaggggc cgtgcccaat ctccagggct cctggggcca    360
ctgctgacct ggctggatgc atcgggcagt ggaccctcca ggggcccgcg ctgcacggga    420
agcctttgcc cttggggggcc tgagctgtgc tggggcctgg agctcctgcc cgcctcatcc    480
ccctcctcgt agcgcatggc tgcctggagg cagatgctca gccagcattg ggcagccccc    540
gcttcctgct cccctacccc cttcacatgg cagtagttct gggcacccca gcaaaccata    600
ttatgctcca ggggcgccca ctccaagacc cctccatggg aagctggaat ccctgcatgg    660
ctgtgtgcag gcattgctcc gggagccagc ccagccaggg ctttgggaac agcttgggca    720
actgtacgag tcagagcacg atagtgagga ggccacacgc tgctaccaca gcgcccttcg    780
atacggagga agcttcgctg agctggggcc ccgcattggc cgactgcagc aggcccagct    840
ctggaacttt catactggct cctgccagca ccgagccaag gtcctgcccc cactggagca    900
agtgtggaac ttgctacacc ttgagcacaa acggaactat ggagccaagc ggggaggtcc    960
cccggtgaag cgagctgctg aacccccagt ggtgcagcct gtgcctcctg cagcactctc   1020
aggcccctca ggggaggagg gcctcagccc tggaggcaag cgaaggagag gctgcaactc   1080
```

```
tgaacagact ggccttcccc cagggctgcc actgcctcca ccaccattac caccaccacc   1140
accaccacca ccaccaccac caccaccccct gcctggcctg gctaccagcc cccatttca   1200 gctaaccaag ccagggctgt ggagtaccct gcatggagat gcctggggcc cagagcgcaa   1260
gggttcagca cccccagagc gccaggagca gcggcactcg ctgcctcacc catatccata   1320
cccagctcca gcgtacaccg cgcaccccccc tggccaccgg ctggtcccgg ctgctccccc   1380
aggcccaggc ccccgccccc caggagcaga gagccatggc tgcctgcctg ccacccgtcc   1440
ccccggaagt gaccttagag agagcagagt tcagaggtcg cggatggact ccagcgtttc   1500
accagcagca accaccgcct gcgtgcctta cgcccctccc cggccccctg gcctccccgg   1560
caccaccacc agcagcagca gtagcagcag cagcaacact ggtctccggg gcgtggagcc   1620
gaacccaggc attcccggcg ctgaccatta ccaaactccc gcgctggagg tctctcacca   1680
tggccgcctg ggccctcgg cacacagcag tcggaaaccg ttcttggggg ctcccgctgc   1740
cactccccac ctatccctgc cacctggacc ttcctcaccc cctccacccc cctgtccccg   1800
cctcttacgc cccccaccac cccctgcctg gttgaagggt ccggcctgcc gggcagcccg   1860
agaggatgga gagatcttag aagagctctt ctttgggact gagggacccc ccgcctgc   1920 cccaccaccc ctccccatc gcgagggctt cttggggct ccggcctccc gcttttctgt   1980
gggcactcag gattctcaca cccctcccac tccccaacc ccaaccacca gcagtagcaa   2040
cagcaacagt ggcagccaca gcagcagccc tgctgggcct gtgtcctttc ccaccaccc   2100 ctatctggcc agaagtatag accccttcc ccggcctccc agcccagcac agaaccccca   2160
ggacccacct cttgtacccc tgactcttgc cctgcctcca gccctccttt cctcctgcca   2220
ccaaaatacc tcaggaagct tcaggcgccc ggagagcccc cggcccaggg tctccttccc   2280
aaagaccccc gaggtggggc cggggccacc cccaggcccc ctgagtaaag ccccccagcc   2340
tgtgccgccc ggggttgggg agctgcctgc ccgaggccct cgactctttg attttccccc   2400
cactccgctg gaggaccagt ttgaggagcc agccgaattc aagatcctac ctgatgggct   2460
ggccaacatc atgaagatgc tggacgaatc cattcgcaag gaagaggaac agcaacaaca   2520
cgaagcaggc gtggcccccc aaccccccgct gaaggagccc tttgcatctc tgcagtctcc   2580
tttccccacc gacacagccc ccaccactac tgctcctgct gtcgccgtca ccaccaccac   2640
caccaccacc accaccacca cggccaccca ggaagaggag aagaagccac caccagccct   2700
accaccacca ccgcctctag ccaagttccc tccaccctct cagccacagc caccaccacc   2760 ccacccccc agcccggcca gcctgctcaa atccttggcc tccgtgctgg agggacaaaa   2820
gtactgttat cggggggactg gagcagctgt ttccacccgg cctgggccct tgcccaccac   2880
tcagtattcc cctggccccc catcaggtgc taccgccctg ccgcccacct cagcggcccc   2940
tagcgcccag ggctccccac agccctctgc ttcctcgtca tctcagttct ctacctcagg   3000
cgggccctgg gccgggagc gcagggcggg cgaagagcca gtcccgggcc ccatgacccc   3060
cacccaaccg ccccccacccc tatctctgcc ccctgctcgc tctgagtctg aggtgctaga   3120
agagatcagc cgggcttgcg agaccttgt ggagcgggtg ggccggagtg ccactgaccc   3180
agccgaccca gtggacacag cagagccagc ggacagtggg actgagcgac tgctgccccc   3240
cgcacaggcc aaggaggagg ctggcggggt ggcggcagtg tcaggcagct gtaagcggcg   3300
acagaaggag catcagaagg agcatcggcg gcacaggcgg gcctgtaagg acagtgtggg   3360
tcgtcggccc cgtgagggca gggcaaaggc caaggccaag gtcccaaag aaaagagccc   3420 ccgggtgctg gggaacctgg acctgcagag cgaggagatc cagggtcgtg agaagtcccg   3480
```

```
gcccgatctt ggcggggcct ccaaggccaa gccacccaca gctccagccc ctccatcagc   3540
tcctgcacct tctgcccagc ccacaccccc gtcagcctct gtccctggaa agaaggctcg   3600
ggaggaagcc ccagggccac cgggtgtcag ccgggccgac atgctgaagc tgcgctcact   3660
tagtgagggg ccccccaagg agctgaagat ccggctcatc aaggtagaga gtggtgacaa   3720
ggagaccttt atcgcctctg aggtggaaga gcggcggctg cgcatggcag acctcaccat   3780
cagccactgt gctgctgacg tcgtgcgcgc cagcaggaat gccaaggtga agggaagtt   3840 tcgagagtcc tacctttccc ctgcccagtc tgtgaaaccg aagatcaaca ctgaggagaa   3900
gctgccccgg gaaaaactca accccctac acccagcatc tatctggaga caaacggga    3960 tgccttctca cctgtcctgc tgcagttctg tacagaccct cgaaatccca tcacagtgat   4020
ccggggcctg gcgggctccc tgcggctcaa cttgggcctc ttctccacca agaccctggt   4080
ggaagcgagt ggcgaacaca ccgtggaagt tcgcacccag gtgcagcagc cctcagatga   4140
gaactgggat ctgacaggca ctcggcagat ctggccttgt gagagctccc gttcccacac   4200
caccattgcc aagtacgcac agtaccaggc ctcatccttc caggagtctc tgcaggagga   4260
gaaggagagt gaggatgagg agtcagagga gccagacagc accactggaa cccctcctag   4320
cagcgcacca gacccgaaga accatcacat catcaagttt ggcaccaaca tcgacttgtc   4380
tgatgctaag cggtggaagc cccagctgca ggagctgctg aagctgcccg ccttcatgcg   4440
ggtaacatcc acgggcaaca tgctgagcca cgtgggccac accatcctgg gcatgaacac   4500
ggtgcagctg tacatgaagg tgcccggcag ccgaacgcca ggccaccagg agaataacaa   4560
cttctgctcc gtcaacatca acattggccc aggcgactgc gagtggttcg cggtgcacga   4620
gcactactgg gagaccatca gcgctttctg tgatcggcac ggcgtggact acttgacggg   4680
ttcctggtgg ccaatcctgg atgatctcta tgcatccaat attcctgtgt accgcttcgt   4740
gcagcgaccc ggagacctcg tgtggattaa tgcggggact gtgcactggg tgcaggccac   4800
cggctggtgc aacaacattg cctggaacgt ggggcccctc accgcctatc agtaccagct   4860
ggccctggaa cgatacgagt ggaatgaggt gaagaacgtc aaatccatcg tgcccatgat   4920
tcacgtgtca tggaacgtgg ctcgcacggt caaaatcagc gaccccgact tgttcaagat   4980
gatcaagttc tgcctgctgc agtccatgaa gcactgccag gtgcaacgcg agagcctggt   5040
gcgggcaggg aagaaaatcg cttaccaggg ccgtgtcaag gacgagccag cctactactg   5100
caacgagtgc gatgtggagg tgtttaacat cctgttcgtg acaagtgaga atggcagccg   5160 caaacgtac ctggtacact gcgagggctg tgcccggcgc cgcagcgcag gcctgcaggg   5220
cgtggtggtg ctggagcagt accgcactga ggagctggct caggcctacg acgccttcac   5280
gctggtgagg gccggcgggc gcgcgggca gcggaggagg gcactggggc aggctgcagg   5340
gacgggcttc gggagcccgg ccgcgccttt ccctgagccc ccgccggctt tctcccccca   5400
ggccccagcc agcacgtcgc gatgaggccg gacgccccgc ccgcctgcct gcccgcgcaa   5460
ggcgccgcgg ggccaccagc acatgcctgg gctggaccta ggtccgcct gtggccgaga   5520 agggggtcgg gcccagccct tccacccccat tggcagctcc cctcacttaa tttattaaga   5580 aaaactttt ttttttttt agcaaatatg aggaaaaag gaaaaaaat gggagacggg   5640 ggagggggct ggcagcccct cgcccaccag cgcctcccct caccgacttt ggccttttta   5700
gcaacagaca caaggaccag gctccggcgg cggcggggt cacatacggg ttccctcacc   5760
ctgccagccg cccgccccgcc cggcgcagat gcacgcggct cgtgtatgta catagacgtt   5820
```

-continued

```
acggcagccg aggtttttaa tgagattctt tctatgggct ttacccctcc cccggaacct    5880
ccttttttac ttccaatgct agctgtgacc cctgtacatg tctctttatt cacttggtta    5940
tgatttgtat tttttgttct tttcttgttt ttttgttttt aatttataac agtcccactc    6000
acctctattt attcattttt gggaaaaccc gacctcccac accccaagc catcctgccc     6060 gcccctccag ggaccgcccg tcgccgggct ctcccgcgc cccagtgtgt gtccgggccc     6120
ggcccgaccg tctccacccg tccgcccgcg gctccagccg ggttctcatg gtgctcaaac    6180
ccgctcccct ccctacgtc ctgcactttc tcggaccagt cccccactc ccgacccgac      6240 cccagcccca cctgagggtg agcaactcct gtactgtagg ggaagaagtg ggaactgaaa    6300
tggtattttg taaaaaaaat aaataaaata aaaaattaa aggttttaaa gaaagaacta     6360
tgaggaaaag gaaccccgtc cttcccagcc ccggccaact ttaaaaaaca cagaccttca    6420
cccccacccc cttttctttt taagtgtgaa acaacccagg gccagggcct cactggggca    6480
gggacacccc ggggtgagtt tctctggggc tttattttcg ttttgttggt tgttttttct    6540
ccacgctggg gctgcggagg ggtgggggt ttacagtccc gcaccctcgc actgcactgt     6600
ctctctgccc caggggcaga ggggtcttcc caaccctacc cctattttcg gtgattttg     6660 tgtgagaata ttaatattaa aaataaacgg agaaaaaaaa tcct                    6704
```

<210> SEQ ID NO 2
<211> LENGTH: 1682
<212> TYPE: PRT
<213> ORGANISM: Homo sapiens

<400> SEQUENCE: 2

```
Met His Arg Ala Val Asp Pro Pro Gly Ala Arg Ala Ala Arg Glu Ala
1               5                   10                  15

Phe Ala Leu Gly Gly Leu Ser Cys Ala Gly Ala Trp Ser Ser Cys Pro
            20                  25                  30

Pro His Pro Pro Pro Arg Ser Ala Trp Leu Pro Gly Gly Arg Cys Ser
        35                  40                  45

Ala Ser Ile Gly Gln Pro Pro Leu Pro Ala Pro Leu Pro Pro Ser His
    50                  55                  60

Gly Ser Ser Ser Gly His Pro Ser Lys Pro Tyr Tyr Ala Pro Gly Ala
65                  70                  75                  80

Pro Thr Pro Arg Pro Leu His Gly Lys Leu Glu Ser Leu His Gly Cys
                85                  90                  95

Val Gln Ala Leu Leu Arg Glu Pro Ala Gln Pro Gly Leu Trp Glu Gln
            100                 105                 110

Leu Gly Gln Leu Tyr Glu Ser Glu His Asp Ser Glu Glu Ala Thr Arg
        115                 120                 125

Cys Tyr His Ser Ala Leu Arg Tyr Gly Gly Ser Phe Ala Glu Leu Gly
    130                 135                 140

Pro Arg Ile Gly Arg Leu Gln Gln Ala Gln Leu Trp Asn Phe His Thr
145                 150                 155                 160

Gly Ser Cys Gln His Arg Ala Lys Val Leu Pro Leu Glu Gln Val
                165                 170                 175

Trp Asn Leu Leu His Leu Glu His Lys Arg Asn Tyr Gly Ala Lys Arg
            180                 185                 190

Gly Gly Pro Pro Val Lys Arg Ala Ala Glu Pro Val Val Gln Pro
        195                 200                 205

Val Pro Pro Ala Ala Leu Ser Gly Pro Ser Gly Glu Glu Gly Leu Ser
    210                 215                 220
```

```
Pro Gly Gly Lys Arg Arg Gly Cys Asn Ser Glu Gln Thr Gly Leu
225                 230                 235                 240

Pro Pro Gly Leu Pro Leu Pro Pro Pro Leu Pro Pro Pro Pro Pro
            245                 250                 255

Pro Pro Pro Pro Pro Pro Pro Leu Pro Gly Leu Ala Thr Ser Pro
        260                 265                 270

Pro Phe Gln Leu Thr Lys Pro Gly Leu Trp Ser Thr Leu His Gly Asp
    275                 280                 285

Ala Trp Gly Pro Glu Arg Lys Gly Ser Ala Pro Pro Glu Arg Gln Glu
    290                 295                 300

Gln Arg His Ser Leu Pro His Pro Tyr Pro Tyr Pro Ala Pro Ala Tyr
305                 310                 315                 320

Thr Ala His Pro Pro Gly His Arg Leu Val Pro Ala Ala Pro Pro Gly
                325                 330                 335

Pro Gly Pro Arg Pro Pro Gly Ala Glu Ser His Gly Cys Leu Pro Ala
            340                 345                 350

Thr Arg Pro Pro Gly Ser Asp Leu Arg Glu Ser Arg Val Gln Arg Ser
        355                 360                 365

Arg Met Asp Ser Ser Val Ser Pro Ala Ala Thr Thr Ala Cys Val Pro
    370                 375                 380

Tyr Ala Pro Ser Arg Pro Pro Gly Leu Pro Gly Thr Thr Thr Ser Ser
385                 390                 395                 400

Ser Ser Ser Ser Ser Asn Thr Gly Leu Arg Gly Val Glu Pro Asn
                405                 410                 415

Pro Gly Ile Pro Gly Ala Asp His Tyr Gln Thr Pro Ala Leu Glu Val
            420                 425                 430

Ser His His Gly Arg Leu Gly Pro Ser Ala His Ser Ser Arg Lys Pro
        435                 440                 445

Phe Leu Gly Ala Pro Ala Ala Thr Pro His Leu Ser Leu Pro Pro Gly
450                 455                 460

Pro Ser Ser Pro Pro Pro Pro Cys Pro Arg Leu Leu Arg Pro Pro
465                 470                 475                 480

Pro Pro Pro Ala Trp Leu Lys Gly Pro Ala Cys Arg Ala Ala Arg Glu
            485                 490                 495

Asp Gly Glu Ile Leu Glu Glu Leu Phe Phe Gly Thr Glu Gly Pro Pro
        500                 505                 510

Arg Pro Ala Pro Pro Leu Pro His Arg Glu Gly Phe Leu Gly Pro
    515                 520                 525

Pro Ala Ser Arg Phe Ser Val Gly Thr Gln Asp Ser His Thr Pro Pro
    530                 535                 540

Thr Pro Pro Thr Pro Thr Thr Ser Ser Asn Ser Asn Ser Gly Ser
545                 550                 555                 560

His Ser Ser Ser Pro Ala Gly Pro Val Ser Phe Pro Pro Pro Tyr
                565                 570                 575

Leu Ala Arg Ser Ile Asp Pro Leu Pro Arg Pro Pro Ser Pro Ala Gln
            580                 585                 590

Asn Pro Gln Asp Pro Pro Leu Val Pro Leu Thr Leu Ala Leu Pro Pro
        595                 600                 605

Ala Pro Pro Ser Ser Cys His Gln Asn Thr Ser Gly Ser Phe Arg Arg
        610                 615                 620

Pro Glu Ser Pro Arg Pro Arg Val Ser Phe Pro Lys Thr Pro Glu Val
625                 630                 635                 640
```

```
Gly Pro Gly Pro Pro Pro Gly Pro Leu Ser Lys Ala Pro Gln Pro Val
                645                 650                 655

Pro Pro Gly Val Gly Glu Leu Pro Ala Arg Gly Pro Arg Leu Phe Asp
            660                 665                 670

Phe Pro Pro Thr Pro Leu Glu Asp Gln Phe Glu Glu Pro Ala Glu Phe
        675                 680                 685

Lys Ile Leu Pro Asp Gly Leu Ala Asn Ile Met Lys Met Leu Asp Glu
    690                 695                 700

Ser Ile Arg Lys Glu Glu Gln Gln Gln His Glu Ala Gly Val Ala
705                 710                 715                 720

Pro Gln Pro Pro Leu Lys Glu Pro Phe Ala Ser Leu Gln Ser Pro Phe
                725                 730                 735

Pro Thr Asp Thr Ala Pro Thr Thr Ala Pro Ala Val Ala Val Thr
            740                 745                 750

Thr Thr Thr Thr Thr Thr Thr Thr Thr Ala Thr Gln Glu Glu Glu
        755                 760                 765

Lys Lys Pro Pro Pro Ala Leu Pro Pro Pro Pro Leu Ala Lys Phe
    770                 775                 780

Pro Pro Pro Ser Gln Pro Gln Pro Pro Pro Pro Pro Pro Ser Pro
785                 790                 795                 800

Ala Ser Leu Leu Lys Ser Leu Ala Ser Val Leu Glu Gly Gln Lys Tyr
                805                 810                 815

Cys Tyr Arg Gly Thr Gly Ala Ala Val Ser Thr Arg Pro Gly Pro Leu
            820                 825                 830

Pro Thr Thr Gln Tyr Ser Pro Gly Pro Pro Ser Gly Ala Thr Ala Leu
        835                 840                 845

Pro Pro Thr Ser Ala Ala Pro Ser Ala Gln Gly Ser Pro Gln Pro Ser
    850                 855                 860

Ala Ser Ser Ser Gln Phe Ser Thr Ser Gly Gly Pro Trp Ala Arg
865                 870                 875                 880

Glu Arg Arg Ala Gly Glu Glu Pro Val Pro Gly Pro Met Thr Pro Thr
                885                 890                 895

Gln Pro Pro Pro Pro Leu Ser Leu Pro Pro Ala Arg Ser Glu Ser Glu
            900                 905                 910

Val Leu Glu Glu Ile Ser Arg Ala Cys Glu Thr Leu Val Glu Arg Val
        915                 920                 925

Gly Arg Ser Ala Thr Asp Pro Ala Asp Pro Val Asp Thr Ala Glu Pro
    930                 935                 940

Ala Asp Ser Gly Thr Glu Arg Leu Leu Pro Pro Ala Gln Ala Lys Glu
945                 950                 955                 960

Glu Ala Gly Gly Val Ala Ala Val Ser Gly Ser Cys Lys Arg Arg Gln
                965                 970                 975

Lys Glu His Gln Lys Glu His Arg Arg His Arg Arg Ala Cys Lys Asp
            980                 985                 990

Ser Val Gly Arg Arg Pro Arg Glu Gly Arg Ala Lys Ala Lys Ala Lys
        995                 1000                1005

Val Pro Lys Glu Lys Ser Arg Arg Val Leu Gly Asn Leu Asp Leu
    1010                1015                1020

Gln Ser Glu Glu Ile Gln Gly Arg Glu Lys Ser Arg Pro Asp Leu
    1025                1030                1035

Gly Gly Ala Ser Lys Ala Lys Pro Pro Thr Ala Pro Ala Pro Pro
    1040                1045                1050

Ser Ala Pro Ala Pro Ser Ala Gln Pro Thr Pro Pro Ser Ala Ser
```

1055                1060                1065
Val Pro Gly Lys Lys Ala Arg Glu Glu Ala Pro Gly Pro Pro Gly
        1070                1075                1080

Val Ser Arg Ala Asp Met Leu Lys Leu Arg Ser Leu Ser Glu Gly
        1085                1090                1095

Pro Pro Lys Glu Leu Lys Ile Arg Leu Ile Lys Val Glu Ser Gly
        1100                1105                1110

Asp Lys Glu Thr Phe Ile Ala Ser Glu Val Glu Arg Arg Leu
        1115                1120                1125

Arg Met Ala Asp Leu Thr Ile Ser His Cys Ala Ala Asp Val Val
        1130                1135                1140

Arg Ala Ser Arg Asn Ala Lys Val Lys Gly Lys Phe Arg Glu Ser
        1145                1150                1155

Tyr Leu Ser Pro Ala Gln Ser Val Lys Pro Lys Ile Asn Thr Glu
        1160                1165                1170

Glu Lys Leu Pro Arg Glu Lys Leu Asn Pro Pro Thr Pro Ser Ile
        1175                1180                1185

Tyr Leu Glu Ser Lys Arg Asp Ala Phe Ser Pro Val Leu Leu Gln
        1190                1195                1200

Phe Cys Thr Asp Pro Arg Asn Pro Ile Thr Val Ile Arg Gly Leu
        1205                1210                1215

Ala Gly Ser Leu Arg Leu Asn Leu Gly Leu Phe Ser Thr Lys Thr
        1220                1225                1230

Leu Val Glu Ala Ser Gly Glu His Thr Val Glu Val Arg Thr Gln
        1235                1240                1245

Val Gln Gln Pro Ser Asp Glu Asn Trp Asp Leu Thr Gly Thr Arg
        1250                1255                1260

Gln Ile Trp Pro Cys Glu Ser Ser Arg Ser His Thr Thr Ile Ala
        1265                1270                1275

Lys Tyr Ala Gln Tyr Gln Ala Ser Ser Phe Gln Glu Ser Leu Gln
        1280                1285                1290

Glu Glu Lys Glu Ser Glu Asp Glu Glu Ser Glu Glu Pro Asp Ser
        1295                1300                1305

Thr Thr Gly Thr Pro Pro Ser Ser Ala Pro Asp Pro Lys Asn His
        1310                1315                1320

His Ile Ile Lys Phe Gly Thr Asn Ile Asp Leu Ser Asp Ala Lys
        1325                1330                1335

Arg Trp Lys Pro Gln Leu Gln Glu Leu Leu Lys Leu Pro Ala Phe
        1340                1345                1350

Met Arg Val Thr Ser Thr Gly Asn Met Leu Ser His Val Gly His
        1355                1360                1365

Thr Ile Leu Gly Met Asn Thr Val Gln Leu Tyr Met Lys Val Pro
        1370                1375                1380

Gly Ser Arg Thr Pro Gly His Gln Glu Asn Asn Asn Phe Cys Ser
        1385                1390                1395

Val Asn Ile Asn Ile Gly Pro Gly Asp Cys Glu Trp Phe Ala Val
        1400                1405                1410

His Glu His Tyr Trp Glu Thr Ile Ser Ala Phe Cys Asp Arg His
        1415                1420                1425

Gly Val Asp Tyr Leu Thr Gly Ser Trp Trp Pro Ile Leu Asp Asp
        1430                1435                1440

Leu Tyr Ala Ser Asn Ile Pro Val Tyr Arg Phe Val Gln Arg Pro
        1445                1450                1455

```
Gly Asp Leu Val Trp Ile Asn Ala Gly Thr Val His Trp Val Gln
    1460                1465                1470

Ala Thr Gly Trp Cys Asn Asn Ile Ala Trp Asn Val Gly Pro Leu
    1475                1480                1485

Thr Ala Tyr Gln Tyr Gln Leu Ala Leu Glu Arg Tyr Glu Trp Asn
    1490                1495                1500

Glu Val Lys Asn Val Lys Ser Ile Val Pro Met Ile His Val Ser
    1505                1510                1515

Trp Asn Val Ala Arg Thr Val Lys Ile Ser Asp Pro Asp Leu Phe
    1520                1525                1530

Lys Met Ile Lys Phe Cys Leu Leu Gln Ser Met Lys His Cys Gln
    1535                1540                1545

Val Gln Arg Glu Ser Leu Val Arg Ala Gly Lys Lys Ile Ala Tyr
    1550                1555                1560

Gln Gly Arg Val Lys Asp Glu Pro Ala Tyr Tyr Cys Asn Glu Cys
    1565                1570                1575

Asp Val Glu Val Phe Asn Ile Leu Phe Val Thr Ser Glu Asn Gly
    1580                1585                1590

Ser Arg Asn Thr Tyr Leu Val His Cys Glu Gly Cys Ala Arg Arg
    1595                1600                1605

Arg Ser Ala Gly Leu Gln Gly Val Val Val Leu Glu Gln Tyr Arg
    1610                1615                1620

Thr Glu Glu Leu Ala Gln Ala Tyr Asp Ala Phe Thr Leu Val Arg
    1625                1630                1635

Ala Arg Arg Ala Arg Gly Gln Arg Arg Ala Leu Gly Gln Ala
    1640                1645                1650

Ala Gly Thr Gly Phe Gly Ser Pro Ala Ala Pro Phe Pro Glu Pro
    1655                1660                1665

Pro Pro Ala Phe Ser Pro Gln Ala Pro Ala Ser Thr Ser Arg
    1670                1675                1680

<210> SEQ ID NO 3
<211> LENGTH: 63
<212> TYPE: DNA
<213> ORGANISM: Artificial Sequence
<220> FEATURE:
<223> OTHER INFORMATION: shJMJD3A shRNA

<400> SEQUENCE: 3
cagggaagtt tcgagaagtc ctatagtgaa gccacagatg tataggactc tcgaacttcc    60
ctt                                                                  63

<210> SEQ ID NO 4
<211> LENGTH: 63
<212> TYPE: DNA
<213> ORGANISM: Artificial Sequence
<220> FEATURE:
<223> OTHER INFORMATION: shJMJD3B shRNA

<400> SEQUENCE: 4
acaccagcag tagcaacagc aatagtgaag ccacagatgt attgctgttg ctactgctgg    60
tgg                                                                  63

<210> SEQ ID NO 5
<211> LENGTH: 63
<212> TYPE: DNA
<213> ORGANISM: Artificial Sequence
```

<220> FEATURE:
<223> OTHER INFORMATION: shUTX shRNA

<400> SEQUENCE: 5
acacaaggta gtctacagaa tatagtgaag ccacagatgt atattctgta gactaccttg    60
tgg                                                                   63

<210> SEQ ID NO 6
<211> LENGTH: 116
<212> TYPE: DNA
<213> ORGANISM: Artificial Sequence
<220> FEATURE:
<223> OTHER INFORMATION: shRenilla shRNA

<400> SEQUENCE: 6
ctcgagaagg tatattgctg ttgacagtga gcgcaggaat tataatgctt atctatagtg    60
aagccacaga tgtatagata agcattataa ttcctatgcc tactgcctcg gaattc      116

<210> SEQ ID NO 7
<211> LENGTH: 20
<212> TYPE: DNA
<213> ORGANISM: Artificial Sequence
<220> FEATURE:
<223> OTHER INFORMATION: Utx-F mouse cDNA primer

<400> SEQUENCE: 7
tccaagacca ccatcctcac                                                 20

<210> SEQ ID NO 8
<211> LENGTH: 20
<212> TYPE: DNA
<213> ORGANISM: Artificial Sequence
<220> FEATURE:
<223> OTHER INFORMATION: Utx-R mouse cDNA primer

<400> SEQUENCE: 8
ggaggaaaga aagcatcacg                                                 20

<210> SEQ ID NO 9
<211> LENGTH: 20
<212> TYPE: DNA
<213> ORGANISM: Artificial Sequence
<220> FEATURE:
<223> OTHER INFORMATION: Jmjd3-F mouse cDNA primer

<400> SEQUENCE: 9
acgagcctgc ctactactgc                                                 20

<210> SEQ ID NO 10
<211> LENGTH: 18
<212> TYPE: DNA
<213> ORGANISM: Artificial Sequence
<220> FEATURE:
<223> OTHER INFORMATION: Jmjd3-R mouse cDNA primer

<400> SEQUENCE: 10
ctcgcagtgc accaggta                                                   18

<210> SEQ ID NO 11
<211> LENGTH: 20
<212> TYPE: DNA
<213> ORGANISM: Artificial Sequence
<220> FEATURE:
<223> OTHER INFORMATION: Hes1-F mouse cDNA primer

<400> SEQUENCE: 11
gcgaagggca agaataaatg                                           20

<210> SEQ ID NO 12
<211> LENGTH: 21
<212> TYPE: DNA
<213> ORGANISM: Artificial Sequence
<220> FEATURE:
<223> OTHER INFORMATION: Hes1-R mouse cDNA primer

<400> SEQUENCE: 12
tgtctgcctt ctctagcttg g                                         21

<210> SEQ ID NO 13
<211> LENGTH: 22
<212> TYPE: DNA
<213> ORGANISM: Artificial Sequence
<220> FEATURE:
<223> OTHER INFORMATION: Il17ra-F mouse cDNA primer

<400> SEQUENCE: 13
catttcactc gtaaaagagc cc                                        22

<210> SEQ ID NO 14
<211> LENGTH: 20
<212> TYPE: DNA
<213> ORGANISM: Artificial Sequence
<220> FEATURE:
<223> OTHER INFORMATION: Il17ra-R mouse cDNA primer

<400> SEQUENCE: 14
tggaagtgga tggaagtcaa                                           20

<210> SEQ ID NO 15
<211> LENGTH: 22
<212> TYPE: DNA
<213> ORGANISM: Artificial Sequence
<220> FEATURE:
<223> OTHER INFORMATION: Suz12-F mouse cDNA primer

<400> SEQUENCE: 15
tgatggctta tcatttttgt gg                                        22

<210> SEQ ID NO 16
<211> LENGTH: 23
<212> TYPE: DNA
<213> ORGANISM: Artificial Sequence
<220> FEATURE:
<223> OTHER INFORMATION: Suz12-R mouse cDNA primer

<400> SEQUENCE: 16
gagaaaatga aaggagagca aga                                       23

<210> SEQ ID NO 17
<211> LENGTH: 20
<212> TYPE: DNA
<213> ORGANISM: Artificial Sequence
<220> FEATURE:
<223> OTHER INFORMATION: Hes1 promoter-F mouse ChIP primers

<400> SEQUENCE: 17
aagtttcaca cgagccgttc                                           20

<210> SEQ ID NO 18
<211> LENGTH: 20

-continued

<212> TYPE: DNA
<213> ORGANISM: Artificial Sequence
<220> FEATURE:
<223> OTHER INFORMATION: Hes1 promoter-R mouse ChIP primer

<400> SEQUENCE: 18
tgttatcagc accagctcca                                        20

<210> SEQ ID NO 19
<211> LENGTH: 20
<212> TYPE: DNA
<213> ORGANISM: Artificial Sequence
<220> FEATURE:
<223> OTHER INFORMATION: Jmjd3 promoter-F mouse ChIP primer

<400> SEQUENCE: 19
cgcagcttcc cagaagttag                                        20

<210> SEQ ID NO 20
<211> LENGTH: 20
<212> TYPE: DNA
<213> ORGANISM: Artificial Sequence
<220> FEATURE:
<223> OTHER INFORMATION: Jmjd3 promoter-R mouse ChIP primer

<400> SEQUENCE: 20
accaagttcc tccagctcct                                        20

<210> SEQ ID NO 21
<211> LENGTH: 20
<212> TYPE: DNA
<213> ORGANISM: Artificial Sequence
<220> FEATURE:
<223> OTHER INFORMATION: NRARP-F human cDNA primer

<400> SEQUENCE: 21
cgctgttgct ggtgttctaa                                        20

<210> SEQ ID NO 22
<211> LENGTH: 20
<212> TYPE: DNA
<213> ORGANISM: Artificial Sequence
<220> FEATURE:
<223> OTHER INFORMATION: NRARP-R human cDNA primer

<400> SEQUENCE: 22
cattgaccac gcagtgtttt                                        20

<210> SEQ ID NO 23
<211> LENGTH: 20
<212> TYPE: DNA
<213> ORGANISM: Artificial Sequence
<220> FEATURE:
<223> OTHER INFORMATION: NOTCH1-F human cDNA primer

<400> SEQUENCE: 23
cggggctaac aaagatatgc                                        20

<210> SEQ ID NO 24
<211> LENGTH: 19
<212> TYPE: DNA
<213> ORGANISM: Artificial Sequence
<220> FEATURE:
<223> OTHER INFORMATION: NOTCH1-R human cDNA primer

<400> SEQUENCE: 24
agtggtccag cagcaccctt                    19

<210> SEQ ID NO 25
<211> LENGTH: 20
<212> TYPE: DNA
<213> ORGANISM: Artificial Sequence
<220> FEATURE:
<223> OTHER INFORMATION: MYC-F human cDNA primer

<400> SEQUENCE: 25
gctgcttaga cgctggattt                    20

<210> SEQ ID NO 26
<211> LENGTH: 21
<212> TYPE: DNA
<213> ORGANISM: Artificial Sequence
<220> FEATURE:
<223> OTHER INFORMATION: MYC-R human cDNA primer

<400> SEQUENCE: 26
cgaggtcata gttcctgttg g                  21

<210> SEQ ID NO 27
<211> LENGTH: 20
<212> TYPE: DNA
<213> ORGANISM: Artificial Sequence
<220> FEATURE:
<223> OTHER INFORMATION: MAZ-F human cDNA primer

<400> SEQUENCE: 27
gaccacatga aggtgcacag                    20

<210> SEQ ID NO 28
<211> LENGTH: 18
<212> TYPE: DNA
<213> ORGANISM: Artificial Sequence
<220> FEATURE:
<223> OTHER INFORMATION: MAZ-R human cDNA primer

<400> SEQUENCE: 28
gtccttcacc gcgtggat                      18

<210> SEQ ID NO 29
<211> LENGTH: 20
<212> TYPE: DNA
<213> ORGANISM: Artificial Sequence
<220> FEATURE:
<223> OTHER INFORMATION: HEY1-F human cDNA primer

<400> SEQUENCE: 29
attttggcca gaaaaagacg                    20

<210> SEQ ID NO 30
<211> LENGTH: 20
<212> TYPE: DNA
<213> ORGANISM: Artificial Sequence
<220> FEATURE:
<223> OTHER INFORMATION: HEY1-R human cDNA primer

<400> SEQUENCE: 30
ctgggtacca gccttctcag                    20

<210> SEQ ID NO 31
<211> LENGTH: 21
<212> TYPE: DNA
<213> ORGANISM: Artificial Sequence

```
<220> FEATURE:
<223> OTHER INFORMATION: JMJD3-F human cDNA primer

<400> SEQUENCE: 31
gggaagaaaa tcgcttacca g                                             21

<210> SEQ ID NO 32
<211> LENGTH: 21
<212> TYPE: DNA
<213> ORGANISM: Artificial Sequence
<220> FEATURE:
<223> OTHER INFORMATION: JMJD3-R human cDNA primer

<400> SEQUENCE: 32
tcacttgtca cgaacaggat g                                             21

<210> SEQ ID NO 33
<211> LENGTH: 22
<212> TYPE: DNA
<213> ORGANISM: Artificial Sequence
<220> FEATURE:
<223> OTHER INFORMATION: UTX-F human cDNA primer

<400> SEQUENCE: 33
acttggaaaa ctttgtggtg ct                                            22

<210> SEQ ID NO 34
<211> LENGTH: 19
<212> TYPE: DNA
<213> ORGANISM: Artificial Sequence
<220> FEATURE:
<223> OTHER INFORMATION: UTX-R human cDNA primer

<400> SEQUENCE: 34
caagatgagg cggatggta                                                19

<210> SEQ ID NO 35
<211> LENGTH: 19
<212> TYPE: DNA
<213> ORGANISM: Artificial Sequence
<220> FEATURE:
<223> OTHER INFORMATION: NRARP locus-F human ChIP primer

<400> SEQUENCE: 35
accaactgcg agttcaacg                                                19

<210> SEQ ID NO 36
<211> LENGTH: 18
<212> TYPE: DNA
<213> ORGANISM: Artificial Sequence
<220> FEATURE:
<223> OTHER INFORMATION: NRARP locus-R human ChIP primer

<400> SEQUENCE: 36
ttgaccagca gcttcacg                                                 18

<210> SEQ ID NO 37
<211> LENGTH: 21
<212> TYPE: DNA
<213> ORGANISM: Artificial Sequence
<220> FEATURE:
<223> OTHER INFORMATION: NOTCH1 locus-1F human ChIP primer

<400> SEQUENCE: 37
cagacacttt gaagccctca g                                             21
```

```
<210> SEQ ID NO 38
<211> LENGTH: 20
<212> TYPE: DNA
<213> ORGANISM: Artificial Sequence
<220> FEATURE:
<223> OTHER INFORMATION: NOTCH1 locus-1R human ChIP primer

<400> SEQUENCE: 38
cgcctttgtg cttctgttct                                              20

<210> SEQ ID NO 39
<211> LENGTH: 19
<212> TYPE: DNA
<213> ORGANISM: Artificial Sequence
<220> FEATURE:
<223> OTHER INFORMATION: NOTCH1 locus-2F human ChIP primer

<400> SEQUENCE: 39
cctcctcttc ctcgctgtt                                               19

<210> SEQ ID NO 40
<211> LENGTH: 20
<212> TYPE: DNA
<213> ORGANISM: Artificial Sequence
<220> FEATURE:
<223> OTHER INFORMATION: NOTCH1 locus-2R human ChIP primer

<400> SEQUENCE: 40
cagactgagc acccgtctct                                              20

<210> SEQ ID NO 41
<211> LENGTH: 20
<212> TYPE: DNA
<213> ORGANISM: Artificial Sequence
<220> FEATURE:
<223> OTHER INFORMATION: NOTCH1 locus-3F human ChIP primer

<400> SEQUENCE: 41
aggctggcag ctctattcag                                              20

<210> SEQ ID NO 42
<211> LENGTH: 20
<212> TYPE: DNA
<213> ORGANISM: Artificial Sequence
<220> FEATURE:
<223> OTHER INFORMATION: NOTCH1 locus-3R human ChIP primer

<400> SEQUENCE: 42
cgtggcagag tctggaaagt                                              20

<210> SEQ ID NO 43
<211> LENGTH: 20
<212> TYPE: DNA
<213> ORGANISM: Artificial Sequence
<220> FEATURE:
<223> OTHER INFORMATION: MYC locus 1F human ChIP primer

<400> SEQUENCE: 43
ggtcggacat tcctgcttta                                              20

<210> SEQ ID NO 44
<211> LENGTH: 19
<212> TYPE: DNA
<213> ORGANISM: Artificial Sequence
<220> FEATURE:
<223> OTHER INFORMATION: MYC locus 1R human ChIP primer
```

<400> SEQUENCE: 44
caaggagctc aggatgcaa                                          19

<210> SEQ ID NO 45
<211> LENGTH: 20
<212> TYPE: DNA
<213> ORGANISM: Artificial Sequence
<220> FEATURE:
<223> OTHER INFORMATION: MAZ locus 1F human ChIP primer

<400> SEQUENCE: 45
gtctccctcc ctcctgtgtt                                         20

<210> SEQ ID NO 46
<211> LENGTH: 20
<212> TYPE: DNA
<213> ORGANISM: Artificial Sequence
<220> FEATURE:
<223> OTHER INFORMATION: MAZ locus 1R human ChIP primer

<400> SEQUENCE: 46
aaatttgaaa aggcggagtg                                         20

<210> SEQ ID NO 47
<211> LENGTH: 19
<212> TYPE: DNA
<213> ORGANISM: Artificial Sequence
<220> FEATURE:
<223> OTHER INFORMATION: MAZ locus 2F human ChIP primer

<400> SEQUENCE: 47
atcttcgggg aacgactca                                          19

<210> SEQ ID NO 48
<211> LENGTH: 18
<212> TYPE: DNA
<213> ORGANISM: Artificial Sequence
<220> FEATURE:
<223> OTHER INFORMATION: MAZ locus 2R human ChIP primer

<400> SEQUENCE: 48
cttcggcttc cgcttttt                                           18

<210> SEQ ID NO 49
<211> LENGTH: 20
<212> TYPE: DNA
<213> ORGANISM: Artificial Sequence
<220> FEATURE:
<223> OTHER INFORMATION: HEY1 locus-F human ChIP primer

<400> SEQUENCE: 49
tggggacatg gaacctagag                                         20

<210> SEQ ID NO 50
<211> LENGTH: 20
<212> TYPE: DNA
<213> ORGANISM: Artificial Sequence
<220> FEATURE:
<223> OTHER INFORMATION: HEY1 locus-R human ChIP primer

<400> SEQUENCE: 50
gcgacctctc agatcacctc                                         20

<210> SEQ ID NO 51

```
<211> LENGTH: 20
<212> TYPE: DNA
<213> ORGANISM: Artificial Sequence
<220> FEATURE:
<223> OTHER INFORMATION: RBBP6 locus-1F human ChIP primer

<400> SEQUENCE: 51
tatggtgctg gtggctgtta                                           20

<210> SEQ ID NO 52
<211> LENGTH: 21
<212> TYPE: DNA
<213> ORGANISM: Artificial Sequence
<220> FEATURE:
<223> OTHER INFORMATION: RBBP6 locus-1R human ChIP primer

<400> SEQUENCE: 52
gctgctgctt ccaataaact g                                         21

<210> SEQ ID NO 53
<211> LENGTH: 20
<212> TYPE: DNA
<213> ORGANISM: Artificial Sequence
<220> FEATURE:
<223> OTHER INFORMATION: RBBP6 locus-2F human ChIP primer

<400> SEQUENCE: 53
tgagcctggc aatgttgtta                                           20

<210> SEQ ID NO 54
<211> LENGTH: 19
<212> TYPE: DNA
<213> ORGANISM: Artificial Sequence
<220> FEATURE:
<223> OTHER INFORMATION: RBBP6 locus-2R human ChIP primer

<400> SEQUENCE: 54
ccgctgccaa gaactgata                                            19

<210> SEQ ID NO 55
<211> LENGTH: 20
<212> TYPE: DNA
<213> ORGANISM: Artificial Sequence
<220> FEATURE:
<223> OTHER INFORMATION: JMJD3 locus (NFKB binding) 2.1AF human ChIP
      primer

<400> SEQUENCE: 55
gtgggctgag gagttgtgtc                                           20

<210> SEQ ID NO 56
<211> LENGTH: 20
<212> TYPE: DNA
<213> ORGANISM: Artificial Sequence
<220> FEATURE:
<223> OTHER INFORMATION: JMJD3 locus (NFKB binding) 2.1AR human ChIP
      primer

<400> SEQUENCE: 56
ccagaaaacc ttcccctctt                                           20

<210> SEQ ID NO 57
<211> LENGTH: 20
<212> TYPE: DNA
<213> ORGANISM: Artificial Sequence
<220> FEATURE:
<223> OTHER INFORMATION: JMJD3 locus (NFKB binding) 2.1BF human ChIP
```

```
                            primer

<400> SEQUENCE: 57
gtgggctgag gagttgtgtc                                                 20

<210> SEQ ID NO 58
<211> LENGTH: 20
<212> TYPE: DNA
<213> ORGANISM: Artificial Sequence
<220> FEATURE:
<223> OTHER INFORMATION: JMJD3 locus (NFKB binding) 2.1BR human ChIP
      primer

<400> SEQUENCE: 58
cgtgagtcac ccagaaaacc                                                 20

<210> SEQ ID NO 59
<211> LENGTH: 30
<212> TYPE: DNA
<213> ORGANISM: Artificial Sequence
<220> FEATURE:
<223> OTHER INFORMATION: UTX R1111fs frameshift mutation

<400> SEQUENCE: 59
tgcttttgtg cggggcgtaa gtgtcgtatc                                      30

<210> SEQ ID NO 60
<211> LENGTH: 27
<212> TYPE: DNA
<213> ORGANISM: Artificial Sequence
<220> FEATURE:
<223> OTHER INFORMATION: UTX V1113fs frameshift mutation

<400> SEQUENCE: 60
gtgcgtgtcg ggtgtcgtat cagcagg                                         27

<210> SEQ ID NO 61
<211> LENGTH: 36
<212> TYPE: DNA
<213> ORGANISM: Artificial Sequence
<220> FEATURE:
<223> OTHER INFORMATION: UTX V1112fs frameshift mutation

<400> SEQUENCE: 61
ttgtgcgtgt cgtatcaggc taatagcagg aaatct                               36
```

METHODS FOR TREATING T-CELL ACUTE LYMPHOBLASTIC LEUKEMIA

This invention was made with government support under grant numbers R01CA149655 and R01CA133379 awarded by the National Cancer Institute. The government has certain rights in this invention.

This application claims priority benefit of U.S. Provisional Patent Application No. 62/205,407, filed Aug. 14, 2015, which is hereby incorporated by reference in its entirety. This invention was made with government support under RO1CA149655 and RO1CA133379 awarded by National Institutes of Health. The government has certain rights in the invention.

FIELD OF THE INVENTION

The present invention relates to methods for treating T-cell acute lymphoblastic leukemia.

BACKGROUND OF THE INVENTION

Although the cure rate for T cell Acute Lymphoblastic Leukemia (T-ALL) has been improved dramatically during the last couple of decades, the overall prognosis remains dismal, due to frequent disease relapse and the absence of non-cytotoxic targeted therapy options. The role of epigenetic regulation in T-ALL initiation and progression has recently been addressed. Despite the fact that drugs targeting the function of key epigenetic factors, such as histone deacetylase (HDAC) and DNA methyltransferase (DNMT) (Baylin & Jones, "A Decade of Exploring the Cancer Epigenome: Biological and Translational Implications," *Nature Rev. Cancer* 11:726-734 (2011); Boumber & Issa, "Epigenetics in Cancer: What's the Future?" *Oncology* 25:220-226, 228 (2011)), have been approved in the context of hematopoietic disorders, "epigenetic" drugs are currently not used for T-ALL treatment. The recent identification of mutations affecting chromatin modulators in a variety of leukemias (Zhang et al., "The Genetic Basis of Early T-Cell Precursor Acute Lymphoblastic Leukaemia," *Nature* 481: 157-163 (2012); Holmfeldt et al., "The Genomic Landscape of Hypodiploid Acute Lymphoblastic Leukemia," *Nature Genetics* 45:242-252 (2013); Roberts & Mullighan, "How New Advances in Genetic Analysis are Influencing the Understanding and Treatment of Childhood Acute Leukemia," *Curr. Opin. Pediatr.* 23:34-40 (2011); Shih et al., "The Role of Mutations in Epigenetic Regulators in Myeloid Malignancies," *Nat. Rev. Cancer* 12:599-612 (2012); Jankowska et al., "Mutational Spectrum Analysis of Chronic Myelomonocytic Leukemia Includes Genes Associated With Epigenetic Regulation: UTX, EZH2, and DNMT3A." *Blood* 118:3932-3941(2011); Ntziachristos et al., "Mechanisms of Epigenetic Regulation of Leukemia Onset and Progression," *Adv. Immunol.* 117:1-38 (2013)) along with a plethora of recently generated animal models of disease have shed light on the mechanisms of action for this class of epigenetic modifiers in blood cancers. Nevertheless, there is an unmet need for development and utilization of drugs that target the epigenome (McCabe et al., "EZH2 Inhibition as a Therapeutic Strategy for Lymphoma with EZH2-Activating Mutations," *Nature* 492:108-112 (2012); Kruidenier et al., "A Selective Jumonji H3K27 Demethylase Inhibitor Modulates the Proinflammatory Macrophage Response," *Nature* 488: 404-408 (2012); Filippakopoulos et al., "Selective Inhibition of BET Bromodomains," *Nature* 468:1067-1073 (2010); Delmore et al., "BET Bromodomain Inhibition as a Therapeutic Strategy to Target c-Myc," *Cell* 146:904-917 (2011); Bernt et al., "MLL-Rearranged Leukemia is Dependent on Aberrant H3K79 Methylation by DOT1L," *Cancer Cell* 20:66-78 (2011)) in pediatric acute leukemia.

There are currently two characterized H3K27 demethylases that belong to the Jumonji family of deoxygenases. UTX (Hubner & Spector, "Role of H3K27 Demethylases Jmjd3 and UTX in Transcriptional Regulation," *Cold Spring Harb. Symp. Quant. Biol.* 75:43-49 (2011); Kooistra & Helin, "Molecular Mechanisms and Potential Functions of Histone Demethylases," *Nature Rev. Mol. Cell Biol.* 13:297-311(2012)) (KDM6A) is a ubiquitously expressed protein that controls basal levels of H3K27me3, whereas JMJD3 (KDM6B) is induced upon inflammation (De Santa et al., "The Histone H3 Lysine-27 DemethylaseJmjd3 Links Inflammation to Inhibition of Polycomb-Mediated Gene Silencing," *Cell* 130:1083-1094 (2007)), viral, and oncogenic stimuli (Anderton et al., "The H3K27me3 Demethylase, KDM6B, is Induced by Epstein-Barr Virus and Over-Expressed in Hodgkin's Lymphoma." *Oncogene* 30:2037-2043 (2011); Agger et al., "The H3K27me3 Demethylase JMJD3 Contributes to the Activation of the INK4AARF Locus in Response to Oncogene- and Stress-Induced Senescence," *Genes Dev.* 23:1171-1176 (2009); Barradas et al., "Histone Demethylase JMJD3 Contributes to Epigenetic Control of INK4a/ARF by Oncogenic RAS," *Genes Dev.* 23:1177-1182 (2009)). JMJD3 is important for neuronal differentiation (Jepsen et al., "SMRT-Mediated Repression of an H3K27 Demethylase in Progression from Neural Stem Cell to Neuron," *Nature* 450:415-419 (2007)) and promotes epidermal cell differentiation (Sen et al., "Control of Differentiation in a Self-Renewing Mammalian Tissue by the Histone Demethylase JMJD3," *Genes Dev.* 22:1865-1870 (2008)). UTX, in turn, is important for induction of ectoderm and mesoderm differentiation (Morales et al., "Utx Is Required for Proper Induction of Ectoderm and Mesoderm During Differentiation of Embryonic Stem Cells," *PLoS One* 8:e60020 (2013); Wang et al., "UTX Regulates Mesoderm Differentiation of Embryonic Stem Cells Independent of H3K27 Demethylase Activity," *Proc. Natl. Acad. Sci. USA* 109:15324-15329 (2012)). Both have been shown to promote differentiation through expression of the HOX genes (Agger et al., "UTX and JMJD3 are Histone H3K27 Demethylases Involved in HOX Gene Regulation and Development," *Nature* 449:731-734 (2007); Lee et al., "Demethylation of H3K27 Regulates Polycomb Recruitment and H2A Ubiquitination," *Science* 318:447-450 (2007)). Interestingly, JMJD3 and UTX have been found to play different roles in embryonic stem cell physiology, where JMJD3 has been found to inhibit reprogramming with its dual function on INK4a/Arf expression and by mediating PHF20 ubiquitination (Zhao et al., "Jmjd3 Inhibits Reprogramming by Upregulating Expression of INK4a/Arf and Targeting PHF20 for Ubiquitination," *Cell* 152:1037-1050 (2013)), whereas UTX seems to be essential for reprogramming (Mansour et al., "The H3K27 Demethylase Utx Regulates Somatic and Germ Cell Epigenetic Reprogramming," *Nature* 488:409-413 (2012)). Despite such compelling results in developmental systems, the overall understanding of H3K27 demethylases in cancer remains extremely limited (Agger et al., "The H3K27me3 Demethylase JMJD3 Contributes to the Activation of the INK4AARF Locus in Response to Oncogene- and Stress-Induced Senescence," *Genes Dev.* 23:1171-1176 (2009); Barradas et al., "Histone Demethylase JMJD3 Contributes to Epigenetic Control of INK4a/ARF by Oncogenic RAS," *Genes Dev.* 23:1177-1182 (2009)). UTX has been found to control cell fate (Wang et al., "The Histone Demethylase UTX Enables RB-Dependent Cell Fate Control," *Genes Dev.* 24:327-332 (2010)) and to be implicated mainly in solid tumors and less in hematological malignancies (Wang et al., "The Histone Demethylase UTX Enables RB-Dependent Cell Fate Control," *Genes Dev.* 24:327-332 (2010); Tsai et al., "Tumor Suppression by the Histone Demethylase UTX," *Cell Cycle* 9:2043-2044 (2010); Liu et al., "A Functional Role for the Histone Demethylase UTX in Normal and Malignant Hematopoietic Cells," *Exp. Hematol.* 40:487-498 e483 (2012); Thieme et al., "The Histone Demethylase UTX Regulates Stem Cell Migration and Hematopoiesis," *Blood* 121:2462-2473 (2013)), a finding supported mainly through the identification of inactivating mutations (Jankowska et al., "Mutational Spectrum Analysis of Chronic Myelomonocytic Leukemia Includes Genes Associated With Epigenetic Regulation: UTX, EZH2, and DNMT3A." *Blood* 118:3932-3941(2011); Thieme et al., "The Histone Demethylase UTX Regulates Stem Cell Migration and Hematopoiesis," *Blood* 121:2462-2473 (2013); van Haaften et al., "Somatic Mutations of the Histone H3K27 Demethylase Gene UTX in Human Cancer," *Nature Genet.* 41:521-523 (2009); Mar et al., "Sequencing Histone-Modifying Enzymes Identifies UTX Mutations in Acute Lymphoblastic Leukemia," *Leukemia* 26:1881-1883 (2012)). However, the roles of these two demethylases as direct modulators of the oncogenic state are largely uncharacterized.

The present invention is directed to overcoming these and other deficiencies in the art.

SUMMARY OF THE INVENTION

A first aspect of the present invention relates to a method of treating T-cell acute lymphoblastic leukemia in a subject. This method involves selecting a subject having T-cell acute lymphoblastic leukemia, and administering, to the selected subject, an inhibitor of jumonji D3 (JMJD3) demethylase activity at a dosage effective to treat the T cell acute lymphoblastic leukemia in the subject.

Another aspect of the present invention relates to a method of inhibiting T-cell acute lymphoblastic leukemia cell proliferation and/or survival. This method involves administering to a population of T-cell acute lymphoblastic leukemia cells an inhibitor of JMJD3 at a dosage effective to inhibit the T-cell acute lymphoblastic leukemia cell proliferation and/or survival.

To study the interplay between chromatin state and activity of chromatin modifiers in T-ALL in vivo NOTCH1-induced disease animal models (Buonamici et al., "CCR7 Signalling as an Essential Regulator of CNS Infiltration in T-Cell Leukaemia," *Nature* 459:1000-1004 (2009)) have been studied. Since activating mutations in NOTCH1 are a defining feature of >50% of T-ALL cases, this model closely recapitulates many features of human T-ALL, including early developmental arrest in T-cell development, with severe blast infiltration observed in bone marrow and secondary lymphoid tissues. Using molecular and biochemical assays in this mouse model combined with functional and genetic data from primary T-ALL samples, a key tumor-suppressor function was revealed for the Polycomb Repressive Complex 2 (PRC2) that catalyzes methylation of lysine 27 of histone 3 (H3K27) in this type of leukemia (Ntziachristos et al., "Genetic Inactivation of the Polycomb Repressive Complex 2 in T Cell Acute Lymphoblastic Leukemia," *Nature Med.* 18:298-301, doi:10.1038/nm.2651 (2012)). These studies also highlighted a pivotal role for the repressive mark trimethylation of H3K27 (H3K27me3) in leukemogenesis and have demonstrated direct correlation of NOTCH1 binding and H3K27me3 loss during progression of the disease. Since net H3K27me3 levels are dictated by the balance between histone methylation and active demethylation, it was hypothesized that removal of methyl groups from H3K27 is also an important process in T-ALL development. Therefore, possible roles for enzymes with H3K27 demethylase activity have been investigated in T-ALL.

The data herein proposes JMJD3 as a novel therapeutic option for pediatric and adult T-ALL. This proposal is based on recent studies that demonstrate that H3K27me3 catalyzed by the PRC2 complex plays a key role in T-ALL, through antagonism with oncogenic NOTCH1. It is demonstrated here that NOTCH1-mediated recruitment of JMJD3 to promoters can explain this antagonism. It is proposed that NOTCH1 recruitment leads to PRC2 eviction as a result of the active demethylation of H3K27 through the catalytic activity of JMJD3 and the recruitment of JMJD3 to target promoters. By contrast, the reported increases in the levels of the activating H3K4me3 mark on a large fraction of NOTCH1 target genes can be explained by the fact that NOTCH1 has the ability to participate in MLL complexes. Moreover, the anti-tumorigenic activities of the JMJD3 inhibitor, GSKJ4, and its specificity for T-ALL cells are demonstrated. The main action of this inhibitor in T-ALL is considered to be channelled through the inhibition of JMJD3 activity and it is proposed that such compounds be used either as single drugs or in combination with standard chemotherapy for the treatment of T-ALL.

BRIEF DESCRIPTION OF DRAWINGS

FIG. 1A is a size comparison of the spleens (left) and haematoxylin and eosin staining of the liver (right) of healthy (WT, top) and leukemic (T-ALL, bottom) mice. The arrows denote leukemic infiltration of the liver of the T-ALL mouse. Scale bar, 50 mm. Representative samples from n=3 mice are shown. FIGS. 1B-1C show protein (FIG. 1B) and transcript (FIG. 1C) levels of the demethylases JMJD3 and UTX in control T cells (CD4$^+$CD8$^+$ (double positive) thymocytes) and mouse T-ALL cells. Representative samples (FIG. 1B) or the mean±s.d. (FIG. 1C) of three mice is shown; values were normalized according to the sample with the highest expression value. FIG. 1D shows ChIP for JMJD3 on the Hes1 promoter in control T cells and mouse T-ALL cells (left) and upon γ-secretase inhibitor (γSI) treatment of T-ALL cells (right) (n=3): data are shown as mean±s.d. DMSO, dimethylsulphoxide. FIG. 1E shows expression analysis of JMJD3 and HES1 among samples of acute T-cell leukemia (T-ALL; 83 samples), acute B-cell leukemia (B-ALL; 23) and acute myeloid leukemia (AML; 537), as well as physiological T-cell subsets (24) (Dik et al., "New Insights on Human T Cell Development by Quantitative T Cell Receptor Gene Rearrangement Studies and Gene Expression Profiling," *J. Exp. Med.* 201:1715-1723 (2005), which is hereby incorporated by reference in its entirety) (quantile normalization across samples). The data are shown as mean±s.d. The P values (Wilcoxon test) are as follows: for T-ALL versus physiological T cells, $4.0 \times 10^{-6}$; T-ALL versus AML, $1.1 \times 10^{-13}$; T-ALL versus B-ALL, $2.2 \times 10^{-5}$; and for HES1, T-ALL versus physiological T cells, $3.7 \times 10^{-4}$; T-ALL versus AML, $3.5 \times 10^{-43}$; T-ALL versus B-ALL, $1.3 \times 10^{-6}$. ***, significant. FIG. 1F shows snapshots of JMJD3 binding in human T-ALL. Three NOTCH1 targets and the interferon-β (IFNB) gene (negative control) are shown. Chr, chromosome.

FIG. 2A shows levels of p65 (RELA) protein in control T cells and T-ALL tumour cells. A representative sample from three mice is shown. FIG. 2B is a schematic representation of the Jmjd3 locus showing the p65 binding site (upper) and ChIP analysis for p65 binding to the Jmjd3 locus in mouse control T cells and T-ALL tumour cells, as well as T-ALL cells upon treatment with γ-secretase inhibitor (γSI), which affects NOTCH1 levels (center graph). NOTCH1 binding to this region upon γSI treatment in T-ALL cells is also shown (right graph). FIG. 2C is an analysis of JMJD3 and HES1 messenger RNA levels upon γSI treatment of CUTLL1 cells. The average of three independent studies is shown. FIGS. 2D-2E show expression levels of the JMJD3 transcript (FIG. 2D) and protein (FIG. 2E) upon treatment of human T-ALL lines (DND41 and CEM) with a NEMO binding domain (NBD) inhibitor of the NF-κB pathway. FIG. 2F shows JMJD3 levels in T-ALL cells upon inhibition of the NF-κB pathway using a dominant negative form of IκBα (DN-IκBα). FIGS. 2G-2H show ChIP for NOTCH1 (FIG. 2G) and H3K27me3 (FIG. 2H) on the Hes1 promoter upon γSI treatment of mouse T-ALL cells. In FIG. 2D and FIGS. 2F-2H, the average of three studies is shown. In FIG. 2E, a representative example from three studies is shown. FIG. 2I shows genes correlated with selected human genes (including JMJD3 and NFKB1) that were tested for enrichment in loss-of-H3K27me3 during the transition to T-ALL in the mouse model. FIG. 2J shows overlap of JMJD3 peaks with peaks of important activating (H3K4me3 and H3K4me1) and repressive (H3K27me3) epigenetic marks, as well as members of the NOTCH1 complex. The percentage of TSSs containing JMJD3 peaks was used as a conservative control and is an alternative to the much lower genome-wide JMJD3 occupancy. FIG. 2K shows genome-wide distribution of JMJD3 peaks in human T-ALL.

FIG. 3A shows NOTCH1 interaction analyses for JMJD3, MAML1 and WDR5 proteins in 293T cells. Interaction with JMJD3 was confirmed in a reciprocal way (right-most lane, immunoprecipitation (IP) using an anti-haemagglutinin (HA) antibody). FIG. 3B shows expression of JMJD3 and WDR5 in 293T cells, followed by immunoprecipitation using the anti-HA antibody against HAJMJD3. An anti-Flag antibody was used for the detection of both proteins. FIG. 3C shows NOTCH1 interaction studies for JMJD3 and MAML1 proteins in mouse T-ALL cells expressing a Flag/Strep form of intracellular NOTCH1. StrepTactin beads were used for NOTCH1 precipitation in the absence of detectable intracellular NOTCH1, and different antibodies were used for the detection of JMJD3, MAML1, EZH2 and UTX. Extracts from green fluorescent protein (GFP)-expressing cells were used as negative control. All experiments were repeated three times (biological replicates), and a representative example is shown. FIG. 3D shows mRNA expression of JMJD3 and UTX upon treatment with shRNA against JMJD3 or UTX The expression after treatment of CEM cells with two shRNAs against JMJD3 and one shRNA against UTX and one control (Renilla) is shown. FIG. 3E shows the effects on cell proliferation as measured by the loss of GFP-expressing shRNA. HL-60 is an acute promyelocytic leukemia cell line (APL), which is a subtype of acute myeloid leukemia (AML) and is used as control in this study. For both cell lines, the average results from three representative studies are shown. FIG. 3F shows Annexin V staining upon shJMJD3 and shRenilla treatment of CUTLL1 cells (top) and HPB-ALL cells (bottom).

FIGS. 4A-4B show the protein levels of JMJD3 (FIG. 4A) and UTX (FIG. 4B) in human T-ALL cells (CUTLL1) expressing the corresponding shRNAs against the two demethylases. Representative blots from three independent studies (biological replicates) are shown. FIG. 4C shows effects on human T-ALL cell proliferation of shRNA treatment, as measured by loss of green fluorescent protein (GFP)-expressing shRNA. For all cell lines, the mean±s.d. from three representative studies is shown. FIG. 4D shows differential expression analysis upon knockdown of JMJD3 in T-ALL (top). The loci of the downregulated genes exhibit an increase in H3K27me3 (red dots, bottom), whereas the upregulated genes exhibit a decrease in H3K27me3. The data shown are representative of three independent studies. FPKM, fragments per kilobase of transcript per million fragments mapped. FIG. 4E shows in vivo growth of P12 T-ALL cells in intravenous xenograft studies upon genomic ablation of JMJD3 (left) and with a Renilla control (right). One million P12 cells were injected into each of seven animals. Sublethally irradiated NRG (immunocompromised) mice were used as recipients, and transplanted leukemic cell growth was compared with the baseline (day 0). Day 0 was set as the first day when substantially detectable luciferase intensity was measured. The last day of the experiment was the day that either the luciferase intensity reached saturation or the mice were killed for humane reasons. Horizontal bars, means.

FIG. 5A shows JMJD3 but not UTX genetic inactivation impairs the expression of important oncogenic genes. NOTCH1, MYC, and MAZ, as well as JMJD3, expression levels are shown. shUTX treatment results in significant upregulation of JMJD3 compared with shRenilla (control)-treated cells. The average results from three studies are shown. FIG. 5B shows significant expression changes in NRARP transcript levels upon JMJD3 knockdown. FIG. 5C shows ChIP for H3K27me3 on the NRARP locus. FIGS. 5D-5E show binding of JMJD3 to the NOTCH1 (FIG. 5D) and MAZ (FIG. 5E) promoters upon shJMJD3 and shRenilla (control) treatment. The average results from three studies are shown. FIG. 5F shows the numbers of upregulated and downregulated genes for shJMJD3- and shUTX-treated cells compared with shRenilla-treated cells. FIG. 5G is a scatter plot showing the expression levels of important genes in shJMJD3- and shUTX treated CUTLL1 T-ALL cells. Emphasis is given to the NOTCH1 pathway and apoptosis-related genes. This is a scatter plot representation of an expression analysis comparing three independent studies for shJMJD3 and two for shUTX. FIGS. 5H-5I are scatter plots showing the expression levels of important genes in shJMJD3- and shRenilla-treated CCRF-CEM T-ALL cells (FIG. 5H) and in shUTX treated CCRF-CEM T-ALL cells (FIG. 5I). CCRF-CEM cells exhibit increased NOTCH1 levels through mutations in the heterodimerization (HD) domain of NOTCH1 and in the NOTCH1-associated ligase FBW7. Emphasis is given to the NOTCH1 pathway and apoptosis-related genes. This is a scatter plot representation of an expression analysis comparing two studies for shJMJD3, two for shUTX and two for shRenilla.

FIGS. 6A-6B show in vivo growth of CEM T-ALL cells in subcutaneous xenograft studies upon genomic ablation of JAVD3 and UTX (red and green circles denote shJMJD3-expressing cells (two different shRNAs); blue denotes shUTX-expressing cells; and black circles denote shRenilla-expressing cells). One million CEM cells were injected into the animals, and representative graphs from five mouse recipients and an image of a representative mouse on days 0 and 6 are shown (FIG. 6A). Representative graphs from five mouse recipients and the average luciferase intensity on days 0 and 6 are shown (FIG. 6B). FIG. 6C shows results for growth of CEM cells at different time points post transplantation in subcutaneous xenograft studies (n=5). FIG. 6D is a comparison of in vivo cell growth in the subcutaneous model of shJMJD3-, shUTX- and shRenilla-expressing P12 cells (n=5). One million P12 cells were injected into sublethally irradiated NRG (immunocompromised) recipients, and the mice were monitored every day for luciferase activity. Day 0 was the first day that a substantially detectable luciferase intensity was measured. The last day of the experiment was the day that either luciferase intensity reached saturation or the mice were euthanized for humanitarian reasons. Red and green circles denote shJMJD3-expressing cells (two different shRNAs, shJMJD3A and shJMJD3B); blue denotes shUTX-expressing cells; and black circles denote shRenilla-expressing cells. FIG. 6E shows monitoring the change in luciferase intensity over a period of seven days in the subcutaneous xenograft model using CUTLL1 T-ALL cells (n=4). FIGS. 6F-6G show intravenous xenograft studies using CUTLL1 cells injected into sublethally irradiated NRG (immunocompromised) recipients (n=8 or 6, as indicated in the figure). In FIGS. 6E-6G, $0.5 \times 10^6$ CUTLL1 cells were transplanted, and the mice were monitored every day for luciferase activity.

FIGS. 7A-7N show UTX is a tumor suppressor and is genetically inactivated in T-ALL but is dispensable for physiological T-cell development. FIGS. 7A-7B show a study of lymphoid development in $Utx^{-/Y}$ compared with $Utx^{+/+}$, or $Utx^{+/Y}$, background mice. Flow cytometric analyses of $CD4^+$ and $CD8^+$ expression (FIG. 7A), and the relative proportions of $CD4^+CD8^+$ (double-positive) thymocytes across different genotypes (FIG. 7B) are shown. A representative example from three independent samples (biological replicates) is shown. FIG. 7C shows an illustration of the transplantation scheme for the in vivo leukemia studies. FIG. 7L shows the levels of UTX in CUTLL1 T-ALL cells in the absence (–dox) or presence (+dox) of doxycycline. FIGS. 7M-7N show apoptosis analysis through measuring annexin V staining using control LacZ-expressing and UTX-expressing CUTLL1 cells in the absence or presence of doxycycline. Representative plots (FIG. 7L and FIG. 7N), as well as the average results (FIG. 7L and FIG. 7M), from three independent experiments are shown.

FIGS. 8A-8C show monitoring the initiation and progression of T-cell leukemia in a NOTCH1-overexpressing model of T-ALL. Leukemic blasts (expressed as NOTCH1-ICGFP-positive cells) in the peripheral blood (FIG. 8A, mean±s.d.) and in a blood smear (FIG. 8B) and leukemic cell infiltration of the liver (FIG. 8C) of male wild-type ($Utx^{+/Y}$, n=10) and knockout ($Utx^{-/Y}$, n=6) mice are shown. NOTCH1-IC, intracellular part of NOTCH1. FIG. 8D shows survival studies of mice transplanted with haematopoietic progenitors from the wild-type ($Utx^{+/Y}$, n=10) and knockout ($Utx^{-/Y}$, n=6) backgrounds expressing NOTCH1-IC. FIG. 8E is a scatter plot summarizing the major genome-wide expression differences between T-ALL tumors of the wild-type ($Utx^{+/Y}$) and knockout ($Utx^{-/Y}$) backgrounds. RNA sequencing was performed using three pairs of wild-type and Utx knockout (KO) NOTCH1-IC tumors (spleen and bone marrow). FIGS. 8F-8G shows an analysis of genetic status of the UTX (KDM6A) locus in pediatric T cell leukemia (n=107). Affymetrix SNP6.0 microarrays (FIG. 8F) for assessing genomic deletions. Illustration of the human UTX protein (FIG. 8G) depicting three frameshift (fs) mutations in pediatric T-ALL (grey circles), as well as one in-frame deletion (p.Ala14_Ala17del), one splice acceptor site mutation (exon (ex) 4 splice) and one missense mutation (p.Ile598Val) in adult T-ALL (white circles), as identified by targeted Sanger sequencing. The jumonji domain (JmjC) and the tetratricopeptide repeats are shown. SJTALL, St. Jude Children's Research Hospital sample depository of T-ALL samples.

FIGS. 9A-9B show the targeting scheme for the generation of the $Jmjd3^{-/-}$ mouse (FIG. 9A) and PCR-based quantification of the wild-type and mutant transcripts (FIG. 9B) using a specific primer set for the 3' end of Jmjd3 cDNA. FIGS. 9C-9D show analysis of the fetal liver for lineage markers (FIG. 9C), as well as the bone marrow (FIG. 9D) of recipients for hematopoietic progenitors (the Lin2c-Kit1Scal1 (LSK) population), for the $Jmjd3^{+/+}$ and $Jmjd3^{-/-}$ genotypes. Representative plots from three independent experiments are shown. FIGS. 9E-9G show analysis of major thymic subsets in $Jmjd3^{+/+}$ (n=7) and $Jmjd3^{-/-}$ (n=7) mice. Schematic representation of the flow cytometric analysis performed (FIG. 9E). Relative proportions of the major cell populations in the thymi of $Jmjd3^{+/+}$ and $Jmjd3^{-/-}$ mice (FIG. 9F). The mRNA expression of the Jmjd3 gene at different stages of thymic development is shown in FIG. 9G. FIG. 9H shows the expression of NOTCH1 target genes (such as HesI, n=7) in CD4+CD8+ (double positive) and CD4−CD8−CD25+ lymphocyte progenitor cells. Representative plots (FIG. 9E), as well as average results (FIGS. 9G-9H), from seven independent thymi are shown.

FIGS. 10A-10B show blood analysis of the recipients for NOTCH1-ICGFP leukemic blasts (Jmjd3+/−, n=8; Jmjd3−/−, n=8; FIG. 10A) and white blood cells (WBCs, Jmjd3+/−, n=4; Jmjd3−/−, n=6; FIG. 10B). FIGS. 10C-10E show comparison of the organ size (FIG. 10C), histochemistry (hematoxylin and eosin staining) (FIG. 10D) and flow-cytometry-based analysis (FIG. 10E) of the leukemic cell infiltration of the spleen. FIG. 10F shows survival studies of recipients. Eight recipients for the Jmjd3+/− and eight for the Jmjd3−/− background were used in FIG. 10C-10F.

FIG. 11A shows the dose-dependent effect of the inhibitor GSKJ4 (normalized to a control inhibitor, GSKJ5) (Kruidenier et al., "A Selective Jumonji H3K27 Demethylase Inhibitor Modulates the Proinflammatory Macrophage Response," *Nature* 488:404-408 (2012), which is hereby incorporated by reference in its entirety) on CUTLL1 cell proliferation. The data are shown as mean±s.d. FIG. 11B shows the effect of GSKJ4 (at 2 mM) on CUTLL1 T-ALL cells. The data are shown as mean±s.d. FIG. 11C shows a heatmap representation of GSKJ4-associated changes in gene expression (left, three biological replicates) and H3K27me3 changes (right) of 486 significantly downregulated coding transcripts in CUTLL1 T-ALL cells over a period of 72 hours. Center shows occupancy by JMJD3 and NOTCH1 and H3K4me3 marks in respective 4-kilobase (kb)-flanked TSS regions (indicated in different colors from each other). FIG. 11D shows a comparison of the shJMJD3 and shUTX expression-based signatures with the GSKJ4-induced expression changes. Note the highly significant overlap between the genes downregulated by shJMJD3 and GSKJ4. Different colors represent different levels of significance: red, high significance; orange, medium significance; and yellow, low significance. FIG. 11E are box plots representing mean±s.d. GSKJ4-induced H3K27me3 changes in JMJD3 target genes, as well as in the commonly downregulated genes in shJMJD3- and GSKJ4-treated cells. Genes upregulated by both shJMJD3 and GSKJ4 treatments were used as the negative controls. The P values are as follows: JMJD3 targets versus GSKJ4_up and shJMJD3_up, $2.7\times10^{-33}$; and GSKJ4 down and shJMJD3 down versus GSKJ4_up and shJMJD3_up, $4.4\times10^{-15}$. ***, significant.

FIG. 12A shows the effect of GSKJ4 (at 2 mM concentration) on a panel of T-ALL and myeloid lines. The average results from three representative studies are shown. FIG. 12N shows the mRNA levels for three classical NOTCH1 targets (HEY1, NRARP and NOTCH1) over a period of 72 hours during GSKJ4 treatment. The average results from three independent experiments are shown.

FIGS. 13A-13C show analysis of the promoter area of HEY1 (FIG. 13A), NOTCH1 (FIG. 13B) and NRARP (FIG. 13C) for H3K27me3, H3K27me1, NOTCH1 and JMJD3 enrichment over a period of 24 hours during GSKJ4 treatment. The average results from three independent experiments are shown. FIG. 13D shows analysis of the total protein extracts from CUTLL1 cells for JMJD3 and NOTCH1. FIG. 13E shows analysis of the chromatin fraction from CUTLL1 cells for the repressive mark H3K27me3, the activating marks H3K27me1 and H3K4me3, as well as total histone H3 levels. Representative plots from three independent experiments are shown. FIG. 13F shows snapshots of GSKJ4-associated H3K27me3 changes in major NOTCH1 and JMJD3 targets. FIG. 13G shows ChIP-qPCR analyses for UTX binding to the NOTCH1 target genes HEY1, NRARP and NOTCH1 (RBBP6 was used as positive control). The average results from three independent experiments are shown.

FIG. 14A is a schematic representation of the H3K27me3 writer (the polycomb complex, left) and eraser (JMJD3, right). EZH2 contains the catalytic subunit of the complex through its SET domain, whereas the EED subunit recognizes the H3K27me3 mark and aids in polycomb binding. JmjC domain activity is inhibited by the small molecule inhibitor GSKJ4. FIG. 14B demonstrates the key role of JMJD3 in the NOTCH1 transcriptional complex. Before activation of the NOTCH1 signalling pathway, the promoters of classical NOTCH1 target genes are bound by RBP-Jk, together with components of the co-repressor complexes and PRC2, leading to low gene expression. After the binding of NOTCH1 and its co-activator MAML1, the genes are activated through the recruitment of JMJD3 and the MLL complex, with simultaneous eviction of PRC2, which leads to the demethylation of H3K27me3 and the methylation of H3K4me3.

DETAILED DESCRIPTION OF THE INVENTION

Figures 1A, 1B:
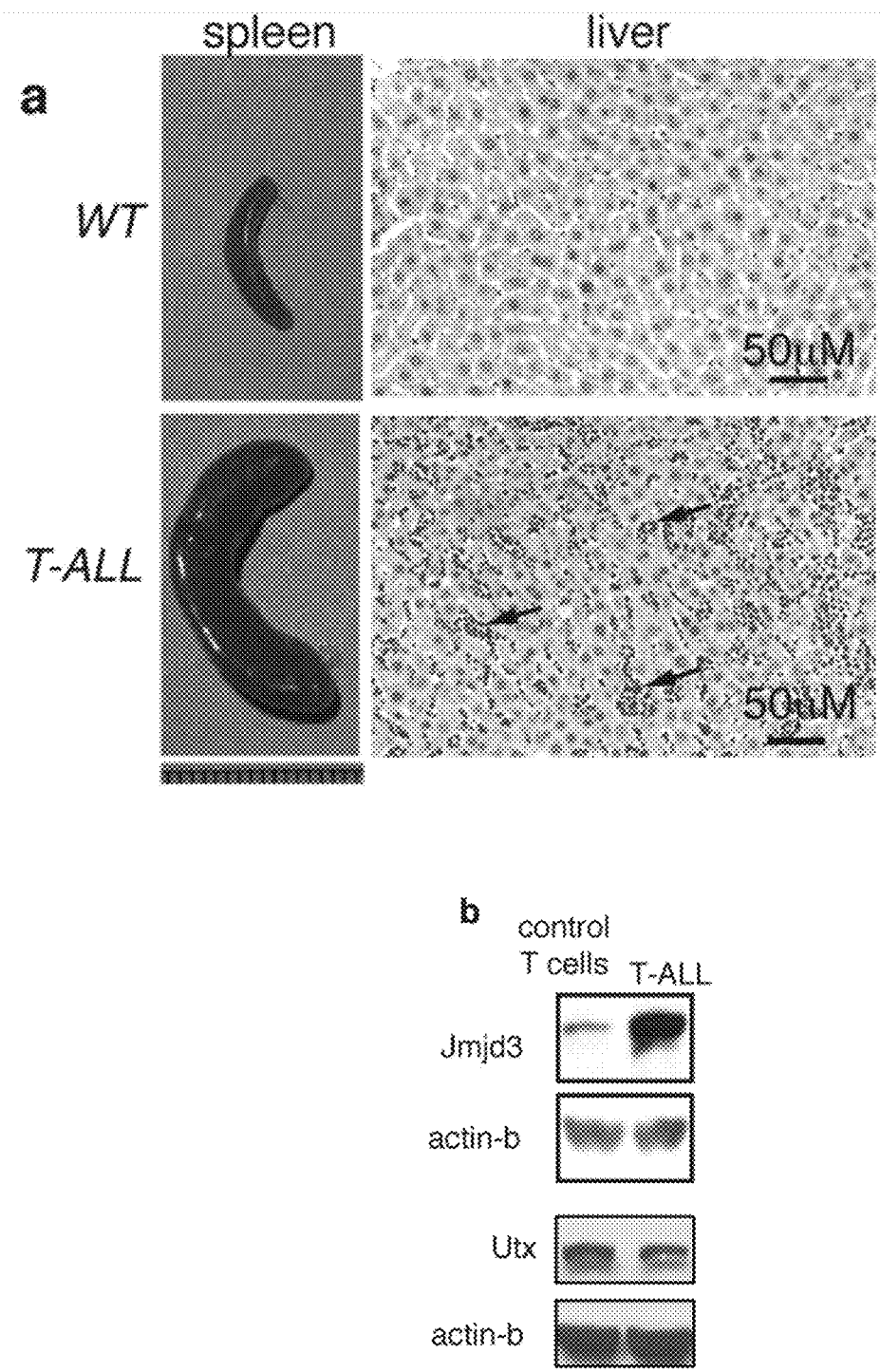
FIGS. 1A-F show JMJD3 is highly expressed in T-ALL, and controls the expression of important oncogenic targets.

A first aspect of the present invention is directed to a method of treating T-cell acute lymphoblastic leukemia in a subject. This method involves selecting a subject having T-cell acute lymphoblastic leukemia and administering, to the selected subject, an inhibitor of jumonji D3 (JMJD3) demethylase activity at a dosage effective to treat the T-cell acute lymphoblastic leukemia in the subject.

As used herein, "subject" refers to any animal having T-cell acute lymphoblastic leukemia, which is amenable to treatment in accordance with the methods of the present invention. Preferably, the subject is a mammal. Exemplary mammalian subjects include, without limitation, humans, non-human primates, dogs, cats, rodents (e.g., mouse, rat, guinea pig), horses, cattle and cows, sheep, and pigs.

As used herein, "T-cell acute lymphoblastic leukemia" (T-ALL) refers to all subtypes of the disease including, but not limited to, adult T-cell acute lymphoblastic leukemia, pediatric T-cell acute lymphoblastic leukemia, and early T-cell precursor acute lymphoblastic leukemia. T-ALL is an aggressive malignant neoplasm of the bone marrow. It accounts for ~20% of all cases of ALL and is somewhat more common in adults than children. The therapeutic agents of the present invention are also suitable to treat the various stages of T-cell acute lymphoblastic leukemia including, but not limited to, pro-T, pre-T, cortical T, medullary T, relapsed T-cell acute lymphoblastic leukemia, and refractory T-cell acute lymphoblastic leukemia. T-ALL is a precursor lymphoid neoplasm and is a distinct entity from adult T-cell leukemia/lymphoma, which is a malignancy of mature T cells caused by human T-cell lymphotrophic virus type I.

As used herein, "treating" T-ALL includes, for example, to cure, heal, alleviate, relieve, alter, remedy, ameliorate, palliate, improve or affect the leukemia, one or more symptoms of the leukemia, or other manifestations of the disease. Treating T-ALL also encompasses inhibiting, impeding and/or slowing the progression of disease. In one embodiment, treatment of T-ALL with a JMJD3 inhibitor as described herein results in complete or partial remission of the disease and/or increases the survival of a subject having TALL. In another embodiment, treatment of a subject having T-ALL with a JMJD3 inhibitor reduces leukemic cell counts in the bone marrow and/or blood, increases production of differentiated cell lineages, decreases transfusion needs, and/or improves one or more clinical symptoms of the disease.

Therapeutic agents of the present invention are agents that inhibit the demethylase activity of JMJD3 and/or the subsequent molecular signaling pathway triggered by the JMJD3-mediated methylation activity.

JMJD3 is one of the approximately 30 JMJC family members found in humans, and functions as a specific demethylase of lysine 27 of histone H3 (H3K27). JMJD3 can demethylate both the tri- and dimethylated H3K27-repressive histone marks, thereby facilitating gene transcription. This was first demonstrated in *C. Elegans* embryogenesis, where JMJD3 was shown to regulate gonadal development through modulation of HOX gene expression (Agger K et al, *Nature* 2007 October; 449(7163); 731-734, which is hereby incorporated by reference in its entirety). Further studies have placed JMJD3 at key cell fate decision checkpoints in T lymphocytes (Miller S A et al, *Genes Dev.* 2008 October; 22; 2280-2993, which is hereby incorporated by reference in its entirety) and macrophages (Ishii M et al, *Blood* 2009 October; 1 14(15); 3244-3254, which is hereby incorporated by reference in its entirety). In addition, JMJD3 has been demonstrated to regulate the differentiation state of the epidermis (Sen G L et al, *Genes Dev.* 2008 July; 22; 1865-1870, which is hereby incorporated by reference in its entirety) and to activate the tumour suppressor, INK4A-Arf, in response stress induced signals (Agger K et al, *Genes Dev.* 2009 April; 23; 1 171-1176, which is hereby incorporated by reference in its entirety). JMJD3 also appears to be involved in more acute, externally-driven, inflammatory processes. In macrophages, for example, JMJD3 is rapidly induced through an NF-κB-dependent mechanism in response to bacterial products and inflammatory stimuli (De Santa F et al, *Cell* 2007 September; 130; 1083-1094, which is hereby incorporated by reference in its entirety). Moreover, depletion experiments in these cells have demonstrated that JMJD3 participates directly in the inflammatory transcriptional response, although it remains unclear whether this is achieved through demethylation of H3K27me3 at target gene promoters (De Santa F et al, *EMBO J.* 2009 September; 28; 3341-3352, which is hereby incorporated by reference in its entirety). The nucleotide and amino acid sequences of the human JMJD3 are well known in the art. The nucleotide sequence for JMJD3 is provided below as SEQ ID NO: 1.

```
ggcaacatgc cagccccgta gcactgccca ccccaccccac tgtggtctgt tgtaccccac    60
tgctggggtg gtggttccaa tgagacaggg cacaccaaac tccatctggc tgttactgag   120
gcggagacac gggtgatgat tggctttctg gggagagagg aagtcctgtg attggccaga   180
tctctggagc ttgccgacgc ggtgtgagga cgctcccacg gaggccggaa ttggctgtga   240
aaggactgag gcagccatct gggggtagcg ggcactctta tcagagcggc tggagccgga   300
ccatcgtccc agagagctgg ggcaggggggc cgtgcccaat ctccagggct cctgggggcca   360 ctgctgacct ggctggatgc atcgggcagt ggaccctcca ggggcccgcg ctgcacggga   420
agcctttgcc cttgggggcc tgagctgtgc tggggcctgg agctcctgcc cgcctcatcc   480
ccctcctcgt agcgcatggc tgcctggagg cagatgctca gccagcattg ggcagccccc   540
gcttcctgct cccctaccccc cttcacatgg cagtagttct gggcacccca gcaaaccata   600
ttatgctcca ggggcgccca ctccaagacc cctccatggg aagctggaat ccctgcatgg   660
ctgtgtgcag gcattgctcc gggagccagc ccagccaggg ctttgggaac agcttgggca   720
actgtacgag tcagagcacg atagtgagga ggccacacgc tgctaccaca gcgcccttcg   780
atacggagga agcttcgctg agctgggggcc ccgcattggc cgactgcagc aggcccagct   840
```

-continued

```
ctggaacttt catactggct cctgccagca ccgagccaag gtcctgcccc cactggagca    900
agtgtggaac ttgctacacc ttgagcacaa acggaactat ggagccaagc ggggaggtcc    960
cccggtgaag cgagctgctg aacccccagt ggtgcagcct gtgcctcctg cagcactctc   1020
aggcccctca ggggaggagg gcctcagccc tggaggcaag cgaaggagag ctgcaactc    1080 tgaacagact ggccttcccc cagggctgcc actgcctcca ccaccattac caccaccacc   1140
accaccacca ccaccaccac caccacccct gcctggcctg gctaccagcc ccccatttca   1200
gctaaccaag ccagggctgt ggagtaccct gcatggagat gcctggggcc cagagcgcaa   1260
gggttcagca cccccagagc gccaggagca gcggcactcg ctgcctcacc catatccata   1320
cccagctcca gcgtacaccg cgcaccccc tggccaccgg ctggtcccgg ctgctccccc   1380
aggcccaggc cccgcccccc caggagcaga gagccatggc tgcctgcctg ccacccgtcc   1440
ccccggaagt gaccttagag agagcagagt tcagaggtcg cggatggact ccagcgtttc   1500
accagcagca accaccgcct gcgtgcctta cgccccttcc cggccccctg gcctccccgg   1560
caccaccacc agcagcagca gtagcagcag cagcaacact ggtctccggg gcgtggagcc   1620
gaacccaggc attcccggcg ctgaccatta ccaaactccc gcgctggagg tctctcacca   1680
tggccgcctg gggccctcgg cacacagcag tcggaaaccg ttcttggggg ctcccgctgc   1740
cactccccac ctatccctgc cacctggacc ttcctcaccc cctccacccc cctgtcccg   1800 cctcttacgc ccccccaccac cccctgcctg gttgaagggt ccggcctgcc gggcagccg   1860 agaggatgga gagatcttag aagagctctt ctttgggact gagggacccc cccgccctgc   1920
cccaccaccc ctccccccatc gcgagggctt cttggggcct ccggcctccc gcttttctgt   1980
gggcactcag gattctcaca cccctcccac tcccccaacc ccaaccacca gcagtagcaa   2040
cagcaacagt ggcagccaca gcagcagccc tgctgggcct gtgtcctttc ccccaccacc   2100
ctatctggcc agaagtatag acccccttcc ccggcctccc agcccagcac agaaccccca   2160
ggacccacct cttgtacccc tgactcttgc cctgcctcca gccctccttt cctcctgcca   2220
ccaaaatacc tcaggaagct tcaggcgccc ggagagcccc cggcccaggg tctccttccc   2280 aaagacccc gaggtggggc cggggccacc cccaggcccc ctgagtaaag ccccccagcc   2340
tgtgccgccc ggggttgggg agctgcctgc ccgaggccct cgactctttg attttccccc   2400
cactccgctg gaggaccagt ttgaggagcc agccgaattc aagatcctac ctgatgggct   2460
ggccaacatc atgaagatgc tggacgaatc cattcgcaag gaagaggaac agcaacaaca   2520
cgaagcaggc gtggcccccc aaccccgct gaaggagccc tttgcatctc tgcagtctcc   2580
tttccccacc gacacagccc ccaccactac tgctcctgct gtcgccgtca ccaccaccac   2640
caccaccacc accaccacca cggccaccca ggaagaggag aagaagccac caccagccct   2700
accaccacca ccgcctctag ccaagttccc tccaccctct cagccacagc caccaccacc   2760 cccaccccc agcccggcca gcctgctcaa atccttggcc tcgtgctgg agggacaaaa   2820 gtactgttat cggggactg gagcagctgt tccacccgg cctgggccct tgcccaccac   2880
tcagtattcc cctggccccc catcaggtgc taccgccctg ccgcccacct cagcggcccc   2940
tagcgcccag ggctccccac agccctctgc ttcctcgtca tctcagttct ctacctcagg   3000
cgggccctgg gccgggagc gcagggcggg cgaagagcca gtcccgggcc ccatgacccc   3060
cacccaaccg ccccccacccc tatctctgcc ccctgctcgc tctgagtctg aggtgctaga   3120
agagatcagc cgggcttgcg agacccttgt ggagcgggtg ggccggagtg ccactgaccc   3180
agccgaccca gtggacacag cagagccagc ggacagtggg actgagcgac tgctgccccc   3240
cgcacaggcc aaggaggagg ctggcggggt ggcggcagtg tcaggcagct gtaagcggcg   3300
```

-continued

```
acagaaggag catcagaagg agcatcggcg gcacaggcgg gcctgtaagg acagtgtggg   3360
tcgtcggccc cgtgagggca gggcaaaggc caaggccaag gtccccaaag aaaagagccg   3420
ccgggtgctg gggaacctgg acctgcagag cgaggagatc cagggtcgtg agaagtcccg   3480
gcccgatctt ggcggggcct ccaaggccaa gccacccaca gctccagccc ctccatcagc   3540
tcctgcacct tctgcccagc ccacaccccc gtcagcctct gtccctggaa agaaggctcg   3600
ggaggaagcc ccaggccac cggtgtcag ccggccgac atgctgaagc tgcgctcact   3660
tagtgagggg ccccccaagg agctgaagat ccggctcatc aaggtagaga gtggtgacaa   3720
ggagaccttt atcgcctctg aggtggaaga gcggcggctg cgcatggcag acctcaccat   3780
cagccactgt gctgctgacg tcgtgcgcgc cagcaggaat gccaaggtga agggaagtt   3840
tcgagagtcc tacctttccc ctgcccagtc tgtgaaaccg aagatcaaca ctgaggagaa   3900
gctgccccgg gaaaaactca acccccctac acccagcatc tatctggaga gcaaacggga   3960
tgccttctca cctgtcctgc tgcagttctg tacagaccct cgaaatccca tcacagtgat   4020
ccggggcctg gcgggctccc tgcggctcaa cttgggcctc ttctccacca agaccctggt   4080
ggaagcgagt ggcgaacaca ccgtggaagt tcgcacccag gtgcagcagc cctcagatga   4140
gaactgggat ctgacaggca ctcggcagat ctggccttgt gagagctccc gttcccacac   4200
caccattgcc aagtacgcac agtaccaggc ctcatccttc caggagtctc tgcaggagga   4260
gaaggagagt gaggatgagg agtcagagga gccagacagc accactggaa cccctcctag   4320
cagcgcacca gacccgaaga accatcacat catcaagttt ggcaccaaca tcgacttgtc   4380
tgatgctaag cggtggaagc cccagctgca ggagctgctg aagctgcccg ccttcatgcg   4440
ggtaacatcc acgggcaaca tgctgagcca cgtgggccac accatcctgg gcatgaacac   4500
ggtgcagctg tacatgaagg tgcccggcag ccgaacgcca ggccaccagg agaataacaa   4560
cttctgctcc gtcaacatca acattggccc aggcgactgc gagtggttcg cggtgcacga   4620
gcactactgg gagaccatca gcgctttctg tgatcggcac ggcgtggact acttgacggg   4680
ttcctggtgg ccaatcctgg atgatctcta tgcatccaat attcctgtgt accgcttcgt   4740
gcagcgaccc ggagacctcg tgtggattaa tgcggggact gtgcactggg tgcaggccac   4800
cggctggtgc aacaacattg cctggaacgt ggggcccctc accgcctatc agtaccagct   4860
ggccctggaa cgatacgagt ggaatgaggt gaagaacgtc aaatccatcg tgcccatgat   4920
tcacgtgtca tggaacgtgg ctcgcacggt caaaatcagc gaccccgact tgttcaagat   4980
gatcaagttc tgcctgctgc agtccatgaa gcactgccag gtgcaacgcg agagcctggt   5040
gcgggcaggg aagaaaatcg cttaccaggg ccgtgtcaag gacgagccag cctactactg   5100
caacgagtgc gatgtggagg tgtttaacat cctgttcgtg acaagtgaga atggcagccg   5160
caacacgtac ctggtacact gcgagggctg tgcccggcgc cgcagcgcag gcctgcaggg   5220
cgtggtggtg ctggagcagt accgcactga ggagctggct caggcctacg acgccttcac   5280
gctggtgagg gcccggcggg cgcgcgggca gcggaggagg gcactggggc aggctgcagg   5340
gacgggcttc gggagcccgg ccgcgccttt ccctgagccc ccgccggctt tctcccccca   5400
ggccccagcc agcacgtcgc gatgaggccg gacgcccgc ccgcctgcct gcccgcgcaa   5460
ggcgccgcgg ggccaccagc acatgcctgg gctggaccta ggtcccgcct gtggccgaga   5520
aggggtcgg gcccagccct tccacccat tggcagctcc cctcacttaa tttattaaga   5580
aaaacttttt tttttttttt agcaaatatg aggaaaaag gaaaaaaat gggagacggg   5640
ggaggggct ggcagcccct cgcccaccag cgcctcccct caccgacttt ggcctttta   5700
```

-continued

```
gcaacagaca caaggaccag gctccggcgg cggcggggt cacatacggg ttccctcacc    5760
ctgccagccg cccgcccgcc cggcgcagat gcacgcggct cgtgtatgta catagacgtt    5820
acggcagccg aggttttaa tgagattctt tctatgggct ttaccctcc cccggaacct     5880
ccttttttac ttccaatgct agctgtgacc cctgtacatg tctctttatt cacttggtta    5940
tgatttgtat tttttgttct tttcttgttt ttttgttttt aatttataac agtcccactc    6000
acctctattt attcattttt gggaaaaccc gacctcccac acccccaagc catcctgccc    6060
gcccctccag ggaccgcccg tcgccgggct ctccccgcgc cccagtgtgt gtccgggccc    6120
ggcccgaccg tctccacccg tccgcccgcg gcttctagccg ggttctcatg gtgctcaaac    6180
ccgctcccct ccctacgtc ctgcacttc tcggaccagt cccccactc ccgacccgac       6240
cccagcccca cctgagggtg agcaactcct gtactgtagg ggaagaagtg ggaactgaaa    6300
tggtattttg taaaaaaat aaataaaata aaaaattaa aggttttaaa gaaagaacta      6360
tgaggaaaag gaaccccgtc cttcccagcc ccggccaact ttaaaaaaca cagaccttca    6420
cccccacccc cttttctttt taagtgtgaa acaacccagg gccagggcct cactgggca     6480
gggacacccc ggggtgagtt tctctggggc tttattttcg ttttgttggt tgttttttct    6540
ccacgctggg gctgcggagg ggtgggggt tacagtccc gcaccctcgc actgcactgt      6600
ctctctgccc caggggcaga ggggtcttcc caaccctacc cctattttcg gtgattttg     6660
tgtgagaata ttaatattaa aataaacgg agaaaaaaaa tcct                      6704
```

The amino acid sequence for JMJD3 is provided below as SEQ ID NO: 2.

```
Met His Arg Ala Val Asp Pro Pro Gly Ala Arg Ala Ala Arg Glu Ala
1               5                   10                  15

Phe Ala Leu Gly Gly Leu Ser Cys Ala Gly Ala Trp Ser Ser Cys Pro
            20                  25                  30

Pro His Pro Pro Arg Ser Ala Trp Leu Pro Gly Gly Arg Cys Ser
        35                  40                  45

Ala Ser Ile Gly Gln Pro Pro Leu Pro Ala Pro Leu Pro Ser His
    50                  55                  60

Gly Ser Ser Ser Gly His Pro Ser Lys Pro Tyr Tyr Ala Pro Gly Ala
65                  70                  75                  80

Pro Thr Pro Arg Pro Leu His Gly Lys Leu Glu Ser Leu His Gly Cys
                85                  90                  95

Val Gln Ala Leu Leu Arg Glu Pro Ala Gln Pro Gly Leu Trp Glu Gln
            100                 105                 110

Leu Gly Gln Leu Tyr Glu Ser Glu His Asp Ser Glu Glu Ala Thr Arg
        115                 120                 125

Cys Tyr His Ser Ala Leu Arg Tyr Gly Gly Ser Phe Ala Glu Leu Gly
    130                 135                 140

Pro Arg Ile Gly Arg Leu Gln Gln Ala Gln Leu Trp Asn Phe His Thr
145                 150                 155                 160

Gly Ser Cys Gln His Arg Ala Lys Val Leu Pro Pro Leu Glu Gln Val
                165                 170                 175

Trp Asn Leu Leu His Leu Glu His Lys Arg Asn Tyr Gly Ala Lys Arg
            180                 185                 190

Gly Gly Pro Pro Val Lys Arg Ala Ala Glu Pro Pro Val Val Gln Pro
        195                 200                 205

Val Pro Pro Ala Ala Leu Ser Gly Pro Ser Gly Glu Glu Gly Leu Ser
    210                 215                 220

Pro Gly Gly Lys Arg Arg Arg Gly Cys Asn Ser Glu Gln Thr Gly Leu
225                 230                 235                 240

Pro Pro Gly Leu Pro Leu Pro Pro Pro Pro Leu Pro Pro Pro Pro Pro
```

-continued

```
                    245                 250                 255
Pro Pro Pro Pro Pro Pro Pro Leu Pro Gly Leu Ala Thr Ser Pro
            260                 265                 270

Pro Phe Gln Leu Thr Lys Pro Gly Leu Trp Ser Thr Leu His Gly Asp
        275                 280                 285

Ala Trp Gly Pro Glu Arg Lys Gly Ser Ala Pro Pro Glu Arg Gln Glu
290                 295                 300

Gln Arg His Ser Leu Pro His Pro Tyr Pro Tyr Pro Ala Pro Ala Tyr
305                 310                 315                 320

Thr Ala His Pro Pro Gly His Arg Leu Val Pro Ala Ala Pro Pro Gly
                325                 330                 335

Pro Gly Pro Arg Pro Pro Gly Ala Glu Ser His Gly Cys Leu Pro Ala
            340                 345                 350

Thr Arg Pro Pro Gly Ser Asp Leu Arg Glu Ser Arg Val Gln Arg Ser
        355                 360                 365

Arg Met Asp Ser Ser Val Ser Pro Ala Ala Thr Thr Ala Cys Val Pro
    370                 375                 380

Tyr Ala Pro Ser Arg Pro Pro Gly Leu Pro Gly Thr Thr Thr Ser Ser
385                 390                 395                 400

Ser Ser Ser Ser Ser Asn Thr Gly Leu Arg Gly Val Glu Pro Asn
                405                 410                 415

Pro Gly Ile Pro Gly Ala Asp His Tyr Gln Thr Pro Ala Leu Glu Val
            420                 425                 430

Ser His His Gly Arg Leu Gly Pro Ser Ala His Ser Ser Arg Lys Pro
        435                 440                 445

Phe Leu Gly Ala Pro Ala Ala Thr Pro His Leu Ser Leu Pro Pro Gly
    450                 455                 460

Pro Ser Ser Pro Pro Pro Pro Cys Pro Arg Leu Leu Arg Pro Pro
465                 470                 475                 480

Pro Pro Pro Ala Trp Leu Lys Gly Pro Ala Cys Arg Ala Ala Arg Glu
                485                 490                 495

Asp Gly Glu Ile Leu Glu Glu Leu Phe Phe Gly Thr Glu Gly Pro Pro
            500                 505                 510

Arg Pro Ala Pro Pro Leu Pro His Arg Glu Gly Phe Leu Gly Pro
        515                 520                 525

Pro Ala Ser Arg Phe Ser Val Gly Thr Gln Asp Ser His Thr Pro Pro
    530                 535                 540

Thr Pro Pro Thr Pro Thr Thr Ser Ser Ser Asn Ser Asn Ser Gly Ser
545                 550                 555                 560

His Ser Ser Pro Ala Gly Pro Val Ser Phe Pro Pro Pro Tyr
                565                 570                 575

Leu Ala Arg Ser Ile Asp Pro Leu Pro Arg Pro Pro Ser Pro Ala Gln
            580                 585                 590

Asn Pro Gln Asp Pro Pro Leu Val Pro Leu Thr Leu Ala Leu Pro Pro
        595                 600                 605

Ala Pro Pro Ser Ser Cys His Gln Asn Thr Ser Gly Ser Phe Arg Arg
    610                 615                 620

Pro Glu Ser Pro Arg Pro Arg Val Ser Phe Pro Lys Thr Pro Glu Val
625                 630                 635                 640

Gly Pro Gly Pro Pro Gly Pro Leu Ser Lys Ala Pro Gln Pro Val
                645                 650                 655

Pro Pro Gly Val Gly Glu Leu Pro Ala Arg Gly Pro Arg Leu Phe Asp
            660                 665                 670

Phe Pro Pro Thr Pro Leu Glu Asp Gln Phe Glu Glu Pro Ala Glu Phe
```

-continued

```
            675                 680                 685
Lys Ile Leu Pro Asp Gly Leu Ala Asn Ile Met Lys Met Leu Asp Glu
            690                 695                 700
Ser Ile Arg Lys Glu Glu Gln Gln Gln His Glu Ala Gly Val Ala
705                 710                 715                 720
Pro Gln Pro Pro Leu Lys Glu Pro Phe Ala Ser Leu Gln Ser Pro Phe
                725                 730                 735
Pro Thr Asp Thr Ala Pro Thr Thr Ala Pro Ala Val Ala Val Thr
                740                 745                 750
Thr Thr Thr Thr Thr Thr Thr Thr Thr Ala Thr Gln Glu Glu Glu
                755                 760                 765
Lys Lys Pro Pro Ala Leu Pro Pro Pro Pro Leu Ala Lys Phe
            770                 775                 780
Pro Pro Pro Ser Gln Pro Gln Pro Pro Pro Pro Pro Pro Ser Pro
785                 790                 795                 800
Ala Ser Leu Leu Lys Ser Leu Ala Ser Val Leu Glu Gly Gln Lys Tyr
                805                 810                 815
Cys Tyr Arg Gly Thr Gly Ala Ala Val Ser Thr Arg Pro Gly Pro Leu
                820                 825                 830
Pro Thr Thr Gln Tyr Ser Pro Gly Pro Ser Gly Ala Thr Ala Leu
                835                 840                 845
Pro Pro Thr Ser Ala Ala Pro Ser Ala Gln Gly Ser Pro Gln Pro Ser
            850                 855                 860
Ala Ser Ser Ser Gln Phe Ser Thr Ser Gly Gly Pro Trp Ala Arg
865                 870                 875                 880
Glu Arg Arg Ala Gly Glu Glu Pro Val Pro Gly Pro Met Thr Pro Thr
                885                 890                 895
Gln Pro Pro Pro Leu Ser Leu Pro Pro Ala Arg Ser Glu Ser Glu
                900                 905                 910
Val Leu Glu Glu Ile Ser Arg Ala Cys Glu Thr Leu Val Glu Arg Val
                915                 920                 925
Gly Arg Ser Ala Thr Asp Pro Ala Asp Pro Val Asp Thr Ala Glu Pro
            930                 935                 940
Ala Asp Ser Gly Thr Glu Arg Leu Leu Pro Ala Gln Ala Lys Glu
945                 950                 955                 960
Glu Ala Gly Gly Val Ala Ala Val Ser Gly Ser Cys Lys Arg Arg Gln
                965                 970                 975
Lys Glu His Gln Lys Glu His Arg Arg His Arg Arg Ala Cys Lys Asp
                980                 985                 990
Ser Val Gly Arg Arg Pro Arg Glu Gly Arg Ala Lys Ala Lys Ala Lys
            995                 1000                1005
Val Pro Lys Glu Lys Ser Arg Arg Val Leu Gly Asn Leu Asp Leu
            1010                1015                1020
Gln Ser Glu Glu Ile Gln Gly Arg Glu Lys Ser Arg Pro Asp Leu
            1025                1030                1035
Gly Gly Ala Ser Lys Ala Lys Pro Pro Thr Ala Pro Ala Pro Pro
            1040                1045                1050
Ser Ala Pro Ala Pro Ser Ala Gln Pro Thr Pro Pro Ser Ala Ser
            1055                1060                1065
Val Pro Gly Lys Lys Ala Arg Glu Glu Ala Pro Gly Pro Pro Gly
            1070                1075                1080
Val Ser Arg Ala Asp Met Leu Lys Leu Arg Ser Leu Ser Glu Gly
            1085                1090                1095
Pro Pro Lys Glu Leu Lys Ile Arg Leu Ile Lys Val Glu Ser Gly
```

-continued

```
                1100            1105            1110
Asp Lys Glu Thr Phe Ile Ala Ser Glu Val Glu Arg Arg Leu
    1115            1120            1125

Arg Met Ala Asp Leu Thr Ile Ser His Cys Ala Ala Asp Val Val
    1130            1135            1140

Arg Ala Ser Arg Asn Ala Lys Val Lys Gly Lys Phe Arg Glu Ser
    1145            1150            1155

Tyr Leu Ser Pro Ala Gln Ser Val Lys Pro Lys Ile Asn Thr Glu
    1160            1165            1170

Glu Lys Leu Pro Arg Glu Lys Leu Asn Pro Pro Thr Pro Ser Ile
    1175            1180            1185

Tyr Leu Glu Ser Lys Arg Asp Ala Phe Ser Pro Val Leu Leu Gln
    1190            1195            1200

Phe Cys Thr Asp Pro Arg Asn Pro Ile Thr Val Ile Arg Gly Leu
    1205            1210            1215

Ala Gly Ser Leu Arg Leu Asn Leu Gly Leu Phe Ser Thr Lys Thr
    1220            1225            1230

Leu Val Glu Ala Ser Gly Glu His Thr Val Glu Val Arg Thr Gln
    1235            1240            1245

Val Gln Gln Pro Ser Asp Glu Asn Trp Asp Leu Thr Gly Thr Arg
    1250            1255            1260

Gln Ile Trp Pro Cys Glu Ser Ser Arg Ser His Thr Thr Ile Ala
    1265            1270            1275

Lys Tyr Ala Gln Tyr Gln Ala Ser Ser Phe Gln Glu Ser Leu Gln
    1280            1285            1290

Glu Glu Lys Glu Ser Glu Asp Glu Glu Ser Glu Pro Asp Ser
    1295            1300            1305

Thr Thr Gly Thr Pro Pro Ser Ser Ala Pro Asp Pro Lys Asn His
    1310            1315            1320

His Ile Ile Lys Phe Gly Thr Asn Ile Asp Leu Ser Asp Ala Lys
    1325            1330            1335

Arg Trp Lys Pro Gln Leu Gln Glu Leu Leu Lys Leu Pro Ala Phe
    1340            1345            1350

Met Arg Val Thr Ser Thr Gly Asn Met Leu Ser His Val Gly His
    1355            1360            1365

Thr Ile Leu Gly Met Asn Thr Val Gln Leu Tyr Met Lys Val Pro
    1370            1375            1380

Gly Ser Arg Thr Pro Gly His Gln Glu Asn Asn Asn Phe Cys Ser
    1385            1390            1395

Val Asn Ile Asn Ile Gly Pro Gly Asp Cys Glu Trp Phe Ala Val
    1400            1405            1410

His Glu His Tyr Trp Glu Thr Ile Ser Ala Phe Cys Asp Arg His
    1415            1420            1425

Gly Val Asp Tyr Leu Thr Gly Ser Trp Trp Pro Ile Leu Asp Asp
    1430            1435            1440

Leu Tyr Ala Ser Asn Ile Pro Val Tyr Arg Phe Val Gln Arg Pro
    1445            1450            1455

Gly Asp Leu Val Trp Ile Asn Ala Gly Thr Val His Trp Val Gln
    1460            1465            1470

Ala Thr Gly Trp Cys Asn Asn Ile Ala Trp Asn Val Gly Pro Leu
    1475            1480            1485

Thr Ala Tyr Gln Tyr Gln Leu Ala Leu Glu Arg Tyr Glu Trp Asn
    1490            1495            1500

Glu Val Lys Asn Val Lys Ser Ile Val Pro Met Ile His Val Ser
```

```
                1505                1510                1515
Trp Asn Val Ala Arg Thr Val Lys Ile Ser Asp Pro Asp Leu Phe
        1520                1525                1530
Lys Met Ile Lys Phe Cys Leu Leu Gln Ser Met Lys His Cys Gln
        1535                1540                1545
Val Gln Arg Glu Ser Leu Val Arg Ala Gly Lys Lys Ile Ala Tyr
        1550                1555                1560
Gln Gly Arg Val Lys Asp Glu Pro Ala Tyr Tyr Cys Asn Glu Cys
        1565                1570                1575
Asp Val Glu Val Phe Asn Ile Leu Phe Val Thr Ser Glu Asn Gly
        1580                1585                1590
Ser Arg Asn Thr Tyr Leu Val His Cys Glu Gly Cys Ala Arg Arg
        1595                1600                1605
Arg Ser Ala Gly Leu Gln Gly Val Val Val Leu Glu Gln Tyr Arg
        1610                1615                1620
Thr Glu Glu Leu Ala Gln Ala Tyr Asp Ala Phe Thr Leu Val Arg
        1625                1630                1635
Ala Arg Arg Ala Arg Gly Gln Arg Arg Arg Ala Leu Gly Gln Ala
        1640                1645                1650
Ala Gly Thr Gly Phe Gly Ser Pro Ala Ala Pro Phe Pro Glu Pro
        1655                1660                1665
Pro Pro Ala Phe Ser Pro Gln Ala Pro Ala Ser Thr Ser Arg
        1670                1675                1680
```

In one embodiment, the JMJD3 demethylase inhibitor comprises ethyl 3-((6-(4,5-dihydro-1H-benzo[d]azepin-3(2H)-yl)-2-(pyridin-2-yl)pyrimidin-4-yl)amino)propanoate (GSK-J4), and active derivatives thereof as disclosed in Kruidenier et al., "A Selective Jumonji H3K27 Demethylase Inhibitor Modulates Proinflammatory Macrophage Response," *Nature* 488:404-408 (2012), which is hereby incorporated by reference in its entirety. GSK-J4 has the structure of:

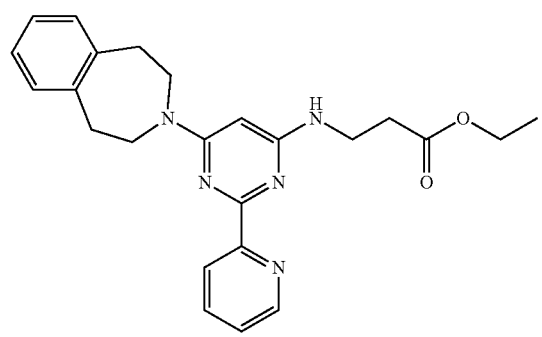

GSK-J4

Exemplary active derivatives of GSK4 that are also JMJD3 demthylase inhibitors include GSK-J1 and GSK-J3, which have the following structures:

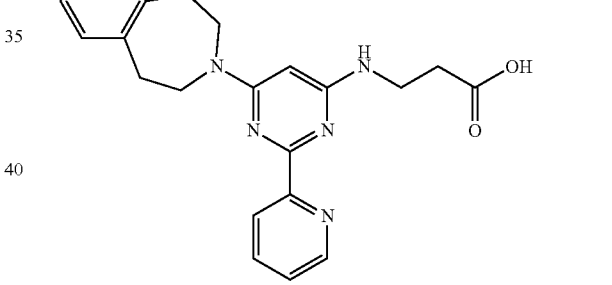

GSK-J1

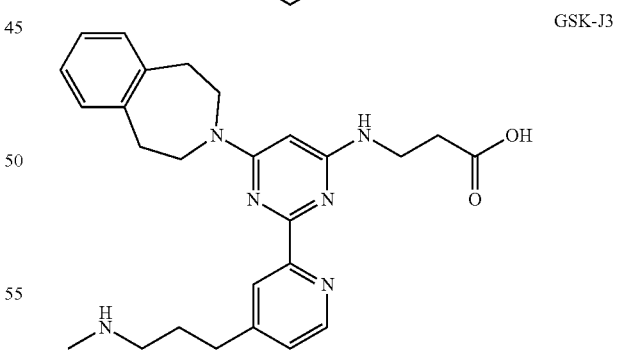

GSK-J3

In another embodiment, the JMJD3 demethylase inhibitor comprises a modified GSK-J1 small molecule as described by Hu et al., "Design and Discovery of New Pyrimidine Coupled Nitrogen Aromatic Rings as Chelating Groups of JMJD3 Inhibitors," *Bioorg. Med. Chem. Lett.* 26(3):721-725 (2016), which is hereby incorporated by reference in its entirety.

In another embodiment, the JMJD3 demethylase inhibitor comprises any of the N-2-(2-pyridinyl)-4-pyrimidinyl-betaalanine derivatives as disclosed in WO2012052390 to Atkinson et al., which is hereby incorporated by reference in its entirety. Exemplary inhibitors include those having the structure of:

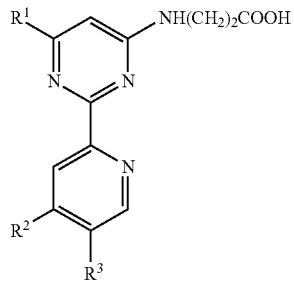

where $R^1$ is $C_{1-6}$ alkyl; $C_{3-7}$ cycloalkyl; $C_{1-6}$ haloalkyl; a 5, 6 or 7-membered aryl or heteroaryl (which heteroaryl contains one or more heteroatoms selected from N, O and S and which is optionally fused to phenyl), said 5, 6 or 7-membered aryl or heteroaryl being optionally substituted with one or more substituents independently selected from $C_{1-3}$alkyl; O—$C_{1-6}$alkyl (which is optionally substituted by phenyl or naphthyl, each of which may be substituted by one of more substituents independently selected from halo); —O-cyclohexyl (which is optionally fused with phenyl); C(O)NR$^c_2$; or NR$^a$R$^b$, each R$^a$ and R$^b$ is independently selected from: H; $C_{1-3}$alkyl which is optionally substituted by one or more substituents independently selected from phenyl (which phenyl is optionally substituted by one or more substituents independently selected from $C_{1-3}$alkyl, O—$C_{1-3}$alkyl, C(O)NR$^c_2$, halo and cyano), C(O)NR$^c_2$, a 4, 5, 6 or 7-membered heterocyclic or heteroaryl group (containing one or more heteroatoms independently selected from N, O and, S), a 3, 4, 5, 6 or 7-membered cycloalkyl group (which is optionally fused to phenyl), halo, OC$_{1-3}$ alkyl, OH, —NHCOC$_{1-3}$alkyl NR$^c_2$ and C(O)NHCH$_2$C(O)NR$^c_2$; a 3, 4, 5, 6 or 7-membered cycloalkyl group (which is optionally fused to phenyl), or R$^a$ and R$^b$ together form a 5, 6 or 7-membered heterocyclic group optionally containing one or more further heteroatoms independently selected from N, O, S or S(O)$_2$ said heterocyclic group being optionally fused to a 5, 6 or 7-membered aryl or heteroaryl ring containing one or more heteroatoms independently selected from N, O and S; the heterocylic ring and/or the aryl or heteroaryl to which it is optionally fused being optionally substituted by one or more substituents independently selected from halo, OH, C$_{1-3}$alkyl, O—C$_{1-3}$alkyl, C(O)C$_{1-3}$ alkyl, S(O)$_2$C$_{1-3}$alkyl, NHC(O)C$_{1-3}$alkyl, NHS(O)$_2$C$_{1-3}$alkyl, C(O)NR$^c_2$, C(O)NR$^d_2$ (wherein R$^d$ and R$^d$ together form a 5 or 6-membered heterocylic ring), NR$^C_2$C(O)phenyl, S(O)$_2$NR$^c_2$, =O(oxo) and 5, 6 or 7-membered aryl or heteroaryl (containing one or more heteroatoms independently selected from N, O and S); R$^2$ and R$^3$ are each independently selected from: H, (CH$_2$)$_{1-3}$NR$^c$(CH$_2$)$_{1-3}$NR$^c_2$, (CH$_2$)$_{1-6}$NR$^c_2$; C$_{1-3}$ alkyl; O—C$_{1-3}$alkyl; C$_{1-3}$haloalkyl; (CH$_2$)$_{0-3}$NR$^a$R$^b$ (wherein R$^a$ and R$^b$ are as defined above); (CH$_2$)$_{0-3}$NHPh; (CH$_2$)$_{0-3}$OPh; (CH$_2$)$_{0-3}$Ph; or R$^2$ and R$^3$ together form a fused phenyl ring, and each R$^c$ is independently selected from hydrogen and C$_{1-3}$alkyl or a pharmaceutically acceptable salt thereof. Suitable inhibitors of this structure include, without limitation, N-[6-(1,1-dimethylethyl)-2-(2-pyridinyl)-4-pyrimidinyl]-β-alanine; N-[2-(2-pyridinyl)-6-(trifluoromethyl)-4-pyrimidinyl]-β-alanine; N-[6-(4-morpholinyl)-2-(2-pyridinyl)-4-pyrimidinyl]-β-alanine; N-[6-(methylamino)-2-(2-pyridinyl)-4-pyrimidinyl]-β-alanine; N-[2-(2-pyridinyl)-6-(1-pyrrolidinyl)-4-pyrimidinyl]-β-alanine; N-[6-[(2-hydroxyethyl)amino]-2-(2-pyridinyl)-4-pyrimidinyl]-β-alanine; N-[6-[(phenylmethyl)amino]-2-(2-pyridinyl)-4-pyrimidinyl]-β-alanine; N-[6-[(2-hydroxyethyl)(methyl)amino]-2-(2-pyridinyl)-4-pyrimidinyl]-β-alanine; N-[6-(dimethylamino)-2-(2-pyridinyl)-4-pyrimidinyl]-β-alanine; and N-[2-(2-pyridinyl)-6-(1,2,4,5-tetrahydro-3/−/-3-benzazepin-3-yl)-4-pyrimidinyl]-β-alanine. Other JMJD3 demethylase inhibitors disclosed in WO2012052390 to Atkinson et al., which is hereby incorporated by reference in its entirety, are also suitable for use in the methods as described herein.

In another embodiment, the JMJD3 demethylase inhibitor comprises any one of the small molecule JMJD3 inhibitors disclosed in WO2013143597 to Barker et al., which is hereby incorporated by reference in its entirety. Exemplary inhibitors include those having the structure of:

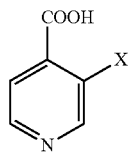

where X is —(R$^1$)o-i-(R$^2$)o-i-R$^3$ or —R$^1$—R$^4$; Each R$^1$ is independently NH, N(CH$_3$), O; R$^2$ is a linker group with a maximum length of 5 atoms between R$^1$ and R$^3$ and is selected from: —CO—C$_{1-6}$ alkyl-, —CO—, —CO—C$_{1-6}$ alkyl-O—, —CO—C$_{1-6}$ alkyl-S—, —CO—C$_{1-6}$ alkyl-O—C$_{1-6}$ alkyl-, —C$_{1-6}$ alkyl-, C$_{1-6}$alkyl-O—, —C$_{1-6}$alkyl-SO$_2$—, —C$_{1-6}$alkyl-NH—CO—, —C$_{1-3}$alkyl-C$_{3-6}$cycloalkyl-C$_{1-3}$alkyl-O— wherein each alkyl is straight chain or branched and may be optionally substituted by one or more substituents independently selected from phenyl or —OH; R$^3$ is selected from: a C$_{6-12}$ mono or bicyclic aryl group, (each of which may be optionally substituted one or more times by substituents independently selected from halo, C$_{1-6}$alkyl, C$_{1-6}$ haloalkyl, C$_{1-6}$alkoxy, NHCOC$_{1-3}$alkyl, —O— phenyl, —CH$_2$-phenyl, phenyl (optionally substituted by C$_{1-3}$alkyl), OH, NH$_2$, CONH$_2$, CN, —NHCOC$_{1-3}$ alkylNH$_2$, —HCOC$_{1-3}$alkyl, NHCOOC$_{1-3}$alkyl, —NHSO$_2$C$_{1-3}$alkyl, —SO$_2$C$_{1-3}$alkyl or —NHCOC$_{1-3}$alkyl-NHCOC$_{1-4}$ alkyl

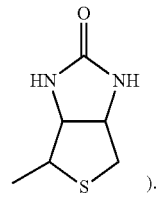

a 5-12 membered mono or bicyclic heteroaryl group (optionally substituted by one or more substituents independently selected from phenyl, CH$_2$phenyl, —C$_{1-6}$ alkyl, -oxo), a 5 or 6 membered heterocyclic group containing one or more heteromoieties independently selected from N, S, SO, SO$_2$ or O and optionally fused to a phenyl group (optionally substituted by one or more substituents independently selected from phenyl, CH$_2$phenyl, C$_{1-6}$ alkyl), or a 3-7 membered cycloalkyl (including bridged cycloalkyl) and optionally fused to a phenyl group (and optionally substituted by one or more substituents independently selected from OH, phenyl, CH$_2$ phenyl), R$^4$ is selected from: C$_{1-6}$ straight chain or branched alkyl (optionally substituted by NH$_2$), COC$_{1-6}$ straight chain or branched alkyl. Suitable inhibitors of this structure include, without limitation, 3-{[(4-chlorophenyl)acetyl]amino}-4-pyridinecarboxylic acid; 3-{[(4-methylphenyl)acetyl]amino}-4-pyridinecarboxylic acid; -[(3-phenylpropanoyl)amino]-4-pyridinecarboxylic acid; -[(phenylcarbonyl)amino]-4-pyridinecarboxylic acid; -[(2,2-dimethylpropanoyl)amino]-4-pyridinecarboxylic acid; -{[(phenyloxy)acetyl]amino}-4-pyridinecarboxylic acid; -{[4-(4-methylphenyl)butanoyl]amino}-4-pyridinecarboxylic acid; -[(2-naphthalenylacetyl)amino]-4-pyridinecarboxylic acid; -{[4-(2-naphthalenyl)butanoyl]amino}-4-pyridinecarboxylic acid; and -{[4-(4-bromophenyl)butanoyl]amino}-4-pyridinecarboxylic acid. Additional small molecule JMJD3 inhibitors disclosed in WO2013143597 to Barker et al., which is hereby incorporated by reference in its entirety, are also suitable for use in the methods described herein.

Small molecule JMJD3 demethylase inhibitors can be readily modified using techniques known in the art to increase bioavailability (see Hetal et al, "A Review on Techniques for Oral Bioavailability Enhancement of Drugs," *Intl. J. Pharm. Sci. Rev. Res.* 4(3): 203-223 (2010) and Huttunen et al., "Prodrugs—from Serendipity to Rational Design," *Pharmacol. Rev.* 63(3):750-771 (2011), which are hereby incorporated by reference in their entirety). For example, common modifications to increase the solubility and dissolution rate of small molecules include particle size reduction, modification of the crystal habit, dispersion in carriers, inclusion complexation, salt formation, and change in pH. Modification of the small molecule into a prodrug form using, for example, attached ionizable or polar neutral groups (e.g., phosphate esters, amino acids, sugar moieties) is also known to enhance solubility and dissolution rate. Common modification to increase permeability and absorption include, for example, conversion of hydrophilic hydroxyl, thiol, carboxyl, phosphate, or amine groups to more lipophilic alkyl or aryl esters.

In another embodiment, the JMJD3 demethylase inhibitor is a JMJD3 antisense RNA, shRNA, or siRNA oligonucleotide.

The use of antisense methods to inhibit the in vivo translation of genes and subsequent protein expression is well known in the art (e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al., which are hereby incorporated by reference in their entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an mRNA molecule (see e.g., Weintraub, H. M., "Antisense DNA and RNA," Scientific Am. 262:40-46 (1990), which is hereby incorporated by reference in its entirety). The antisense nucleic acid molecule hybridizes to its corresponding target nucleic acid molecule, such as JMJD3, to form a double-stranded molecule, which interferes with translation of the mRNA, as the cell will not translate a double-stranded mRNA. Antisense nucleic acids used in the methods of the present invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the JMJD3 nucleotide sequence (SEQ ID NO: 1). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway. shRNA molecules that effectively interfere with JMJD3 expression have been developed, as described herein, and have the following nucleic acid sequences: 5'-CAGGGAAGTTTC-GAGAAGTCCTATAGTGAAGCCACAGATGTATAG-GACTCTCGAAC TTCCCTT-3'(SEQ ID NO: 3) and 5'-ACACCAGCAGTAGCAACAGCAATAGTGAAGC-CACAGATGTATTGCTGTTGCTACTG CTGGTGG-3' (SEQ ID NO: 4).

The therapeutic agents of the present invention can be administered to an individual (e.g., a human) alone or in conjunction with one or more other therapeutic agents of the invention.

In one embodiment, the method involves selecting a subject having T-cell acute lymphoblastic leukemia and administering a chemotherapeutic agent in combination with the inhibitor of JMJD3 demethylase activity at a dosage effective to treat T-cell acute lymphoblastic leukemia in the selected subject.

In accordance with this aspect of the present invention, the chemotherapeutic agent is selected from the group consisting of cytarabine, vincristine, prednisone, doxorubicin, daunorubicin, PEG asparaginase, methotrexate, cyclophosphamide, L-asparaginase, etoposide, and leucovorin.

In one embodiment, the method involves selecting a subject having an activating NOTCH1 mutation. As used herein, "an activating NOTCH1 mutation" is a mutation in NOTCH1 that increases NOTCH1 expression and/or activity. Exemplary NOTCH1 activating mutations include, without limitation, those involving the extracellular heterodimerization domain and/or the C-terminal PEST domain of NOTCH1 as described by Weng et al., "Activating Mutations of NOTCH1 in Human T Cell Acute Lymphoblastic Leukemia," *Science* 306:269-271 (2004), which is hereby incorporated by reference in its entirety.

In a further embodiment, the inhibitor of JMJD3 demethylase activity is administered in combination with a Notch-1 antagonist. Because activation of the Notch-1 signaling pathway has been observed in over 80% of all T-cell acute lymphoblastic leukemia cases, a number of Notch-1 antagonists have been developed and are well known in the art. Suitable Notch-1 antagonists include without limitation gamma-secretase inhibitors selected from the group consisting of [(R2S)-2-{[(3,5-Difluorophenyl)acetyl]amino}-N-[(3S)1-methyl-2-oxo-5-phenyl-2,3-dihydro-1H-1,4-benzodiazepin-3-yl]propanamide] (CompE), N4N-(3,5-difluorophenacetyl)-L-alanyl]-Sphenylglycine-t-butylester (DAPT), LY411575, (5S)-(t-Butoxycarbonylamino)-6-phenyl-(4R)hydroxy-(2R)benzylhexanoyl)-L-leu-L-phe-amide (L-685,458), L-852,647, MW167, WPE-111-31, LY450139, MRK003, R-flurbiprofen ([1,1'-Biphenyl]-4-acetic acid, 2-fluoro-alpha-methyl), NGX-555, CZC-1040, E2012, GSI-1, Begacestat (2-Thiophenesulfonamide, 5-chloro-N-[(1S)-$3_1$3,3-trifluoro-1-(hydroxymethyl)-2-(trifluoromethyl)propyl]-), NIC5-15, BACE Inhibitor, and CHF-5074.

In another embodiment, the inhibitor of JMJD3 demethylase activity is administered in combination with a c-myc inhibitor. A number of c-Myc inhibitors are known in the art and are suitable for use in the methods of the present invention, including nucleic acid inhibitors, peptide inhibitors and small molecule inhibitors. In particular, suitable c-Myc small molecule inhibitors include, without limitation, 10058-F4, 10009-G9, 10031-B8, 10075-G5, 2RH, #474, 12RH-NCN1, 5360134, and 6525237 (see Prochownik and Vogt, "Therapeutic Targeting of Myc," *Genes & Cancer* 1(6) 650-659 (2010); Yin et al., "Low Molecular Weight Inhibitors of Myc-Max Interaction and Function," *Oncogene* 22:6151-59 (2003); and Wang et al., 'Improved Low Molecular Weight Myc-Mas Inhibitors," *Mol. Cancer. Ther.* 6:2399-408 (2007), which are hereby incorporated by reference in their entirety). A suitable polypeptide inhibitor of c-Myc is the 90 amino acid dominant negative miniprotein known as Omomyc (Savino et al., "The Action Mechanism of the Myc Inhibitor Termed Omomyc May Give Clues on How to Target Myc for Cancer Therapy," *PLOS One* 6(7): e22284 (2011), which is hereby incorporated by reference in its entirety).

Suitable nucleic acid inhibitors of c-Myc include siRNA, particularly those siRNA molecules targeting the 3'-untranslated region of the c-Myc (see e.g., von Bueren et al., "RNA Interference-Mediated c-Myc Inhibition Prevents Cell Growth and Decreases Sensitivity to Radio- and Chemotherapy in Childhood Medulloblastoma Cells," *BMC Cancer* 9:10 (2009), which is hereby incorporated by reference in its entirety), c-Myc antisense oligonucleotides (Leonetti et al., "Encapsulation of c-myc Antisense Oligodeoxynucleotides in Lipid Particles Improves Antitumoral Efficacy in Vivo in a Human Melanoma Line," *Cancer Gene Ther.* 8:459-468 (2001); Akie et al., "A Combination Treatment of c-myc Antisense DNA with All-Trans-Retinoic Acid Inhibits Cell Proliferation by Downregulating c-myc Expression in Small Cell Lung Cancer," *Antisense Nucleic Acid Drug Dev.* 10:243-249 (2000); Chen et al., "Molecular Therapy with Recombinant Antisense c-myc Adenovirus for Human Gastric Carcinoma Cells in Vitro and in Vivo," *J. Gastroenterol. Hepatol.* 16:22-28 (2001), which are hereby incorporated by reference in their entirety), c-Myc triple helix forming oligodeoxyribonucleotides (McGuffie et al., "Design of a Novel Triple Helix-Forming Oligodeoxyribonucleotide Directed to the Major Promoter of the c-myc Gene," *Nucleic Acids Res.* 30:2701-09 (2002), which is hereby incorporated by reference in its entirety), and ribozymes (Cheng et al., "Inhibition of Cell Proliferation in HCC-9204 Hepatoma Cells by a c-myc Specific Ribozyme," Cancer *Gene Ther.* 7:407-412 (2000), which is hereby incorporated by reference in its entirety).

In a further embodiment, the inhibitor of JMJD3 demethylase activity is administered in combination with a CDK4/6 inhibitor. Exemplary CDK4/6 inhibitors include, without limitation, Abemaciclib (LY2835219), LEE001, and Palbociclib.

For administration purposes, the JMJD3 demethylase inhibitors of the present invention may be packaged in a suitable delivery vehicle or carrier for delivery to the subject. Suitable delivery vehicles vary depending on the inhibitor (e.g., small molecule vs. nucleic acid inhibitor), but generally include, without limitation, viruses, virus-like particles, bacteria, bacteriophages, coacervates, biodegradable microspheres, microparticles, nanoparticles, exosomes, liposomes, collagen minipellets, and cochleates. These and other biological gene delivery vehicles are well known to those of skill in the art (see e.g., Seow and Wood, "Biological Gene Delivery Vehicles: Beyond Viral Vectors," *Mol. Therapy* 17(5):767-777(2009), which is hereby incorporated by reference in its entirety).

In one embodiment, therapeutic nucleic acid inhibitors of JMJD3 demethylase are packaged into a therapeutic expression vector to facilitate delivery. Suitable expression vectors are well known in the art and include, without limitation, viral vectors such as adenovirus vectors, adeno-associated virus vectors, retrovirus vectors, lentivirus vectors, or herpes virus vectors. The viral vectors or other suitable expression vectors comprise sequences encoding the inhibitory nucleic acid molecule (e.g., siRNA, ASO, etc.) of the invention and any suitable promoter for expressing the inhibitory sequences. Suitable promoters include, for example, and without limitation, the U6 or HI RNA pol III promoter sequences and the cytomegalovirus promoter. Selection of other suitable promoters is within the skill in the art. The expression vectors may also comprise inducible or regulatable promoters for expression of the inhibitory nucleic acid molecules in a tissue or cell-specific manner.

Gene therapy vectors carrying the therapeutic inhibitory nucleic acid molecule are administered to a subject by, for example, intravenous injection, local administration (U.S. Pat. No. 5,328,470 to Nabel et al., which is hereby incorporated by reference in its entirety) or by stereotactic injection (see e.g., Chen et al. "Gene Therapy for Brain Tumors: Regression of Experimental Gliomas by Adenovirus Mediated Gene Transfer In Vivo," *Proc. Nat'l. Acad. Sci. USA* 91:3054-3057 (1994), which is hereby incorporated by reference in its entirety). The pharmaceutical preparation of the therapeutic vector can include the therapeutic vector in an acceptable diluent, or can comprise a slow release matrix in which the therapeutic delivery vehicle is imbedded. Alternatively, where the complete therapeutic delivery vector can be produced intact from recombinant cells, e.g., retroviral vectors, the pharmaceutical preparation can include one or more cells which produce the therapeutic delivery system. Gene therapy vectors typically utilize constitutive regulatory elements which are responsive to endogenous transcriptions factors.

Another suitable approach for delivering nucleic acid or small molecule inhibitors of JMJD3 involves the use of liposome delivery vehicles or nanoparticle delivery vehicles.

In one embodiment of the present invention, the pharmaceutical composition or formulation containing an inhibitory nucleic acid molecule (e.g., siRNA molecule) is encapsulated in a lipid formulation to form a nucleic acid-lipid particle as described in Semple et al., "Rational Design of Cationic Lipids for siRNA Delivery," *Nature Biotech.* 28:172-176 (2010) and International Patent Application Publication Nos. WO2011/034798 to Bumcrot et al., WO2009/111658 to Bumcrot et al., and WO2010/105209 to Bumcrot et al., which are hereby incorporated by reference in their entirety. Other cationic lipid carriers suitable for the delivery of ASO include, without limitation, N-[1-(2,3-dioleoyloxy)propyl]-N,N,N-trimethylammonium chloride (DOTMA) and N-[1-(2,3-dioleoyloxy)propyl]-N,N,N-trimethylammonium methyl sulphate (DOTAP) (see Chan et al., "Antisense Oligonucleotides: From Design to Therapeutic Application," *Clin. Exp. Pharm. Physiol.* 33: 533-540 (2006), which is hereby incorporated by reference in its entirety).

In another embodiment of the present invention, the delivery vehicle is a nanoparticle. A variety of nanoparticle delivery vehicles are known in the art and are suitable for delivery of therapeutic agent of the invention (see e.g., van Vlerken et al., "Multi-functional Polymeric Nanoparticles for Tumour-Targeted Drug Delivery," *Expert Opin. Drug Deliv.* 3(2):205-216 (2006), which is hereby incorporated by reference in its entirety). Suitable polymeric nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly(ethylene glycol) copolymers (Park et al., "Degradable Polyethylenimine-alt-Poly(ethylene glycol) Copolymers As Novel Gene Carriers," *J. Control Release* 105(3):367-80 (2005) and Park et al., "Intratumoral Administration of Anti-KITENIN shRNA-Loaded PEI-alt-PEG Nanoparticles Suppressed Colon Carcinoma Established Subcutaneously in Mice," *J Nanosci. Nanotechnology* 10(5):3280-3 (2010), which are hereby incorporated by reference in their entirety), poly(d,l-lactide-coglycolide) (Chan et al., "Antisense Oligonucleotides: From Design to Therapeutic Application," *Clin. Exp. Pharm. Physiol.* 33: 533-540 (2006), which is hereby incorporated by reference in its entirety), and liposome-entrapped siRNA nanoparticles (Kenny et al., "Novel Multifunctional Nanoparticle Mediates siRNA Tumor Delivery, Visualization and Therapeutic Tumor Reduction In Vivo," *J. Control Release* 149(2): 111-116 (2011), which is hereby incorporated by reference in its entirety). Other nanoparticle delivery vehicles suitable for use in the present invention include microcapsule nanotube devices (see U.S. Patent Publication No. 2010/0215724 to Prakash et al., which is hereby incorporated by reference in its entirety), albumin bound nanoparticles, metallic nanoparticles, and quantum dots (see e.g., babu et al., "Nanoformulations as Drug Delivery Vehicles for Cancer Treatment," Austin J. Nanomed. Nanotech. 3(1): 1038 (2015), which is hereby incorporated by reference in its entirety).

In another embodiment of the present invention, the pharmaceutical composition is contained in a liposome delivery vehicle. The term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Several advantages of liposomes include: their biocompatibility and biodegradability, incorporation of a wide range of water and lipid soluble drugs; and they afford protection to encapsulated drugs from metabolism and degradation. Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Methods for preparing liposomes for use in the present invention include those disclosed in Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., which are hereby incorporated by reference in their entirety.

The liposome and nanoparticle delivery systems can be made to accumulate at a target organ, tissue, or cell via active targeting (e.g., by incorporating an antibody or other ligand on the surface of the delivery vehicle). For example, when targeting T-cell acute lymphoblastic leukemia, as in the present invention, the delivery vehicle may be conjugated to an anti-TALLA-1 antibody as disclosed by Takagi et al., "Identification of a Highly Specific Surface Marker of T-cell Acute Lymphoblastic Leukemia and Neuroblastoma as a New Member of the Transmembrane 4 Superfamily," *Int. I Cancer* 61(5):706-15 (1995), which is hereby incorporated by reference in its entirety, or other antibody recognizing T-ALL specific surface markers.

The therapeutic agents of the present invention can be administered via any standard route of administration known in the art, including, but not limited to, parenteral (e.g., intravenous, intraarterial, intramuscular, subcutaneous injection, intrathecal), oral (e.g., dietary), topical, transmucosal, or by inhalation (e.g., intrabronchial, intranasal or oral inhalation, intranasal drops). Typically, parenteral administration is the preferred mode of administration.

Therapeutic agents of the present invention are formulated in accordance with their mode of administration. For oral administration, for example, the therapeutic agents of the present invention are formulated into an inert diluent or an assimilable edible carrier, enclosed in hard or soft shell capsules, compressed into tablets, or incorporated directly into food. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the agents of the present invention. The agents may be chemically modified so that oral delivery of the derivative is efficacious. Generally, the chemical modification contemplated is the attachment of at least one moiety to the component molecule itself, where said moiety permits inhibition of proteolysis and uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, "Soluble Polymer-Enzyme Adducts," In: *Enzymes as Drugs*, Hocenberg and Roberts, eds., Wiley-Interscience (1981), which is hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, sucralose, or saccharin. When the dosage unit form is a capsule, it may contain, in addition to materials of the above type, a liquid carrier such as a fatty oil.

The therapeutic agents of the present invention may also be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the therapeutic agents of the present invention vary depending upon many different factors, including type and stage of leukemia, mode of administration, target site, physiological state of the patient, other medications or therapies administered, and physical state of the patient relative to other medical complications. Treatment dosages need to be titrated to optimize safety and efficacy. Small molecule JMJD3 inhibitors described herein or pharmaceutically acceptable salts thereof can be administered according to the present invention in an amount selected from 0.01 mg to 1000 mg per day (calculated as the free or unsalted compound). In one embodiment, a therapeutically effective dose of a JMJD3 inhibitor is the dosage required to inhibit at least 50% of JMJD3 demethylase activity. In another embodiment, a therapeutically effective dose of a JMJD3 inhibitor is the dosage required to inhibit at least 55%, 60%, 65%, 70%, 75%, 80%, 85%, 90%, 95%, 100% of JMJD3 demethylase activity.

In a preferred embodiment, the administering step is repeated periodically as needed (e.g., hourly, daily, weekly, monthly, yearly).

The JMJD3 demethylase inhibitors of the present invention can be administered in a single dose or multiple doses. The dosage can be determined by methods known in the art and can be dependent, for example, upon the individual's age, sensitivity, tolerance and overall well-being.

Another aspect of the present invention is directed to a method of inhibiting T-cell acute lymphoblastic leukemia cell proliferation and/or survival. This method involves administering to a population of T-cell acute lymphoblastic leukemia cells an inhibitor of JMJD3 demethylase activity at a dosage effective to inhibit the T-cell acute lymphoblastic leukemia cells proliferation and/or survival.

Suitable therapeutic inhibitors of JMJD3 demethylase activity as well as modes of administration are described supra.

As described herein, leukemia initiating cells represent a subset of leukemic cells that possess properties similar to normal hematopoietic stem cells such as self-renewal, quiescence, and resistance to traditional chemotherapy (Bonnet & Dick, "Human Acute Myeloid Leukemia is Organized as a Hierarchy That Originates From a Primitive Hematopoietic Cell," *Nat. Med.* 3:730-737 (1997); Huntly & Gilliland, "Leukaemia Stem Cells and the Evolution of Cancer-Stem-Cell Research," *Nat. Rev. Cancer* 5:311-321 (2005), which are hereby incorporated by reference in their entirety). As a result, the LIC subset acts as a reservoir of cells contributing to disease, in particular disease relapse. LIC populations have been identified in acute myeloid leukemia, chronic phase and blast crisis CML (Jamieson et al., "Granulocyte-Macrophage Progenitors as Candidate Leukemic Stem Cells In Blast-Crisis CML," *N. Engl. J. Med.* 351:657-667 (2004); Sirard et al., "Normal and Leukemic SCID-Repopulating Cells (SRC) Coexist in the Bone Marrow and Peripheral Blood From CML Patients in Chronic Phase, Whereas Leukemic SRC are Detected in Blast Crisis," *Blood* 87:1539-1548 (1996); Wang et al., "High Level Engraftment of NOD/SCID Mice by Primitive Normal and Leukemic Hematopoietic Cells From Patients With Chronic Myeloid Leukemia in Chronic Phase," *Blood* 91:2406-2414 (1998), which are hereby incorporated by reference in their entirety), and B-cell acute lymphoblastic leukemia (Castro Alves et al., "Leukemia-initiating Cells of Patient-Derived Acute Lymphoblastic Leukemia Xenografts are Sensitive Toward TRAIL," *Blood* 119(18):4224-7 (2012), which is hereby incorporated by reference).

In accordance with this aspect of the present invention, the JMJD3 demethylase inhibitor can be administered in vivo or in vitro to inhibit T-cell acute lymphoblastic leukemia cell proliferation and/or survival. Administration can be repeated periodically as needed (e.g., hourly, daily, weekly, monthly, yearly) to inhibit T-cell acute lymphoblastic leukemia cell proliferation and/or survival.

EXAMPLES

The examples below are intended to exemplify the practice of the present invention but are by no means intended to limit the scope thereof.

Materials and Methods for Examples

Mice, Cell Culture and Primary Cell Samples. The Jmjd3 (Satoh et al., "The Jmjd3-Irf4 Axis Regulates M2 Macrophage Polarization and Host Responses Against Helminth Infection," *Nature Immunol.* 11:936-944 (2010), which is hereby incorporated in its entirety) and Utx (Welstead et al., "X-linked H3K27me3 Demethylase Utx is Required for Embryonic Development in a Sex-Specific Manner," *Proc. Natl. Acad. Sci. USA* 109:13004-13009 (2012), which is hereby incorporated by reference in its entirety) knockout mouse models, as well as the corresponding genotyping strategy, have been described previously. All animals used in this study were treated according to IACU protocols. The human T-ALL cell lines CUTLL1 (Palomero et al., "CUTLL1, a Novel Human T-Cell Lymphoma Cell Line With t(7; 9) Rearrangement, Aberrant NOTCH1 Activation and High Sensitivity to c-Secretase Inhibitors," *Leukemia* 20:1279-1287 (2006), which is hereby incorporated by reference in its entirety), P12-Ichikawa, Loucy, DND41, CEM and Jurkat and the myeloid leukaemia cell lines (THP-1 and HL-60), as well as the mouse T-ALL line (720) (Sharma et al., "Notch1 Contributes to Mouse T-cell Leukemia by Directly Inducing the Expression of c-myc," *Mol. Cell. Biol.* 26:8022-8031 (2006), which is hereby incorporated by reference in its entirety), were cultured in RPMI 1640 medium supplemented with 20% FBS and penicillin and streptomycin. All cell lines were tested for the presence of mycoplasma, and only mycoplasma-free lines were used for these studies. Primary human samples were collected by collaborating institutions with informed consent and were analyzed under the supervision of the Columbia University Medical Center and St. Jude Children's Research Hospital Institutional Review Boards. The primary cells treated with GSKJ4 inhibitor (for more information on these cells, see King et al., "The Ubiquitin Ligase FBW7 Modulates Leukemia-Initiating Cell Activity by Regulating MYC Stability," *Cell* 153:1552-1566 (2013), which is hereby incorporated by reference in its entirety) were cultured in MEMα medium plus 10% FBS (StemCell Technologies, #06400), 10% human AB+ serum (Invitrogen), 1% penicillin/streptomycin, 1% GlutaMAX, human interleukin-7 (IL-7) (R&D Systems; 10 ng ml$^{-1}$), human Flt3 ligand (Peprotech; 20 ngml$^{-1}$), human SCF (Peprotech; 50 ng ml$^{-1}$) and insulin (Sigma; 20 nmol l$^{-1}$). Irradiated M55 stromal cells overexpressing delta-like 1 (DLL1) were used as a feeder layer, as previously described (Armstrong et al., "NOTCH is a Key Regulator of Human T-Cell Acute Leukemia Initiating Cell Activity," *Blood* 113:1730-1740 (2009), which is hereby incorporated by reference in its entirety).

In Vitro Drug Treatment and shRNA Treatment and Cell Growth, Apoptosis and Cell Cycle Analysis.

T-ALL cells were infected twice with shRNA-expressing retroviruses and selected using puromycin. Expression studies took place at different time points during the selection period, and the results are presented from day 4 during selection. To calculate the IC$_{50}$ of GSKJ4 (GlaxoSmith-Kline) (Kruidenier et al., "A Selective Jumonji H3K27 Demethylase Inhibitor Modulates the Proinflammatory Macrophage Response," *Nature* 488:404-408 (2012), which is hereby incorporated by reference in its entirety) normalized to the control inhibitor GSKJ5 (GlaxoSmithKline), T-ALL lines were treated with different concentrations of the drug for 5 days. For cell growth, cell lines and primary cultures were treated with 2 mM GSKJ4 and GSKJ5 for various times (24 hours to 72 hours) and stained with annexin V and subjected to cell cycle analysis. γ-Secretase inhibitor (cSI, specifically Compound E (Alexis Biochemicals)) was used at 500 nM for various periods. For the cell cycle analysis, 5-bromodeoxyuridine (BrdU; 10 mM) was added for a 1 hour pulse, and incorporation into DNA was determined by using the BrdU Flow Kit (BD Biosciences). Apoptosis was studied by quantification of annexin V staining using the BD Biosciences kit and flow cytometry according to standard protocols provided by the manufacturer. Doxycycline was used at 1 mg ml$^{-1}$ final concentration.

Intravenous and Subcutaneous Xenograft Studies.

Studies were conducted as previously published (Ntziachristos et al., "Genetic Inactivation of the Polycomb Repressive Complex 2 in T Cell Acute Lymphoblastic Leukemia," *Nature Med.* 18:298-303 (2012), which is hereby incorporated by reference in its entirety). In both cases, CUTLL1, P12 or CEM T-ALL cells expressing luciferase (FUW-LUC) and the corresponding shRNA (shJMJD3, shUTX or shRenilla) were used. For the intravenous studies, 1×10$^6$ cells were injected retroorbitally into sublethally irradiated female NRG (NOD Rag1$^{-/-}$Il2rg$^{-/-}$) mice. For subcutaneous studies, 1×10$^6$ cells were mixed with an equal volume of BD Matrigel basement membrane and injected into the flanks of female NOD-SCID mice. In both cases, cell growth was monitored every 2 days using IVIS (Caliper, PerkinElmer).

Transplantation for Reconstitution of the Haematopoietic System and for Disease Progression Analysis.

Fetal livers from Jmjd3$^{+/+}$, Jmjd3$^{+/-}$ and Jmjd3$^{-/-}$ embryos (E13.5, Ly45.2 background) were provided by S.A.'s laboratory, and 1×10$^6$ total (unfractionated) fetal liver cells were used for the reconstitution of the haematopoietic system of lethally irradiated recipients on a Ly45.1 background. Bone marrow was isolated from the recipients, followed by isolation of cells of the Ly45.2 background using flow cytometry. Total Ly45.2 bone marrow mononuclear cells (2.5×10$^5$ cells) were mixed with equal numbers of Ly45.1 (wild-type) bone marrow cells and transplanted into lethally irradiated recipients to study haematopoietic reconstitution in a competitive setting.

For the Utx$^{+/+}$, Utx$^{+/-}$ and Utx$^{-/Y}$ (Ly45.2) background, 2.5×10$^5$ cells of total Ly45.2 bone marrow mononuclear cells were mixed with equal numbers of Ly45.1 (wild-type) bone marrow cells and transplanted into lethally irradiated recipients to study haematopoietic reconstitution in a competitive setting similar to the Jmjd3 study.

In both cases, reconstitution of the haematopoietic system was monitored by analysis of the peripheral blood for the main haematopoietic lineages. The thymus and spleen of some recipients were isolated and analyzed at 3 months post transplantation.

Figures 7A, 7B, 7C:
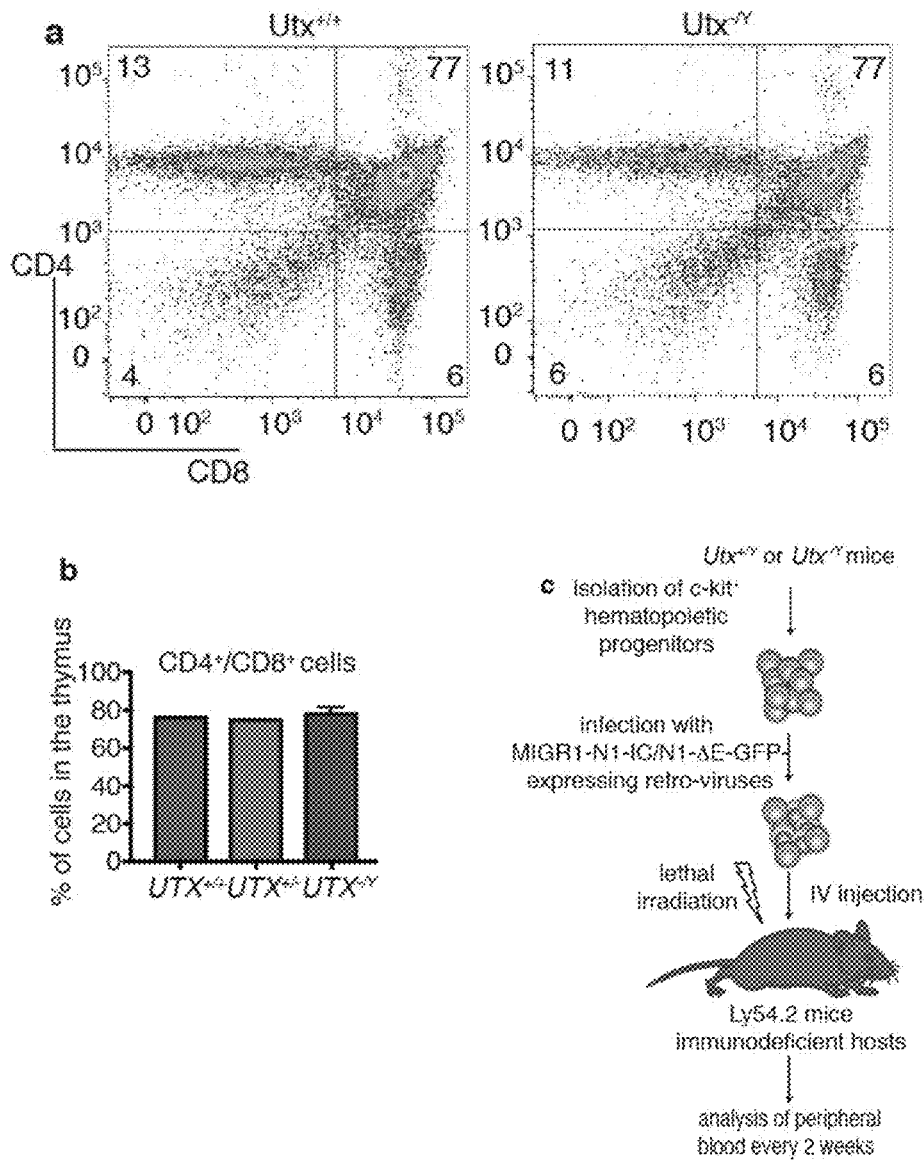
Figures 7D, 7E, 7F, 7G:
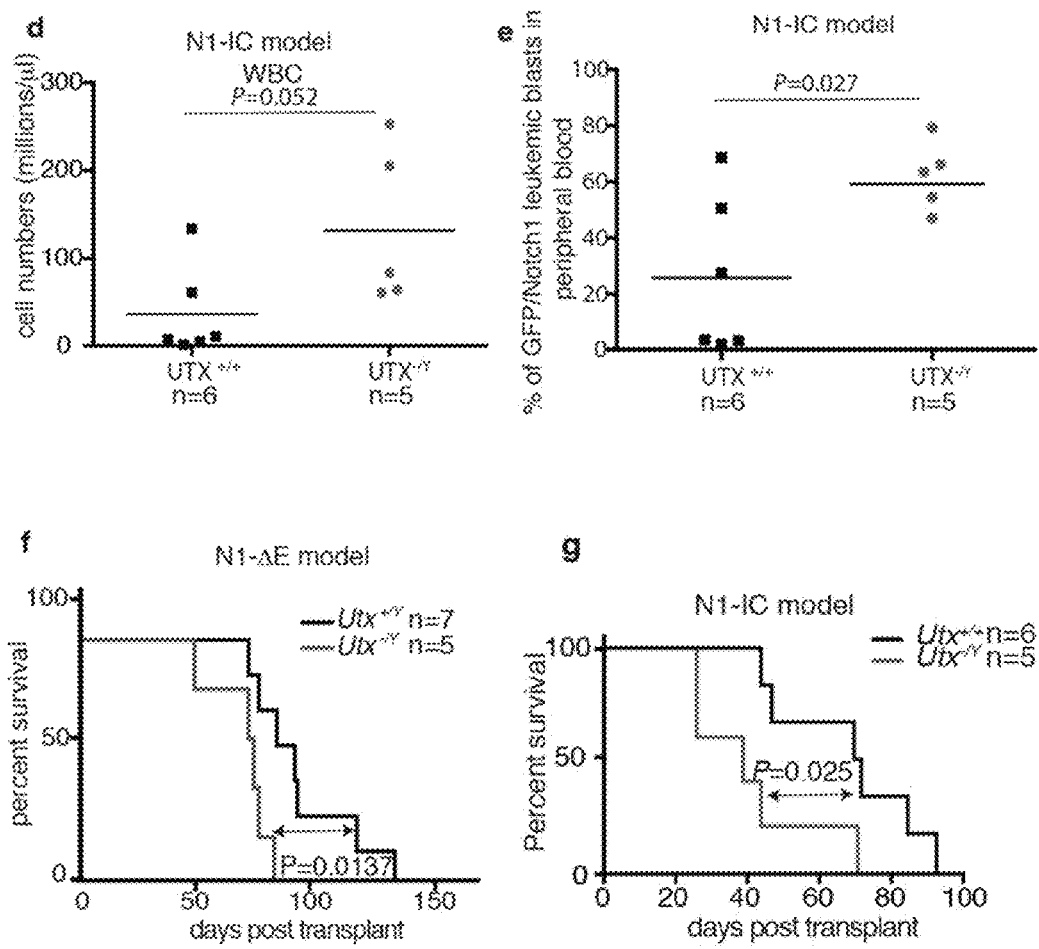
FIGS. 7D-7E show T-ALL progresses faster in the male Utx knockout background ($Utx^{-/Y}$) than in the female wild-type background ($Utx^{+/+}$) in recipients transplanted with NOTCH1-ICGFP-expressing haematopoietic progenitors, as is demonstrated by the white blood cell counts in the peripheral blood (FIG. 7D), as well as the percentage of $GFP^+$ leukemic cells in the peripheral blood upon transplantation of wild-type progenitors (FIG. 7E) from female mice ($Utx^{+/+}$) compared with the corresponding knockout cells ($Utx^{-/Y}$).
FIG. 7F shows a survival study of the recipients of cells from male wild-type ($Utx^{+/Y}$, n=7) and knockout ($Utx^{-/Y}$, n=5) mice expressing NOTCH1-deltaE(ΔE)GFP (an allele with weaker oncogenic action than NOTCH1-IC).
FIGS. 7G-7H show survival analysis of recipients upon transplantation of wild-type progenitors from female mice ($Utx^{+/+}$) compared with the corresponding knockout cells ($Utx^{-/Y}$) carrying NOTCH1-IC (FIG. 7G) or NOTCH1-ΔE (FIG. 7H).

For analysis of leukaemia progression, c-Kit$^+$ haematopoietic progenitors from the bone marrow of both Jmjd3 and Utx knockout models were magnetically selected (STEMCELL Technologies) using an antibody against CD117 (c-Kit) and were cultured overnight in the presence of 50 ng ml$^{-1}$ SCF, 50 ng ml$^{-1}$ Flt3 ligand, 10 ng ml$^{-1}$ IL-3 and 10 ng ml$^{-1}$ IL-6. Overexpression of oncogenic Notch1 mutants (the intracellular part of NOTCH1 (NOTCH1-IC) and DeltaE (NOTCH1-DE)) in bone marrow haematopoietic progenitors followed by transplantation into mouse recipients led to the development of T-ALL, characterized by the presence of leukaemic blasts in the peripheral blood that infiltrated the peripheral lymphoid organs, progressively leading to the death of the animals (FIG. 7C). The cells were infected with NOTCH1-IC or NOTCH1-DE (and green fluorescent protein (GFP)) expressing retroviruses twice (24 hours and 48 hours post c-Kit selection). Viral transduction efficiency was determined by measuring reporter fluorescence over a total period of 4 days, and total populations were transferred via retro-orbital injection into lethally irradiated congenic recipients along with 2.5×10$^5$ total (wild-type) bone marrow mononuclear cells for haemogenic support. GFP$^+$ cells (4×10$^4$) were transplanted in both NOTCH1-IC and NOTCH1-DE studies. The Mantel-Cox test was used for the analysis of the survival data. No randomization or blinding method was used during these animal studies.

Antibodies, Reagents, Kits and Virus Production.

Protein-G-coated magnetic beads were purchased from Invitrogen. Antibodies against the following proteins were used: monoclonal mouse H3K27me3 (histone H3 migrates at around 17 kDa) (Abcam, ab6002), monoclonal mouse H3K27me1 (Active Motif, 61015), polyclonal rabbit H3K4me3 (ActiveMotif, 39159), polyclonal rabbit NOTCH1 (the intracellular part of the protein migrates at around 110 kDa), polyclonal rabbit JMJD3 (protein migrates at around 170 kDa) (Abgent, AP1022a (human) and AP1022b (mouse)), as well as polyclonal rabbit JMJD3 (Cell Signaling Technology, 3457), polyclonal rabbit UTX (protein migrates at around 160 kDa) (Abcam, ab36938, and Bethyl Laboratories, A302-374A), polyclonal rabbit NF-kB (p65, protein migrates at around 65 kDa) (SantaCruz Biotechnology, sc-109 and sc-372) and control IgG (SantaCruz Biotechnology, msc-2025 (mouse) and sc-2027 (rabbit)). All antibodies for flow cytometry were from eBioscience. All antibodies used had been tested and shown to be specific by the suppliers for the purposes used. The acid extraction protocol by Abcam was used for the characterization of histone mark levels upon GSKJ4 treatment. To generate the virus, 293T cells were infected with a plasmid expressing the shRNA (an miR-30-based system (Dickins et al., "Probing Tumor Phenotypes Using Stable and Regulated Synthetic MicroRNA Precursors," *Nature Genet.* 37:1289-1295 (2005), which is hereby incorporated by reference in its entirety)) against JMJD3 or UTX(shJMJD3A, 5'-CAGGGAAGTTTCGAGAAGTCCTATAGTGAAGCCACAGATGATGTATAGG ACTCTCGAACTTCCCTT-3' (SEQ ID NO: 3); shJMJD3B, 5'-ACACCAGCAGTAGCAACAGC AATAGTGAAGCCACAGATGTATTGCTGTTGCTACT-GCTGGTGG-3' (SEQ ID NO: 4); shUTX, 5'-ACA-CAAGGTAGTCTACAGAATATAGTGAAGCCACAGAT-GTATATTCTGTAGACTACC TTGTGG-3') (SEQ ID NO: 5). shRenilla (5'-CTCGAGAAGGTATATTGCTGTT-GACAGTGAGCGCAGGAATTATAATGCTTATCTATA GTGAAGCCACAGATGTATAGATAAGCATTATAATTC-CTATGCCTACTGCCTCGGAAT TC-3') (SEQ ID NO: 6) was also used as a control and the retroviral packaging plasmid. Viral supernatant was collected over a period of 72 hours and used for the transduction of T-ALL cells. The cells were infected twice and then selected with puromycin starting 3 days after viral infection. Reporter fluorescence was used (as determined by flow cytometry) for the quantification of shRNA.

Histopathology.

Organs were harvested from the animals and immersion fixed with 4% paraformaldehyde 4 overnight at 4° C. Samples were washed with PBS three times for 1 hour at room temperature and dehydrated in 70% ethanol. Samples were embedded in paraffin blocks. Sections (6-mm thick) were stained with haematoxylin and eosin following standard procedures. Peripheral blood smears were briefly fixed in methanol and stained with Wright-Giemsa solution (Fisher). Slides were rinsed with water, dried, mounted with Cytoseal 60 and coverslipped.

Protein Immunoprecipitation for Interaction Studies.

For the interaction studies between the NOTCH1 complex (NOTCH1 and MAML1) and the epigenetic modulators (UTX, JMJD3 and EZH2), standard protocols used elsewhere were used.

In brief, cells were resuspended in TENT buffer (50 mM Tris, pH8.0, 5 mM EDTA, 150 mM NaCl and 0.05% (v/v) Tween-20) supplemented with the inhibitors at a concentration of 20×10$^6$ cells ml$^{-1}$ buffer. Cell lysates were passed through a 25G syringe five times and incubated on ice for 30 minutes, followed by centrifugation to remove cell debris (5 minutes, 13,000 g). The cleared lysate was precleared with beads for 1 hour at 4° C. to decrease non-specific binding and incubated overnight with the corresponding antibody-bound bead complexes. Five micrograms of antibody was used for 3 mg of extracts.

RNA-seq Library Preparation and Analysis.

Whole RNA was extracted from 1-5×10$^6$ T-ALL cells or primary cells using the RNeasy kit (QIAGEN) according to the manufacturer's protocol. Poly(A)$^+$ RNA was enriched using magnetic oligo(dT)-containing beads (Invitrogen). cDNA was prepared and strand-specific libraries were constructed using the dUTP method as described previously (Zhong et al., "High-Throughput Illumina Strand-Specific RNA Sequencing Library Preparation," *Cold Spring Harb. Protoc.* 2011:940-949 (2011), which is hereby incorporated by reference in its entirety). Libraries were sequenced on the Illumina HiSeq 2000 using the 50-base-pair single-read method.

ChIP and ChIP-seq Library Preparation.

ChIP experiments were performed as described previously (Ntziachristos et al., "Genetic Inactivation of the Polycomb Repressive Complex 2 in T Cell Acute Lymphoblastic Leukemia," *Nature Med.* 18:298-303 (2012), which is hereby incorporated by reference in its entirety). In brief, for the analysis of histone marks, the cells were fixed with 1% formaldehyde for 10 minutes at 25° C. and lysed them by the addition of nucleus incubation buffer (15 mM Tris, pH 7.5, 60 mM KCl, 150 mM NaCl, 15 mM MgCl$_2$, 1 mM CaCl$_2$, 250 mM sucrose and 0.3% NP-40) and incubation at 4° C. for 10 minutes. The nuclei were washed once with digest buffer (10 mM NaCl, 10 mM Tris, pH7.5, 3 mM MgCl$_2$ and 1 mM CaCl$_2$), and micrococcal nuclease (USB)

in digest buffer was used to generate mononucleosomal particles. The reaction was stopped by the addition of EDTA (20 mM). The nuclei were lysed in nucleus lysis buffer (50 mM Tris-HCl, pH 8.0, 10 mM EDTA, pH 8.0, and 1% SDS) followed by sonication using a Bioruptor (Diagenode), and chromatin was precleared by the addition of nine volumes of IP dilution buffer (0.01% SDS, 1.1% Triton X-100, 1.2 mM EDTA, pH 8.0, 16.7 mM Tris-HCl, pH 8.0, and 167 mM NaCl) and magnetic Dynabeads. One percent of the chromatin was kept as input. 2.5 mg antibody was coupled with 25 ml of beads for 4 hours in reaction buffer, and the complex was added to precleared chromatin (the equivalent of $10^5$-$10^6$ cells, depending on the antibody) followed by overnight incubation at 4° C. with rotation. The complexes were washed bound to the beads using buffers with increasing salt concentration: once with wash A (20 mM Tris-HCl, pH8, 150 mM NaCl, 2 mM EDTA, 1% (w/v) TritonX-100 and 0.1% (w/v) SDS), once with wash B (20 mM Tris-HCl, pH8.0, 500 mM NaCl, 2 mM EDTA, I % (w/v) Triton X-100 and 0.1% (w/v) SDS), once with wash C (10 mM Tris-HCl, pH8.0, 250 mM LiCl, 1 mM EDTA, I % (w/v) NP-40 and 1% (w/v) deoxycholic acid) and twice with TE, followed by treatment with RNase and proteinase K. The crosslinks were then reversed, and the DNA was precipitated using ethanol and glycogen.

For JMJD3 ChIP, the cells were fixed with 1% formaldehyde for 10 minutes at 25° C. and lysed on ice using 1 ml cell lysis buffer (50 mM HEPES-KOH, pH7.5, 140 mM NaCl, 1 mM EDTA, 10% glycerol, 0.5% NP-40 and 0.25% Triton X-100) per $1\times10^7$ cells. The pellet was resuspended in 1 ml buffer 11 (10 mM Tris-HCl, pH8, 200 mM NaCl, 1 mM EDTA, pH 8, and 0.5 mM EGTA) per $1\times10^7$ cells. The nuclei were further resuspended in buffer III (10 mM Tris-HCl, pH8, 100 mM NaCl, 1 mM EDTA, 0.5 mM EGTA, 0.1% sodium deoxycholate and 0.5% n-lauroylsarcosine) and sonicated the solution with a Bioruptor for 40 minutes. Triton X-100 was added to a final concentration of 1%, and the chromatin preparation was precleared using magnetic beads. The antibody (5 mg) was coupled to the magnetic beads (50 ml) as in the case of the histone marks, and the complex was added to the precleared chromatin (the equivalent of $1\times10^7$ cells per reaction). The reaction mix was then incubated for 12-16 hours. The beads with the immunoprecipitated chromatin fragments were washed eight times with RIPA buffer (50 mM HEPES-KOH, pH 7.6, 300 mM LiCl, 1 mM EDTA, 1% NP-40 (IGEPAL) and 0.7% sodium deoxycholate) and once with TE. The DNA was cleaned as in the case of the chromatin marks (see above). Libraries were generated as described previously (Ntziachristos et al., "Genetic Inactivation of the Polycomb Repressive Complex 2 in T Cell Acute Lymphoblastic Leukemia," Nature Med. 18:298-303 (2012), which is hereby incorporated by reference in its entirety), including end repair, A-tailing, adaptor ligation (Illumina TruSeq system) and PCR amplification of the libraries. AMPure XP beads (Beckman Coulter, A63880) were used for DNA cleaning in each step of the process.

Sequence Analysis of Primary Samples.

Sequencing and analysis of pediatric T-ALL samples was conducted as described in previously published studies (Zhang et al., "The Genetic Basis of Early T-cell Precursor Acute Lymphoblastic Leukaemia," Nature 481:157-163 (2012); Mullighan, C. G., "Single Nucleotide Polymorphism Microarray Analysis of Genetic Alterations in Cancer," Methods Mol. Biol. 730:235-258 (2011), which are hereby incorporated by reference in their entirety). In brief, sequencing of UTX in the pediatric T-ALL cohort was performed by PCR of whole genome amplified DNA, followed by sequencing using 3730×1 instruments (Applied Biosystems) as previously described (Mullighan et al., "CREBBP Mutations in Relapsed Acute Lymphoblastic Leukaemia," Nature 471:235-239 (2011), which is hereby incorporated by reference in its entirety). Single nucleotide variations were detected by SNPdetector (Zhang et al., "SNPdetector: a Software Tool for Sensitive and Accurate SNP Detection," PLOS Comput. Biol. 1:e53 (2005), which is hereby incorporated by reference in its entirety) and PolyScan (Chen et al., "PolyScan: An Automatic Indel and SNP Detection Approach to the Analysis of Human Resequencing Data," Genome Res. 17:659-666 (2007), which is hereby incorporated by reference in its entirety) and validated by sequencing of both tumour and matched non-tumour samples. A total of 107 pediatric patients were screened, including 64 cases with ETP ALL (25 females and 39 males) and 43 with 'typical' T-ALL (8 females and 35 males). UTX mutations were detected in 4.7% of the total population and in 6.8% of the male population. No UTX mutations were detected in female samples. The two deletions and one of the frameshift mutations were found in patients with typical T-ALL, and the other two in patients with ETP ALL.

Regarding the adult T-ALL case, all 83 samples were collected in the Eastern Cooperative Oncology Group (ECOG) clinical trials E2993 (Marks et al., "T-Cell Acute Lymphoblastic Leukemia in Adults: Clinical Features, Immunophenotype, Cytogenetics, and Outcome From The Large Randomized Prospective Trial (UKALL XIFECOG 2993)," Blood 114; 5136-5145 (2009), which is hereby incorporated by reference in its entirety) and C10403 and analyzed under the supervision of the Columbia University Medical Center Institutional Review Board. Informed consent to use leftover material for research purposes was obtained from all of the patients at trial entry in accordance with the Declaration of Helsinki. All exon sequences from UTX were amplified from genomic DNA by PCR and analyzed by direct dideoxynucleotide sequencing. The primer sequences used for UTX sequencing have been described previously (van Haaften et al., "Somatic Mutations of the Histone H3K27 Demethylase Gene UTX in Human Cancer," Nature Genet. 41:521-523 (2009), which is hereby incorporated by reference in its entirety).

Data Sources and Computational Tools.

Patient and physiological T-cell expression data were obtained from Zhang et al., "The Genetic Basis of Early T-cell Precursor Acute Lymphoblastic Leukaemia," Nature 481:157-163 (2012), Dik et al., "New Insights on Human T Cell Development by Quantitative T Cell Receptor Gene Rearrangement Studies and Gene Expression Profiling," J. Exp. Med. 201:1715-1723 (2005), and Verhaak et al., "Prediction of Molecular Subtypes in Acute Myeloid Leukemia Based on Gene Expression Profiling," Haematologica 94:131-134 (2009), which are hereby incorporated by reference in their entirety. Human genome assembly version hg19/GRCh37 and Ensembl annotation release 69 were used for the RNA-seq, ChIP-seq and data integration analyses. NOTCH1, RBP-J, H3K4me3 and H3K27me3 ChIPseq data for CUTLL1 cells were obtained from Wang et al., "Genome-Wide Analysis Reveals Conserved and Divergent Features of Notch1/RBPJ Binding in Human and Murine T-Lymphoblastic Leukemia Cells," Proc. Natl. Acad. Sci. USA 108:14908-14913 (2011), which is hereby incorporated by reference in its entirety. For the functional enrichment analysis, MSigDB42 version 3.1 was used. Bowtie (Langmead et al., "Ultrafast and Memory-Efficient Alignment of Short DNA Sequences to the Human Genome," Genome

*Biol.* 10:R25 (2009), which is hereby incorporated by reference in its entirety) version 0.12.7 was used for alignment of sequenced reads. RNA-seq data analysis was performed using DEGseq (Wang et al., "DEGseq: an R Package for Identifying Differentially Expressed Genes from RNA-Seq Data," *Bioinformatics* 26:136-138 (2010), which is hereby incorporated by reference in its entirety). MACS (Zhang et al., "Model-Based Analysis of ChIP-Seq (MACS)," *Genome Biol.* 9:R137 (2008), which is hereby incorporated by reference in its entirety) version 2.0.10 was used for JMJD3 ChIP-seq peak discovery, in conjunction with the irreproducible discovery rate (IDR) method (Li et al., "Measuring Reproducibility of Highthroughput Experiments," *Ann. Appl. Stat.* 5:1752-1779 (2011), which is hereby incorporated by reference in its entirety). GenomicTools (Tsirigos et al., "GenomicTools: A Computational Platform for Developing High-Throughput Analytics in Genomics," *Bioinformatics* 28:282-283 (2012), which is hereby incorporated by reference in its entirety) version 2.7.2 was used for performing genomic interval mathematical operations, genomic interval annotation, H3K27me3 ChIP-seq comparisons (GSKJ4 versus control) and ChIP-seq heatmap generation.

Expression Analysis of Primary Samples.

Figures 1C, 1D:
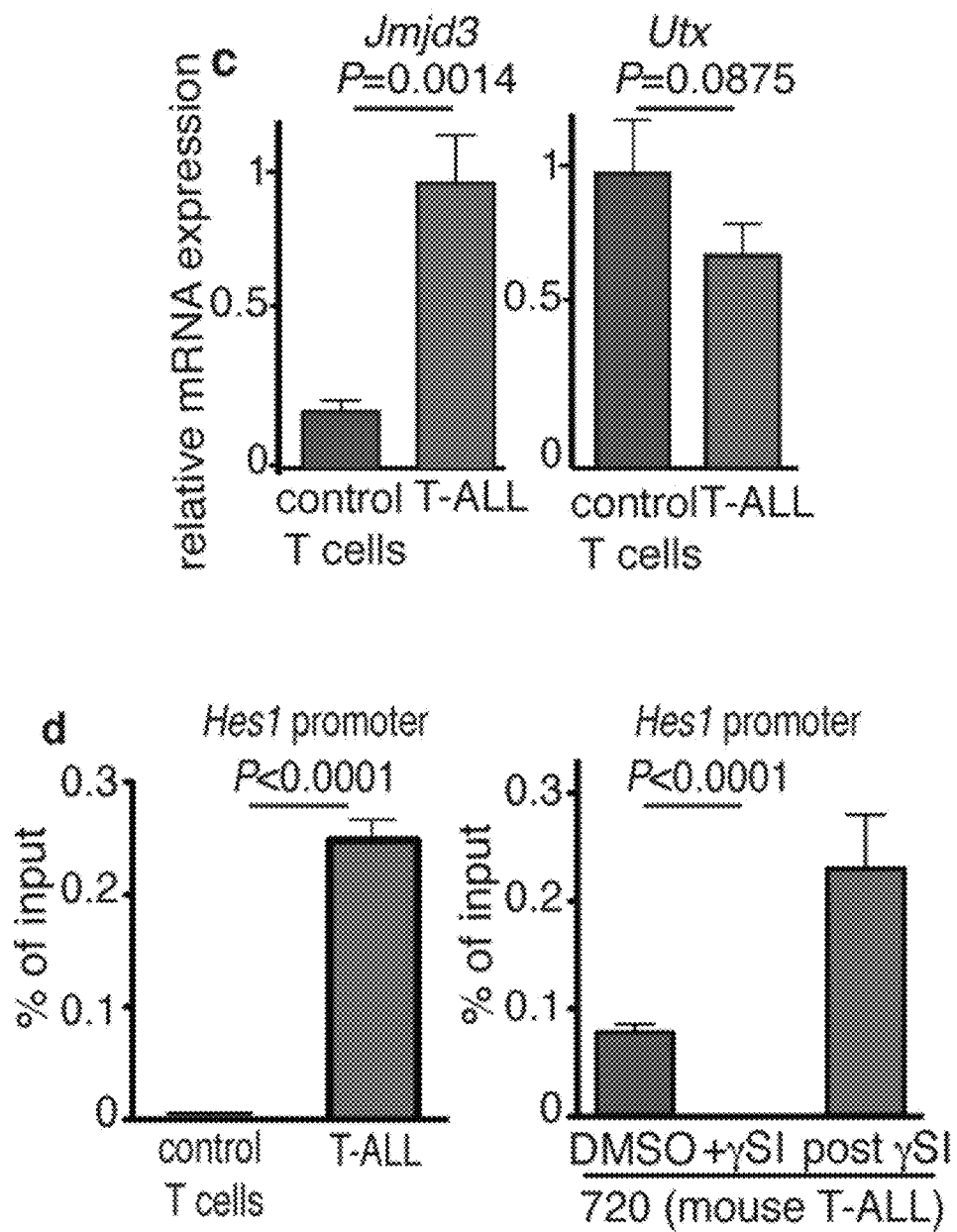
Figures 1E, 1F:
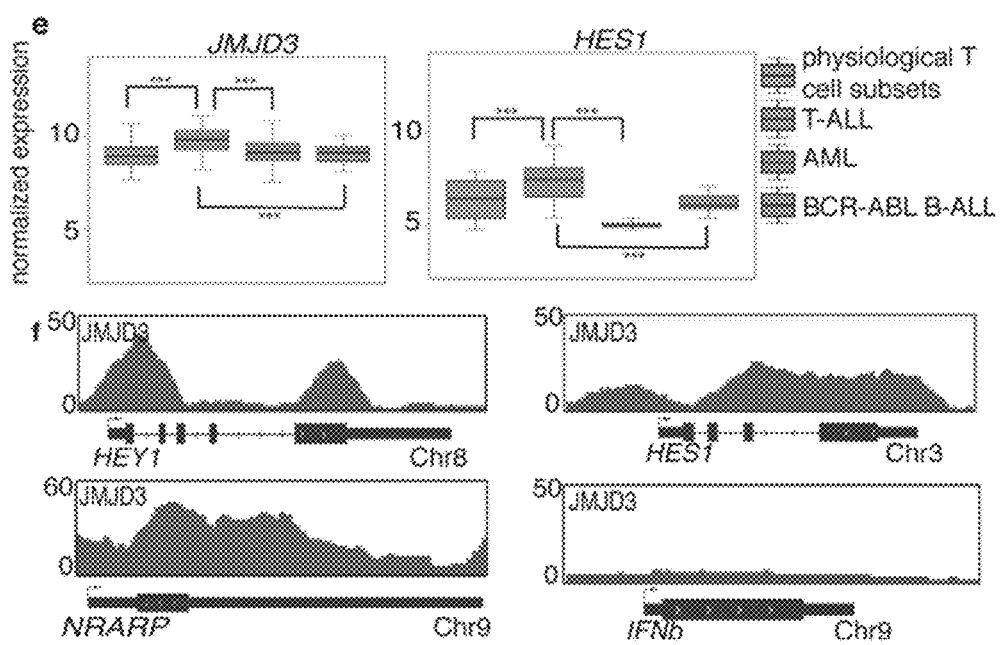

Processed T-ALL and B-ALL patient microarray expression data were downloaded from Zhang et al., "The Genetic Basis of Early T-cell Precursor Acute Lymphoblastic Leukaemia," *Nature* 481:157-163 (2012), which is hereby incorporated by reference in its entirety (GEO accession GSE33315), physiological T-cell expression data from Dik et al., "New Insights on Human T Cell Development by Quantitative T Cell Receptor Gene Rearrangement Studies and Gene Expression Profiling," *J. Exp. Med.* 201:1715-1723 (2005), which is hereby incorporated by reference in its entirety (GEO accession G5E22601) and acute myeloid leukaemia (AML) expression data from Verhaak et al., "Prediction of Molecular Subtypes in Acute Myeloid Leukemia Based on Gene Expression Profiling," *Haematologica* 94:131-134 (2009), which is hereby incorporated by reference in its entirety (GEO accession G5E6891). Data were first converted to the logarithmic scale when necessary and then quantile-normalized across samples. The Wilcoxon two-sided unpaired test per gene probe was used to determine significant differences between sample categories (T-ALL, B-ALL, AML and physiological T cells; FIG. 1E). A gene was considered significantly overexpressed in T-ALL compared with the rest of the sample categories if at least one of its associated probes was significantly overexpressed in T-ALL according to the statistical test.

Figures 2A, 2B:
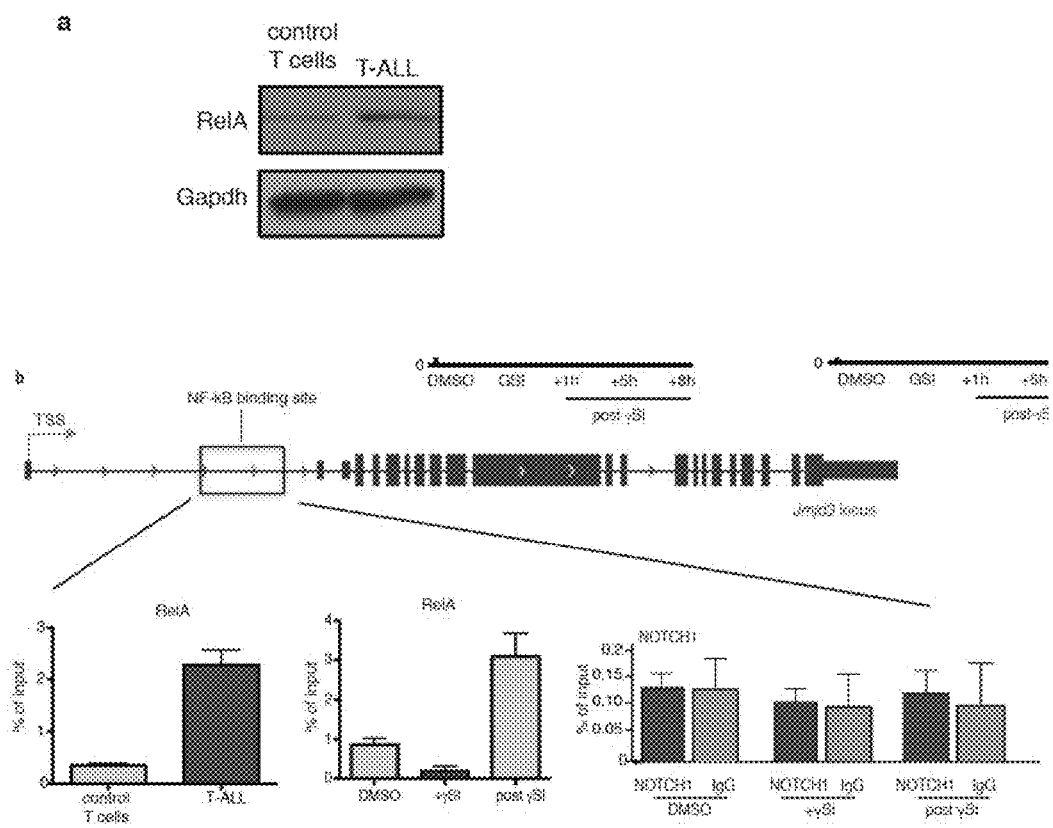
FIGS. 2A-2K show JMJD3 is induced through activation of the NF-κB pathway in a NOTCH1-dependent mode in T-ALL and binds to NOTCH1 target genes.
Figure 2C:
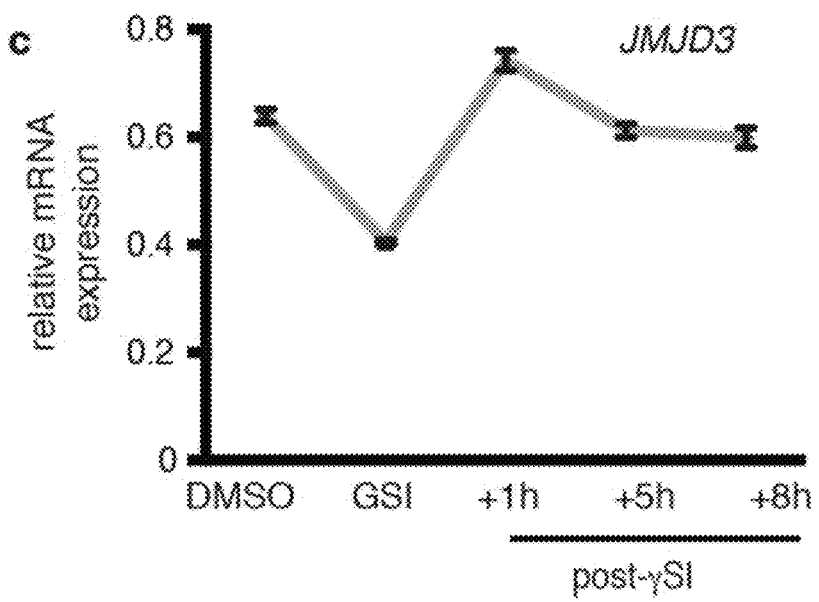
Figure 2C:
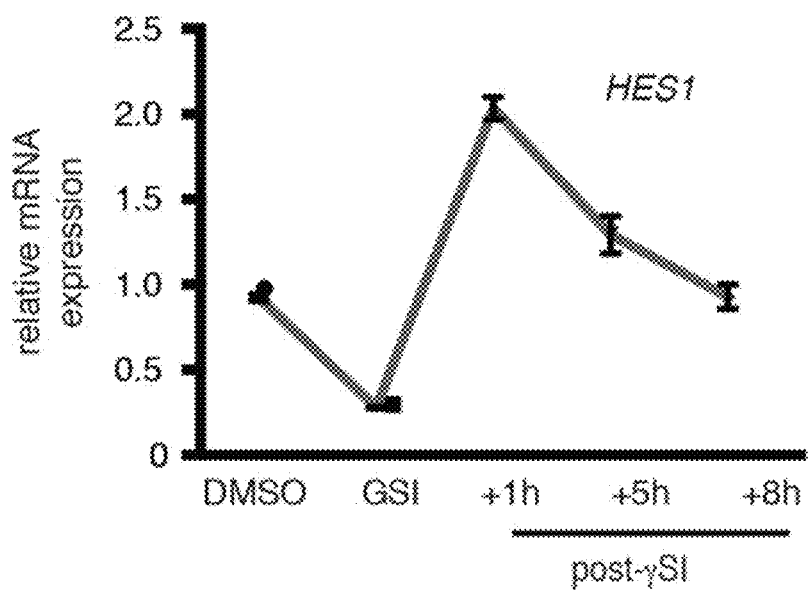
Figures 2D, 2E, 2F, 2G:
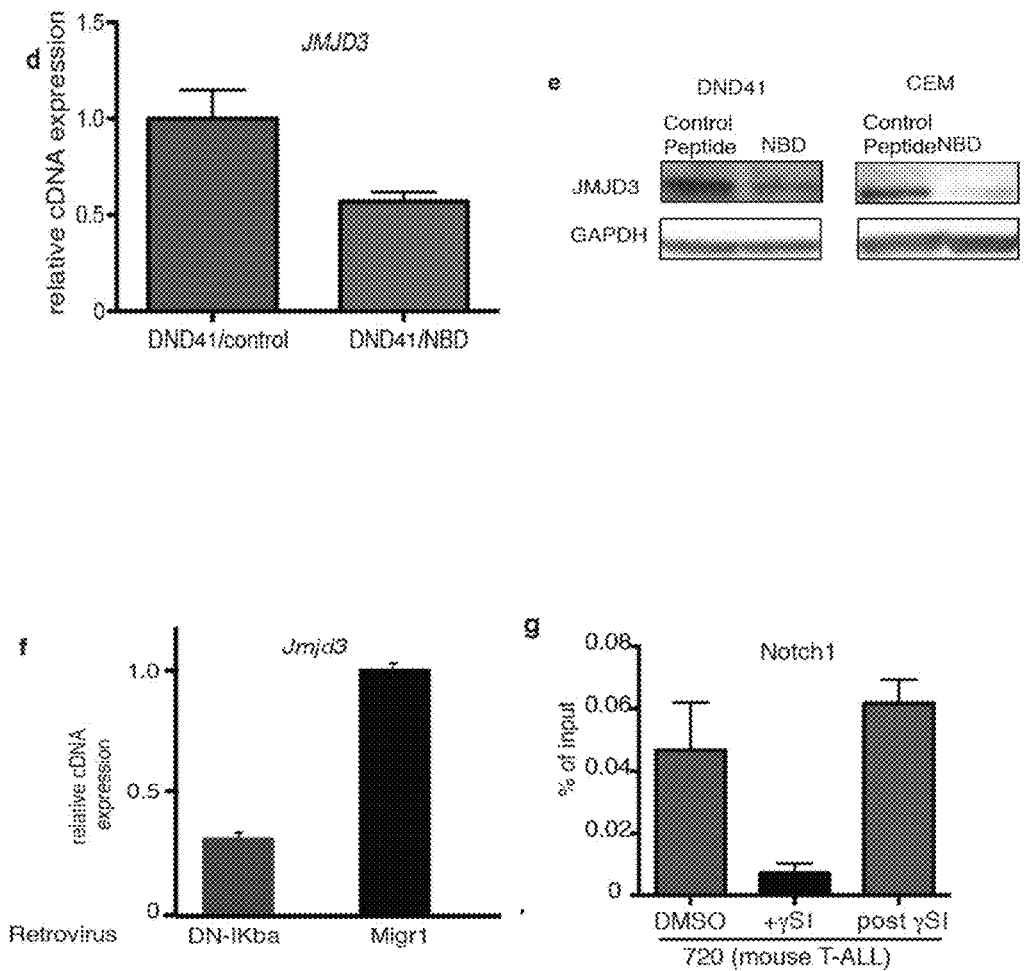
Figure 2H:
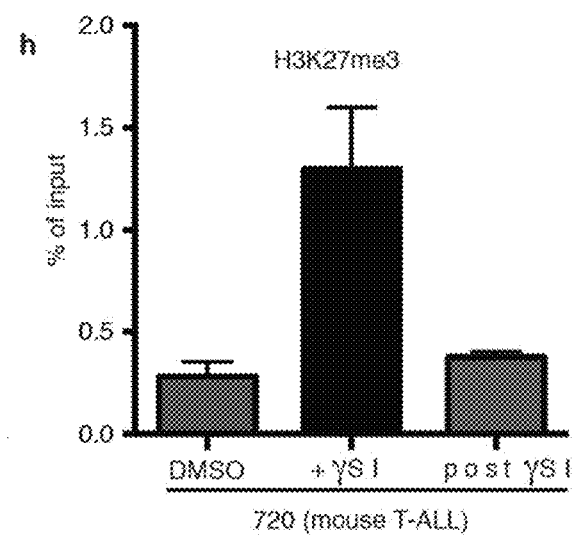
Figure 2I:
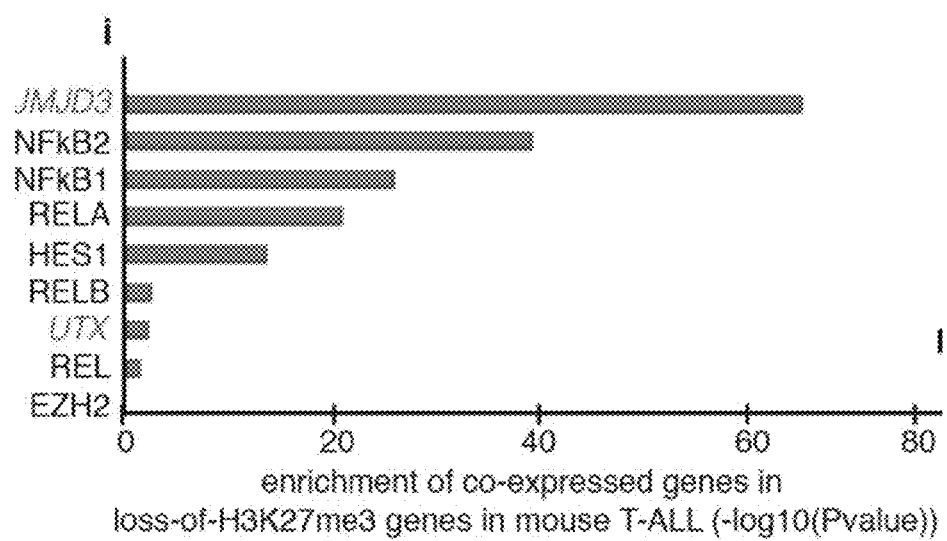

Genes experiencing loss of H3K27me3 at TSSs in the mouse NOTCH-IC model compared with normal double-positive (DP) mouse cells were obtained from a previous study (Ntziachristos et al., "Genetic Inactivation of the Polycomb Repressive Complex 2 in T Cell Acute Lymphoblastic Leukemia," *Nature Med.* 18:298-303 (2012), which is hereby incorporated by reference in its entirety). Enrichment of human homologues of these genes in JMJD3-correlating genes in the patient data described above was estimated as follows. First, Pearson's correlation of JMJD3 expression (separately for each JMJD3 probe) against expression of each gene was computed. Then, the distribution of the correlations of the genes losing H3K27me3 (human homologues of the mouse genes) was compared with that of the genes that did not lose H3K27me3, using Student's t-test (separately for each JMJD3probe, minimum P value shown in the corresponding figure (FIG. 1F)) or the Wilcoxon one-sided unpaired test, yielding similar results. This analysis was repeated for NF-κB1, NF-κB2, REL, RELA, RELB, HES1, UTX and EZH2 (FIG. 2I).

JMJD3 Peak Identification, Characterization and Overlap with Published Data Sets.

JMJD3 ChIP-seq reads were aligned using Bowtie (with default parameters, except for m 1 so as to report only unique alignments) on human assembly version hg19. Peak discovery was performed with MACS (version 2.0.10) using default parameters, except for using a fragment size of 300 base pairs as estimated with the Agilent 2100 Bioanalyzer. Sonicated input was used as a control for peak discovery. Then, the IDR method (Li et al., "Measuring Reproducibility of Highthroughput Experiments," *Ann. Appl. Stat.* 5:1752-1779 (2011), which is hereby incorporated by reference in its entirety) was used, guidelines and pipeline available for narrow peaks at the URL https://sites.google.com/site/anshulkundaje/projects/idr to determine highly reproducible peaks supported by both JMJD3 replicates.

JMJD3 peaks were characterized according to their genome-wide distribution (FIG. 2K) into the following groups: (a) 1-kilobase (kb) TSS-flanking regions of transcript isoforms; (b) gene body regions (excluding any regions overlapping with (a)); and (c) upstream regions of a minimum of 10 kb and a maximum of 100 kb (excluding any regions overlapping with (a) or (b)).

Figure 2J:
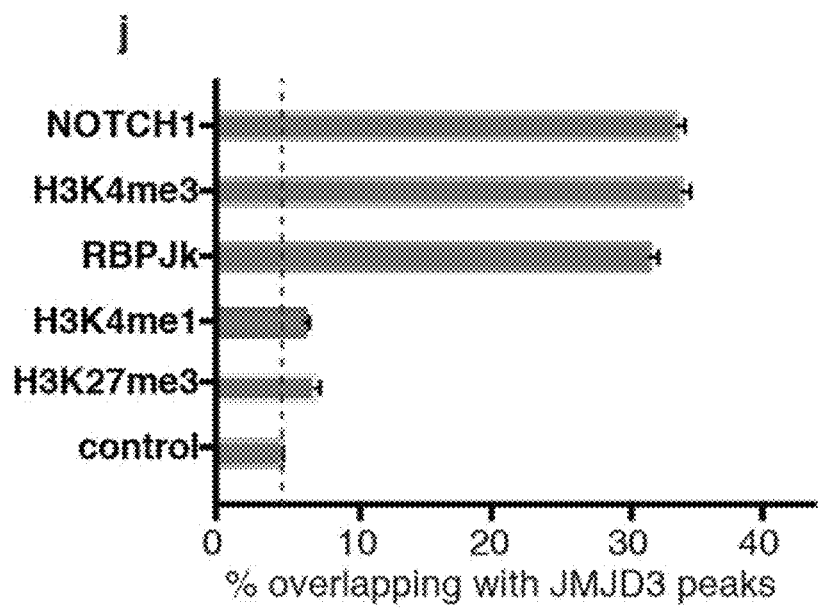
Figure 2K:
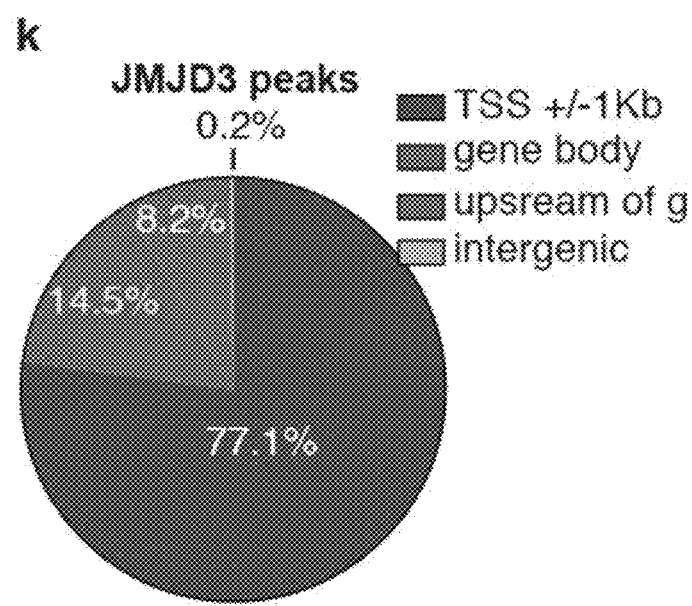

Co-occurrence of JMJD3 peaks with H3K4me3, H3K27me3, NOTCH1 and RBP-J was computed as the percentage of such peaks (5,000 top-scoring peaks for each protein obtained from Wang et al., "Genome-Wide Analysis Reveals Conserved and Divergent Features of Notch1/RBPJ Binding in Human and Murine T-Lymphoblastic Leukemia Cells," *Proc. Natl. Acad. Sci. USA* 108:14908-14913 (2011), which is hereby incorporated by reference in its entirety; GEO accession GSE29600) that have some overlap with a JMJD3 peak. The statistical significance of these overlaps was determined using random resampling simulation (for example, H3K4me3 peaks were randomly redistributed along the genome). As a control, the percentage of TSSs that have JMJD3 peaks (this is a rather conservative control since genome-wide JMJD3 occupancy is much lower, as a result of JMJD3 being concentrated in TSSs) was used, and compared with this control, an 7-fold enrichment of H3K4me3JMJD3 was obtained (P<0.001 as determined by the random resampling scheme). Similar enrichments were obtained for NOTCH1JMJD3 and RBP-JJMJD3 co-occurrence, whereas no significant enrichment was observed for H3K27me3-silenced or H3K4me1 enhancer-related regions (FIG. 2J).

RNA-seq Analysis.

Differential gene expression analysis was performed for each matched knockdown versus control pair, separately in each biological or technical replicate in each of two cell lines (CUTLL1 and CEM). Three types of comparisons were tested: (1) JMJD3 knockdown versus Renilla; (2) JMJD3 knockdown versus UTX knockdown; and (3) UTX knockdown versus Renilla. DEGseq44 was used to analyze (a) matched knockdown—Renilla replicates in separate DEGseq runs and (b) all replicates on a combined DEGexp run. For the mouse (Utx knockout) samples, spleen and bone marrow from a wild-type male (referred to as animal #9), as well as spleen from a wild-type female (animal #10), were compared with spleen and bone marrow from a knockout male (#23) and spleen from another knockout male (#27) (see also the GEO accession G5E56696). For illustration, scatter plots (FIG. 4D and FIGS. 5G-I) were created using values obtained from DEGseq analysis of merged biological and/or technical replicates. Gene RNA-seq FPKM values were computed using GenomicTools (Tsirigos et al., "GenomicTools: A Computational Platform for Developing High-Throughput Analytics in Genomics," *Bioinformatics* 28:282-283 (2012), which is hereby incorporated by reference in its entirety). The P-value cutoff for differential expression was set at $1 \times 10^{-5}$, with the minimum absolute $\log_2$ fold change set at 0.5. However, all key results in this study (that is, the significance of the overlaps of the various gene expression signatures demonstrating the contrasting roles of JMJD3 and UTX) are robust to changes in these two parameters.

The P value of a gene set of size t (for example, GSKJ4-downregulated genes) containing k genes with a specific attribute (for example, shJMJD3-mediated downregulation or UTX knockout upregulation) was determined against the null hypothesis that k or more such genes could have been observed merely by chance in an equal sized gene set that was randomly drawn from the entire reference set of genes of size N (that is, all downregulated, upregulated and constant genes). This P value was obtained by using the hypergeometric cumulative distribution with parameters N, t, k and n, where n is the number of genes possessing the attribute in the entire reference gene set of size N.

H3K27me3 Gain and Loss Analysis.

JMJD3-affected (upregulated or downregulated) genes were defined as genes whose expression was significantly differentially expressed in IMID3 knockdown cells compared with both Renilla and UTX knockdown cells. Changes in JMJD3 binding and the H3K27me3 mark around gene TSSs between cells treated with the inhibitor GSKJ4 and the control GSKJ5 were determined using Genomic Tools ("genomic_apps peak cliff" tool) as described in a previously published study (Ntziachristos et al., "Genetic Inactivation of the Polycomb Repressive Complex 2 in T Cell Acute Lymphoblastic Leukemia," *Nature Med.* 18:298-303 (2012), which is hereby incorporated by reference in its entirety). Epigenetic changes between the treatment (shJMJD3 or GSKJ4) and control samples were determined by evaluating sliding windows across the genome using the following protocol. First, enriched ChIP-seq windows were identified separately for each of the two samples under comparison using a window-based approach and the binomial probability distribution to compare signal reads with control reads in each window. Subsequently, for each genomic window enriched in at least one of the two samples, the total number of reads was determined, and the window read counts were normalized using quantile normalization across biological replicates and samples before comparison. Finally, for each window, the fold change between the two samples was calculated (GSKJ4 versus control and vice versa). To estimate the false discovery rate, the distribution of the observed H3K27me3 fold changes was compared with the distribution of fold changes between replicates of the same treatment. This comparison was performed independently at different H3K27me3 read density levels to control for artificially high fold changes due to low read counts in the denominator. Significant epigenetic changes are reported at 5% false discovery.

JMJD3, NOTCH1, H3K4me3 and H3K27me3 heatmaps were generated using GenomicTools ("genomic_apps heatmap" utility) over log-transformed read counts in 200-nucleotide non-overlapping bins of 4-kb-flanked TSSs. Box plots of H3K27 me3 $\log_2$[fold changes] (GSKJ4 versus control) show the distribution of values in (a) JMJD3 targets, (b) commonly downregulated genes upon shJMJD3 and GSKJ4 treatment, and (c) the intersection of GSKJ4-upregulated and shJMJD3-upregulated genes as a negative control. P values were computed using a one-sided Wilcoxon unpaired test for (a) and (b) versus the control (c).

RNA-seq and ChIP-seq Replicate Reproducibility.

For RNA-seq experiments, n the reproducibility of gene expression levels as measured by FPKM values was focused on. For each pair of replicates, the Spearman and Pearson correlations were computed, as well as the Pearson correlation on log-transformed FPKM values. In general, Pearson correlations were much higher because higher values are dominant, and highly expressed genes tend to be more reproducible. Using a Pearson correlation on log transformed values attempts to balance the expression distribution and allow contributions from genes that are expressed at a lower level, thereby providing a more realistic genome-wide reproducibility metric. Spearman correlations focus on the ranking of gene expression, and in the experiments, in general, were a more conservative (that is, lower) and consistent (lower variability across various settings, and when comparing different cell lines (that is, CUTLL1 and CEM)) estimate of reproducibility; therefore, for simplicity, only the Spearman correlations have been reported.

For ChIP-seq 'broad peak' experiments (H3K27me3), Pearson, log transformed Pearson and Spearman correlations were also used on (a) TSSs and (b) all genome-wide peaks. As before, Spearman correlation was the most conservative and consistent estimate of reproducibility.

For ChIP-seq 'narrow peak' experiments (JMJD3), in addition to TSS-based and genome-based correlations, the IDR method (Li et al., "Measuring Reproducibility of High-throughput Experiments," *Ann. Appl. Stat.* 5:1752-1779 (2011), which is hereby incorporated by reference in its entirety) was used. Apart from determining the reproducibility the IDR method was also used to determine high-confidence peaks supported by both JMJD3 replicates.

Example 1

JMJD3 is Highly Expressed in T-ALL and Controls the Expression of Important Oncogenic Factors In recent studies, researchers have revealed that PRC2 has a key tumour-suppressor function, catalyzing the methylation of H3K27 (Zhang et al., "The Genetic Basis of Early T-cell Precursor Acute Lymphoblastic Leukaemia," *Nature* 481:157-163 (2012); Ntziachristos et al., "Genetic Inactivation of the Polycomb Repressive Complex 2 in T Cell Acute Lymphoblastic Leukemia," *Nature Med.* 18:298-303 (2012); Simon et al., "A Key Role for EZH2 and Associated Genes in Mouse and Human Adult T-Cell Acute Leukemia," *Genes Dev.* 26:651-656 (2012), which are hereby incorporated by reference in their entirety). Since net H3K27me3 levels are dictated by the balance between histone methylation and active histone demethylation, it was hypothesized that the removal of methyl groups from H3K27 is also an important process in T-ALL progression. The possible roles of H3K27 demethylases in T-ALL were therefore investigated. Ubiquitously transcribed tetratricopeptide repeat X-linked protein (UTX) (Hubner & Spector, "Role of H3K27 Demethylases Jmjd3 and UTX in Transcriptional Regulation," *Cold Spring Harb. Symp. Quant. Biol.* 75:43-49 (2010); Kooistra & Helin, "Molecular Mechanisms and Potential Functions of Histone Demethylases," *Nature Rev. Mol. Cell Biol.* 13:297-311(2012), which are hereby incorporated by reference in their entirety) (also known as KDM6A) is a ubiquitously expressed protein that controls the basal levels of H3K27me3 and the induction of ectoderm and mesoderm differentiation (Morales et al., "Utx Is Required for Proper Induction of Ectoderm and Mesoderm During Differentiation of Embryonic Stem Cells," *PLoS One* 8:e60020 (2013); Wang et al., "UTX Regulates Mesoderm Differentiation of Embryonic Stem Cells Independent of H3K27 Demethylase Activity," *Proc. Natl. Acad. Sci. USA* 109:15324-15329 (2012), which are hereby incorporated by reference in their entirety) and is essential for somatic cell reprogramming (Mansour et al., "The H3K27 Demethylase Utx Regulates Somatic and Germ Cell Epigenetic Reprogramming," *Nature* 488:409-413 (2012), which is hereby incorporated by reference in its entirety). Jumonji D3 (JMJD3) (Hubner & Spector, "Role of H3K27 Demethylases Jmjd3 and UTX in Transcriptional Regulation," *Cold Spring Harb. Symp. Quant. Biol.* 75:43-49 (2010); Kooistra & Helin, "Molecular Mechanisms and Potential Functions of Histone Demethylases," *Nature Rev. Mol. Cell Biol.* 13:297-311(2012), which are hereby incorporated by reference in their entirety) (also known as KDM6B) is induced upon inflammation (De Santa et al., "The Histone H3 Lysine-27 DemethylaseJmjd3 Links Inflammation to Inhibition of Polycomb-Mediated Gene Silencing," *Cell* 130:1083-1094 (2007), which is hereby incorporated by reference in its entirety) or exposure to viral and oncogenic stimuli (Agger et al., "The H3K27me3 Demethylase JMJD3 Contributes to the Activation of the INK4AARF Locus in Response to Oncogene- and Stress-Induced Senescence," *Genes Dev.* 23:1171-1176 (2009); Barradas et al., "Histone Demethylase JMJD3 Contributes to Epigenetic Control of INK4a/ARF by Oncogenic RAS," *Genes Dev.* 23:1177-1182 (2009), which are hereby incorporated by reference in their entirety), and it controls neuronal and epidermal differentiation (Jepsen et al., "SMRT-Mediated Repression of an H3K27 Demethylase in Progression From Neural Stem Cell to Neuron," *Nature* 450:415-419 (2007); Sen et al., "Control of Differentiation in a Self-Renewing Mammalian Tissue by the Histone Demethylase JMJD3," *Genes Dev.* 22:1865-1870 (2008), which are hereby incorporated by reference in their entirety) and inhibits reprogramming (Zhao et al., "Jmjd3 Inhibits Reprogramming by Upregulating Expression of INK4a/Arf and Targeting PHF20 for Ubiquitination," *Cell* 152:1037-1050 (2013), which is hereby incorporated by reference in its entirety). UTX is a tumour suppressor in several solid tumours (Jankowska et al., "Mutational Spectrum Analysis of Chronic Myelomonocytic Leukemia Includes Genes Associated with Epigenetic Regulation: UTX, EZH2, and DNMT3A." *Blood* 118:3932-3941(2011); Wang et al., "The Histone Demethylase UTX Enables RB-Dependent Cell Fate Control," *Genes Dev.* 24:327-332 (2010); Thieme et al., "The Histone Demethylase UTX Regulates Stem Cell Migration and Hematopoiesis," *Blood* 121:2462-2473 (2013); van Haaften et al., "Somatic Mutations of the Histone H3K27 Demethylase Gene UTX in Human Cancer," *Nature Genet.* 41:521-523 (2009); Mar et al., "Sequencing Histone-Modifying Enzymes Identifies UTX Mutations in Acute Lymphoblastic Leukemia," *Leukemia* 26:1881-1883 (2012), which are hereby incorporated by reference in their entirety). However, the roles of these two demethylases as direct modulators of the oncogenic state are largely uncharacterized (Agger et al., "The H3K27me3 Demethylase JMJD3 Contributes to the Activation of the INK4AARF Locus in Response to Oncogene- and Stress-Induced Senescence," *Genes Dev.* 23:1171-1176 (2009); Barradas et al., "Histone Demethylase JMJD3 Contributes to Epigenetic Control of INK4a/ARF by Oncogenic RAS," *Genes Dev.* 23:1177-1182 (2009), which is hereby incorporated by reference in its entirety).

NOTCH1-induced T-ALL animal models 4 (FIG. 1A) have been generated and studied, because activating mutations of NOTCH1 are a defining feature of T-ALL (Weng et al., "Activating Mutations of NOTCH1 in Human T Cell Acute Lymphoblastic Leukemia," *Science* 306:269-271 (2004), which is hereby incorporated by reference in its entirety). Jmjd3 messenger RNA and protein expression levels were significantly higher in leukaemic cells than in untransformed CD4$^+$CD8$^+$ (double positive) control T cells, which exhibit low levels of active NOTCH1, whereas Utx (and Ezh2) (Ntziachristos et al., "Genetic Inactivation of the Polycomb Repressive Complex 2 in T Cell Acute Lymphoblastic Leukemia," *Nature Med.* 18:298-303 (2012), which is hereby incorporated by reference in its entirety) expression did not change significantly (FIG. 1B, FIG. 1C and Table 1) upon transformation.

TABLE 1

Primer Sets

| | Sequence |
|---|---|
| mouse cDNA primers | |
| Utx-F | TCCAAGACCACCATCCTCAC (SEQ ID NO: 7) |
| Utx-R | GGAGGAAAGAAAGCATCACG (SEQ ID NO: 8) |
| Jmjd3-F | ACGAGCCTGCCTACTACTGC (SEQ ID NO: 9) |
| Jmjd3-R | CTCGCAGTGCACCAGGTA (SEQ ID NO: 10) |
| Hes1-F | GCGAAGGGCAAGAATAAATG (SEQ ID NO: 11) |
| Hes1-R | TGTCTGCCTTCTCTAGCTTGG (SEQ ID NO: 12) |
| Il17ra-F | CATTTCACTCGTAAAAGAGCCC (SEQ ID NO: 13) |
| Il17ra-R | TGGAAGTGGATGGAAGTCAA (SEQ ID NO: 14) |
| Suz12-F | TGATGGCTTATCATTTTTGTGG (SEQ ID NO: 15) |
| Suz12-R | GAGAAAATGAAAGGAGAGCAAGA (SEQ ID NO: 16) |
| Mouse ChIP primers | |
| Hes1 promoter-F | AAGTTTCACACGAGCCGTTC (SEQ ID NO: 17) |
| Hes1 promoter-R | TGTTATCAGCACCAGCTCCA (SEQ ID NO: 18) |
| Jmjd3 promoter-F | CGCAGCTTCCCAGAAGTTAG (SEQ ID NO: 19) |
| Jmjd3 promoter-R | ACCAAGTTCCTCCAGCTCCT (SEQ ID NO: 20) |
| Human cDNA primers | |
| NRARP-F | CGCTGTTGCTGGTGTTCTAA (SEQ ID NO: 21) |
| NRARP-R | CATTGACCACGCAGTGTTTT (SEQ ID NO: 22) |

TABLE 1-continued

Primer Sets

| | Sequence |
|---|---|
| NOTCH1-F | CGGGGCTAACAAAGATATGC (SEQ ID NO: 23) |
| NOTCH1-R | AGTGGTCCAGCAGCACCTT (SEQ ID NO: 24) |
| MYC-F | GCTGCTTAGACGCTGGATTT (SEQ ID NO: 25) |
| MYC-R | CGAGGTCATAGTTCCTGTTGG (SEQ ID NO: 26) |
| MAZ-F | GACCACATGAAGGTGCACAG (SEQ ID NO: 27) |
| MAZ-R | GTCCTTCACCGCGTGGAT (SEQ ID NO: 28) |
| HEY1-F | ATTTTGGCCAGAAAAAGACG (SEQ ID NO: 29) |
| HEY1-R | CTGGGTACCAGCCTTCTCAG (SEQ ID NO: 30) |
| JMJD3-F | GGGAAGAAAATCGCTTACCAG (SEQ ID NO: 31) |
| JMJD3-R | TCACTTGTCACGAACAGGATG (SEQ ID NO: 32) |
| UTX-F | ACTTGGAAAACTTTGTGGTGCT (SEQ ID NO: 33) |
| UTX-R | CAAGATGAGGCGGATGGTA (SEQ ID NO: 34) |

Human ChIP primers

| | |
|---|---|
| NRARP locus-F | ACCAACTGCGAGTTCAACG (SEQ ID NO: 35) |
| NRARP locus-R | TTGACCAGCAGCTTCACG (SEQ ID NO: 36) |
| NOTCH1 locus-1F | CAGACACTTTGAAGCCCTCAG (SEQ ID NO: 37) |
| NOTCH1 locus-1R | CGCCTTTGTGCTTCTGTTCT (SEQ ID NO: 38) |
| NOTCH1 locus-2F | CCTCCTCTTCCTCGCTGTT (SEQ ID NO: 39) |
| NOTCH1 locus-2R | CAGACTGAGCACCCGTCTCT (SEQ ID NO: 40) |
| NOTCH1 locus-3F | AGGCTGGCAGCTCTATTCAG (SEQ ID NO: 41) |
| NOTCH1 locus-3R | CGTGGCAGAGTCTGGAAAGT (SEQ ID NO: 42) |
| MYC locus 1F | GGTCGGACATTCCTGCTTTA (SEQ ID NO: 43) |
| MYC locus 1R | CAAGGAGCTCAGGATGCAA (SEQ ID NO: 44) |
| MAZ locus 1F | GTCTCCCTCCCTCCTGTGTT (SEQ ID NO: 45) |
| MAZ locus 1R | AAATTTGAAAAGGCGGAGTG (SEQ ID NO: 46) |
| MAZ locus 2F | ATCTTCGGGGAACGACTCA (SEQ ID NO: 47) |
| MAZ locus 2R | CTTCGGCTTCCGCTTTTT (SEQ ID NO: 48) |
| HEY1 locus-F | TGGGGACATGGAACCTAGAG (SEQ ID NO: 49) |
| HEY1 locus-R | GCGACCTCTCAGATCACCTC (SEQ ID NO: 50) |
| RBBP6 locus-1F | TATGGTGCTGGTGGCTGTTA (SEQ ID NO: 51) |
| RBBP6 locus-1R | GCTGCTGCTTCCAATAAACTG (SEQ ID NO: 52) |
| RBBP6 locus-2F | TGAGCCTGGCAATGTTGTTA (SEQ ID NO: 53) |
| RBBP6 locus-2R | CCGCTGCCAAGAACTGATA (SEQ ID NO: 54) |
| JMJD3 locus (NFkB binding) 2.1AF | GTGGGCTGAGGAGTTGTGTC (SEQ ID NO: 55) |
| JMJD3 locus (NFkB binding) 2.1AR | CCAGAAAACCTTCCCCTCTT (SEQ ID NO: 56) |
| JMJD3 locus (NFkB binding) 2.1BF | GTGGGCTGAGGAGTTGTGTC (SEQ ID NO: 57) |
| JMJD3 locus (NFkB binding) 2.1BR | CGTGAGTCACCCAGAAAACC (SEQ ID NO: 58) |

It has previously been shown that the transcription factor nuclear factor-kB (NF-κB) controls JMJD3 expression during inflammation (De Santa et al., "The Histone H3 Lysine-27 DemethylaseJmjd3 Links Inflammation to Inhibition of Polycomb-Mediated Gene Silencing," Cell 130:1083-1094 (2007), which is hereby incorporated by reference in its entirety) and that NOTCH1 induces the NF-κB pathway in T-ALL (Espinosa et al., "The Notch/Hes1 Pathway Sustains NF-κB Activation Through CYLD Repression in T Cell Leukemia," Cancer Cell 18:268-281 (2010), which is hereby incorporated by reference in its entirety). Here increased expression of the p65 subunit (also known as RELA) of NF-κB and its—but not NOTCH1—binding to Jmjd3 control elements in mouse T-ALL cells is shown (FIGS. 2A-2B). Modulation of the levels of intracellular NOTCH1 or the activity of the NF-κB pathway significantly decreased the amount of NF-κB bound to the Jmjd3 elements, as well as Jmjd3 mRNA expression (FIGS. 2B-2F). JMJD3 binding to specific oncogenic loci was then probed, which has previously been shown to be important in T-ALL (Ntziachristos et al., "Genetic Inactivation of the Polycomb Repressive Complex 2 in T Cell Acute Lymphoblastic Leukemia," Nature Med. 18:298-303 (2012), which is hereby incorporated by reference in its entirety). It was found that JMJD3 binding was highly enriched on the Hes1 promoter (FIG. 1D, left), and this binding depended on the activation of the NOTCH1 pathway and negatively correlated with the H3K27me3 levels (FIGS. 2G-2H).

Analyses of human leukemia cases (Zhang et al., "The Genetic Basis of Early T-cell Precursor Acute Lymphoblastic Leukaemia," Nature 481:157-163 (2012); Dik et al., "New Insights on Human T Cell Development by Quantitative T Cell Receptor Gene Rearrangement Studies and Gene Expression Profiling," J. Exp. Med. 201:1715-1723 (2005); Van Vlierberghe et al., "ETV6 Mutations in Early Immature Human T Cell Leukemias," J. Exp. Med. 208: 2571-2579 (2011); Valk et al., "Prognostically Useful Gene-Expression Profiles in Acute Myeloid Leukemia," N. Engl. J. Med. 350:1617-1628 (2004), which are hereby incorporated by reference in their entirety) have shown that JMJD3 is more highly expressed in T-ALL cells than in normal T-cell progenitors (Dik et al., "New Insights on Human T Cell Development by Quantitative T Cell Receptor Gene Rearrangement Studies and Gene Expression Profiling," J. Exp. Med. 201:1715-1723 (2005), which is hereby incorporated by reference in its entirety) or in other types of leukemia (Van Vlierberghe et al., "ETV6 Mutations in Early Immature Human T Cell Leukemias," J. Exp. Med. 208: 2571-2579 (2011); Valk et al., "Prognostically Useful Gene-Expression Profiles in Acute Myeloid Leukemia," N. Engl.

J. Med. 350:1617-1628 (2004), which are hereby incorporated by reference in their entirety), which is similar to the expression of the classic NOTCH1 target HES1 (FIG. 1E). Genes that are co-expressed with JMJD3 in human primary samples were found to exhibit loss of H3K27me3 during leukemia progression (FIG. 2I), suggesting a connection between the expression of JMJD3 and the H3K27me3 levels on specific targets.

Chromatin immunoprecipitation followed by sequencing (ChIP-seq) studies in human T-ALL cells (the cell line CUTTL1) showed that JMJD3 was bound to important NOTCH1 targets with oncogenic functions (such as HEYI, NRARP and HES1) (FIG. 1F). There was a significant co-occupancy of JMJD3 with NOTCH1 (Wang et al., "Genome-Wide Analysis Reveals Conserved and Divergent Features of Notch1/RBPJ Binding in Human and Murine T-Lymphoblastic Leukemia Cells," Proc. Natl. Acad. Sci. USA 108:14908-14913 (2011), which is hereby incorporated by reference in its entirety) (33% of the top JMJD3 peaks were occupied by NOTCH1, a 6.9-fold enrichment over control, $P<1\times10^{-3}$), the NOTCH1 partner RBP-Jk and the activating mark H3K4me3 (Wang et al., "Genome-Wide Analysis Reveals Conserved and Divergent Features of Notch1/RBPJ Binding in Human and Murine T-Lymphoblastic Leukemia Cells," Proc. Natl. Acad. Sci. USA 108: 14908-14913 (2011), which is hereby incorporated by reference in its entirety) (FIG. 2J). The majority of JMJD3 binding sites were localized around the transcription start sites (TSSs) of genes (FIG. 2K) in a fashion similar to NOTCH1 binding sites (Wang et al., "Genome-Wide Analysis Reveals Conserved and Divergent Features of Notch1/RBPJ Binding in Human and Murine T-Lymphoblastic Leukemia Cells," Proc. Natl. Acad. Sci. USA 108:14908-14913 (2011), which is hereby incorporated by reference in its entirety). These results suggest a key role for JMJD3 in oncogenic programs in T-ALL, through interaction with NOTCH1.

Example 2

Dissecting the Oncogenic Role of JMJD3 in T-ALL

Figures 3A, 3B, 3C:
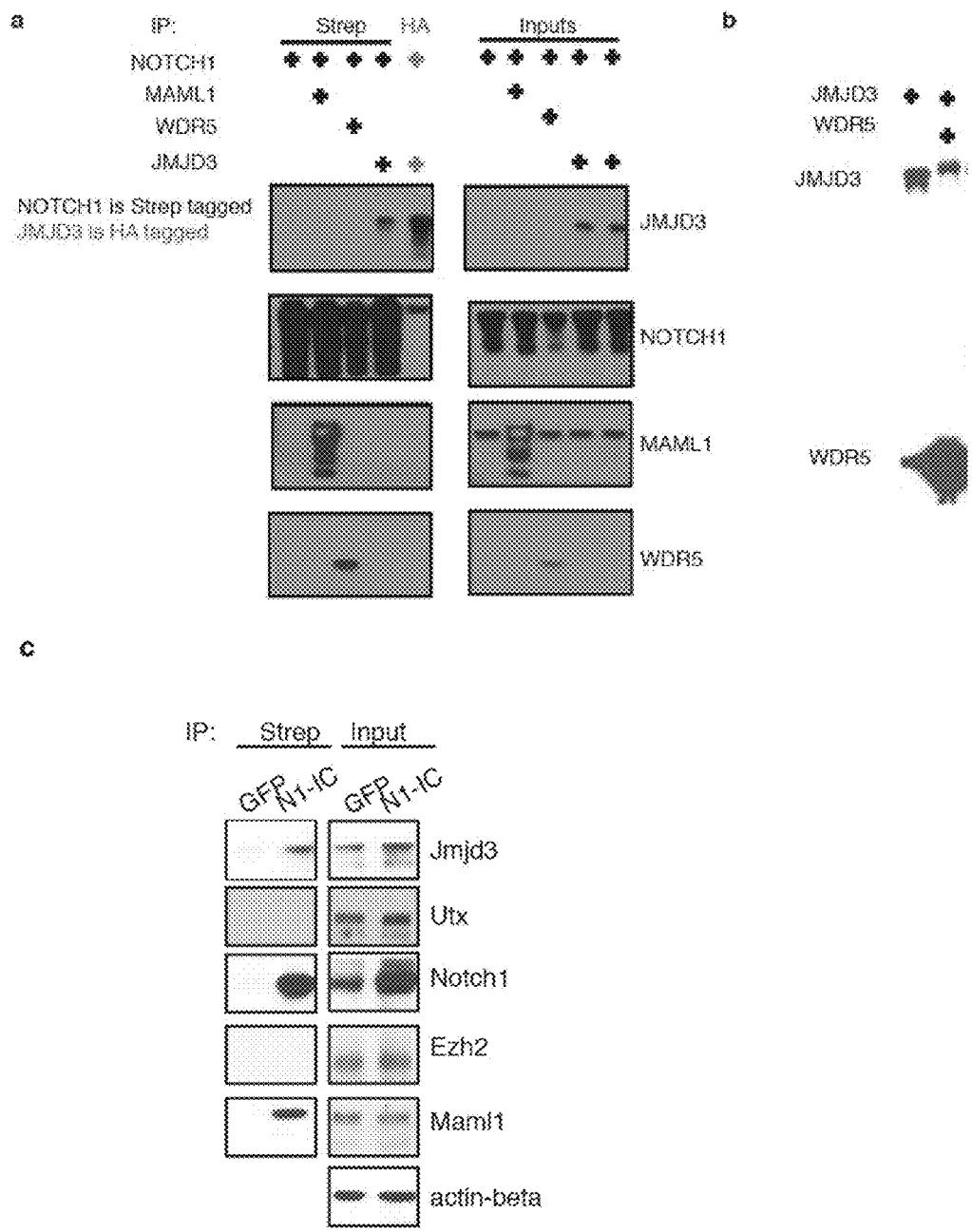
FIGS. 3A-3F show JMJD3 is vital for T-ALL growth through participation in NOTCH1 transcriptional programs.

Protein immunoprecipitation studies in 293T cells (human embryonic kidney cells), as well as in mouse T-ALL cell lines, showed that JMJD3 is part of the NOTCH1 transcriptional complex, as it interacts directly with NOTCH1 and MAML1 (FIGS. 3A-3C). By contrast, there was no NOTCH1 interaction with EZH2 or UTX. As JMJD3 has been shown to be a member of MLL complexes (De Santa et al., "The Histone H3 Lysine-27 Demethylase Jmjd3 Links Inflammation to Inhibition of Polycomb-Mediated Gene Silencing," Cell 130:1083-1094 (2007), which is hereby incorporated by reference in its entirety), whether JMJD3 interacted with WDR5, a key subunit of the MLL complex, was tested. It was found that JMJD3 interacted with WDR5 (FIG. 3B), suggesting a potential NOTCH1JMJD3MLL complex on target promoters.

Figures 3D, 3E:
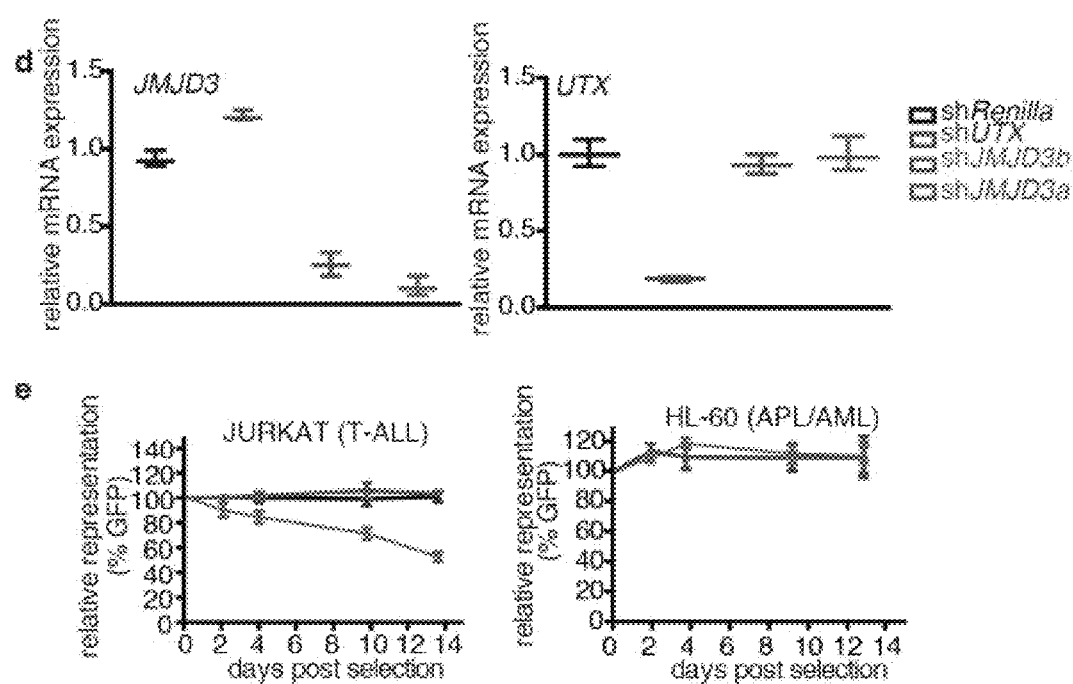
Figure 3F:
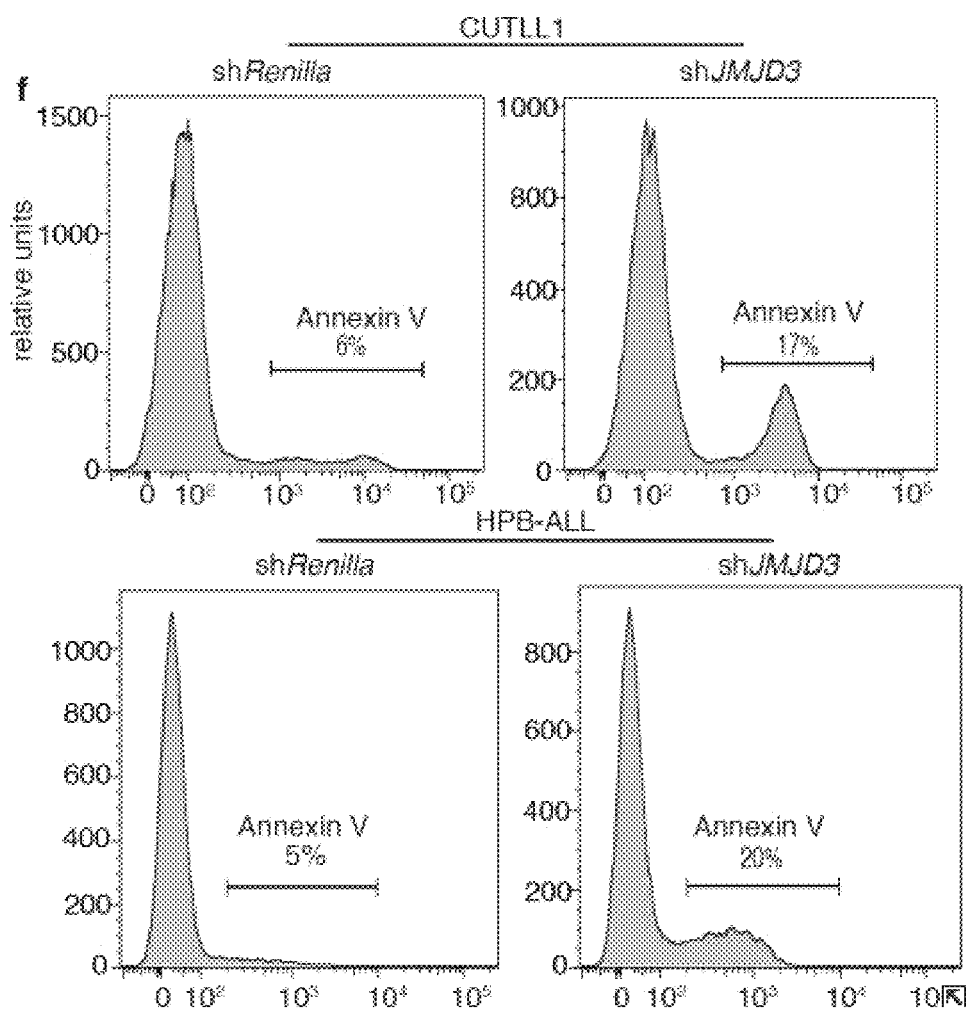
Figures 4A, 4B, 4C:
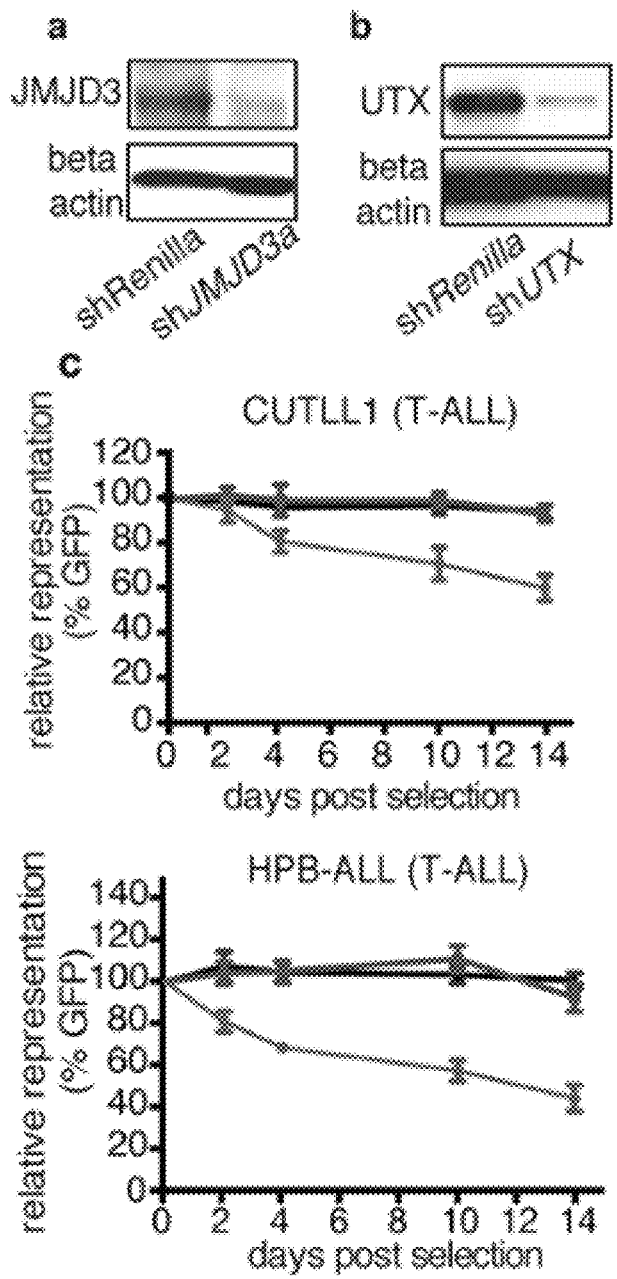
FIGS. 4A-4E demonstrates dissection of the oncogenic role of JMJD3 in T-ALL.
Figure 4D:
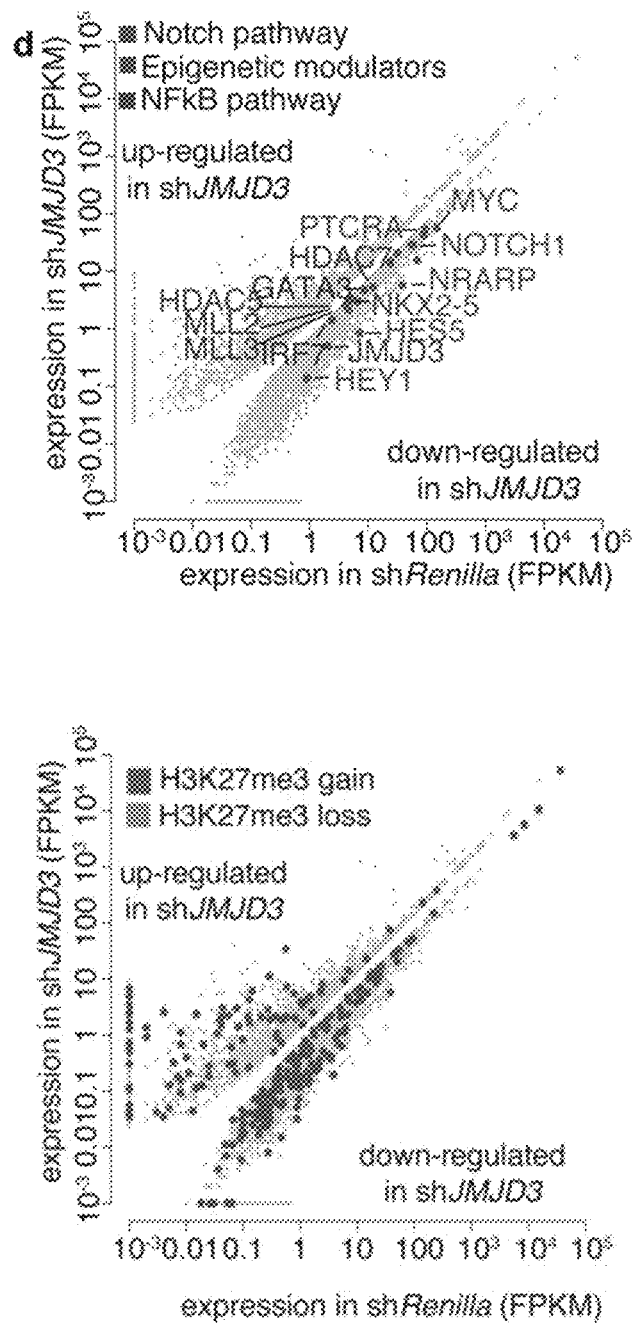
Figure 4E:
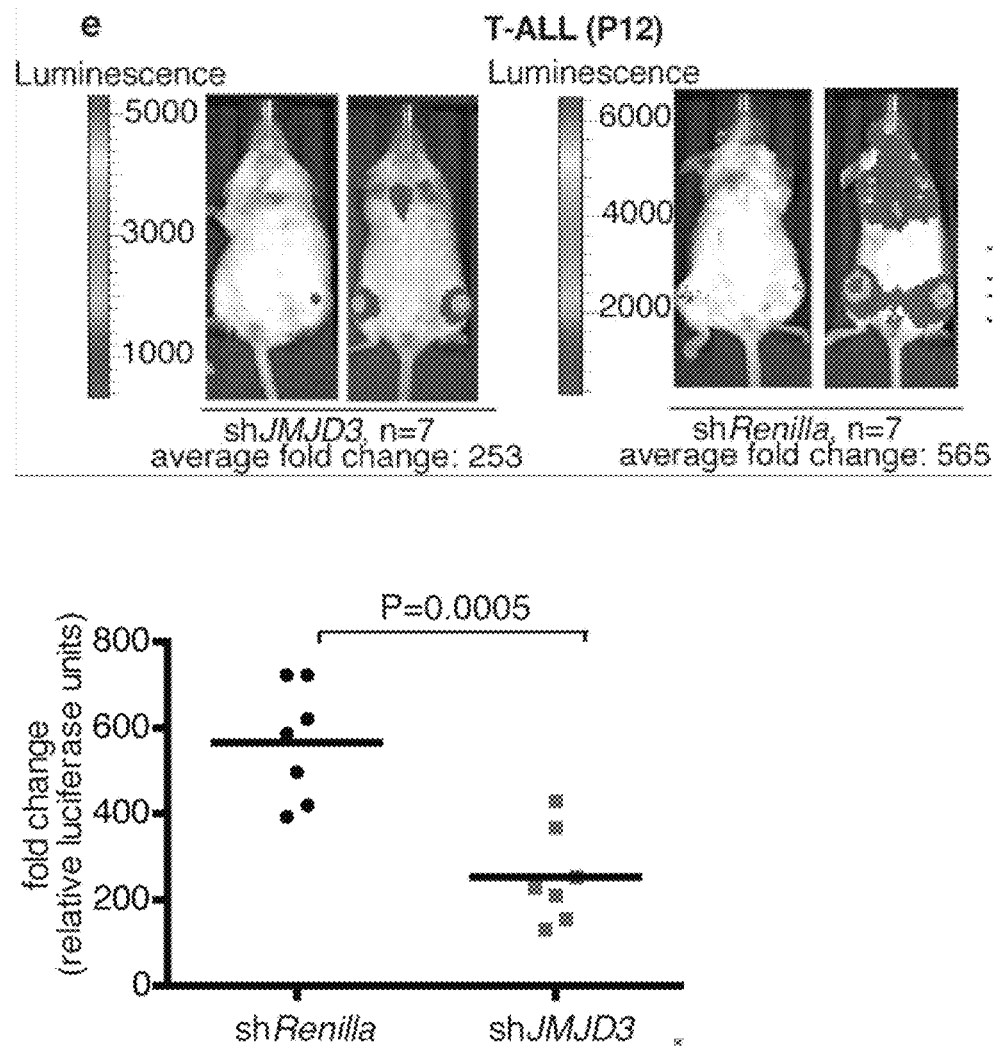
Figure 5A:
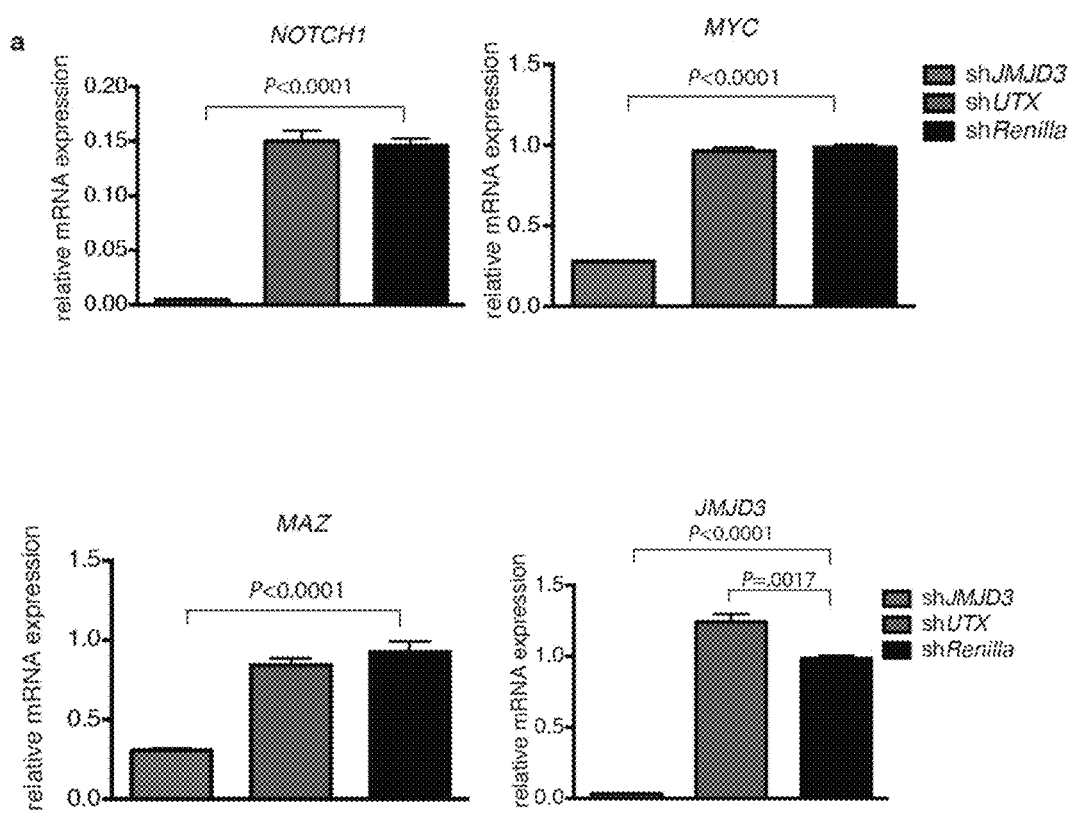
FIGS. 5A-5I show JMJD3 binds to genes with important oncogenic functions and is vital for T-ALL growth.
Figures 5B, 5C:
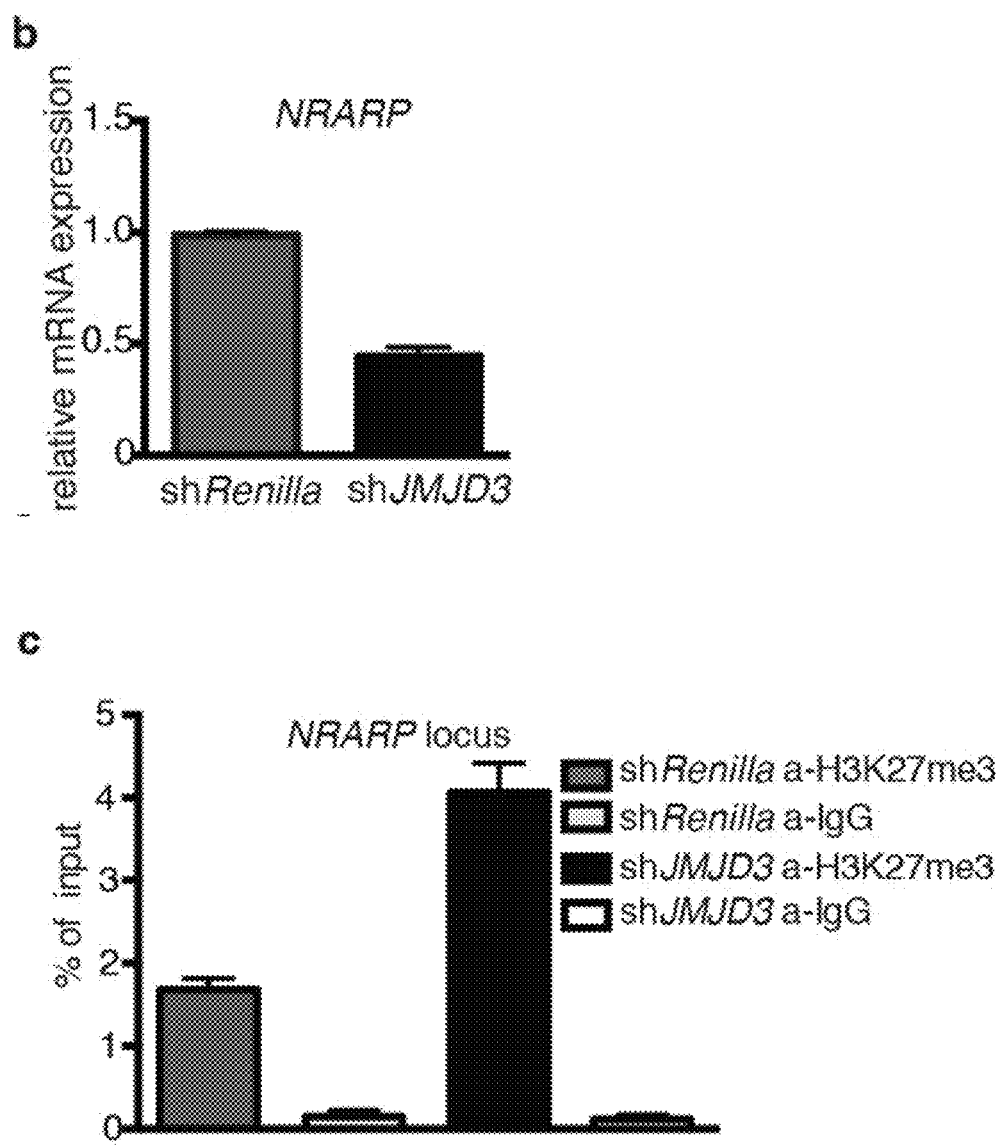
Figures 5D, 5E, 5F:
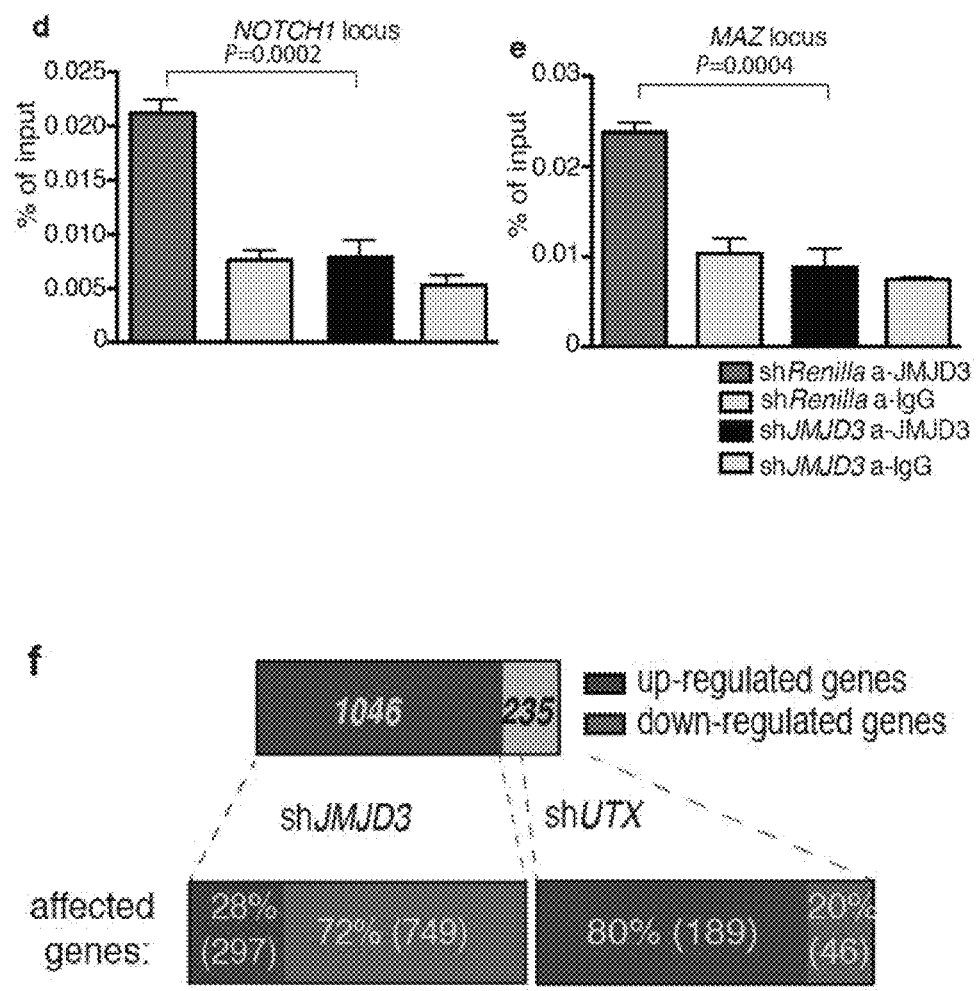
Figures 5G, 5H:
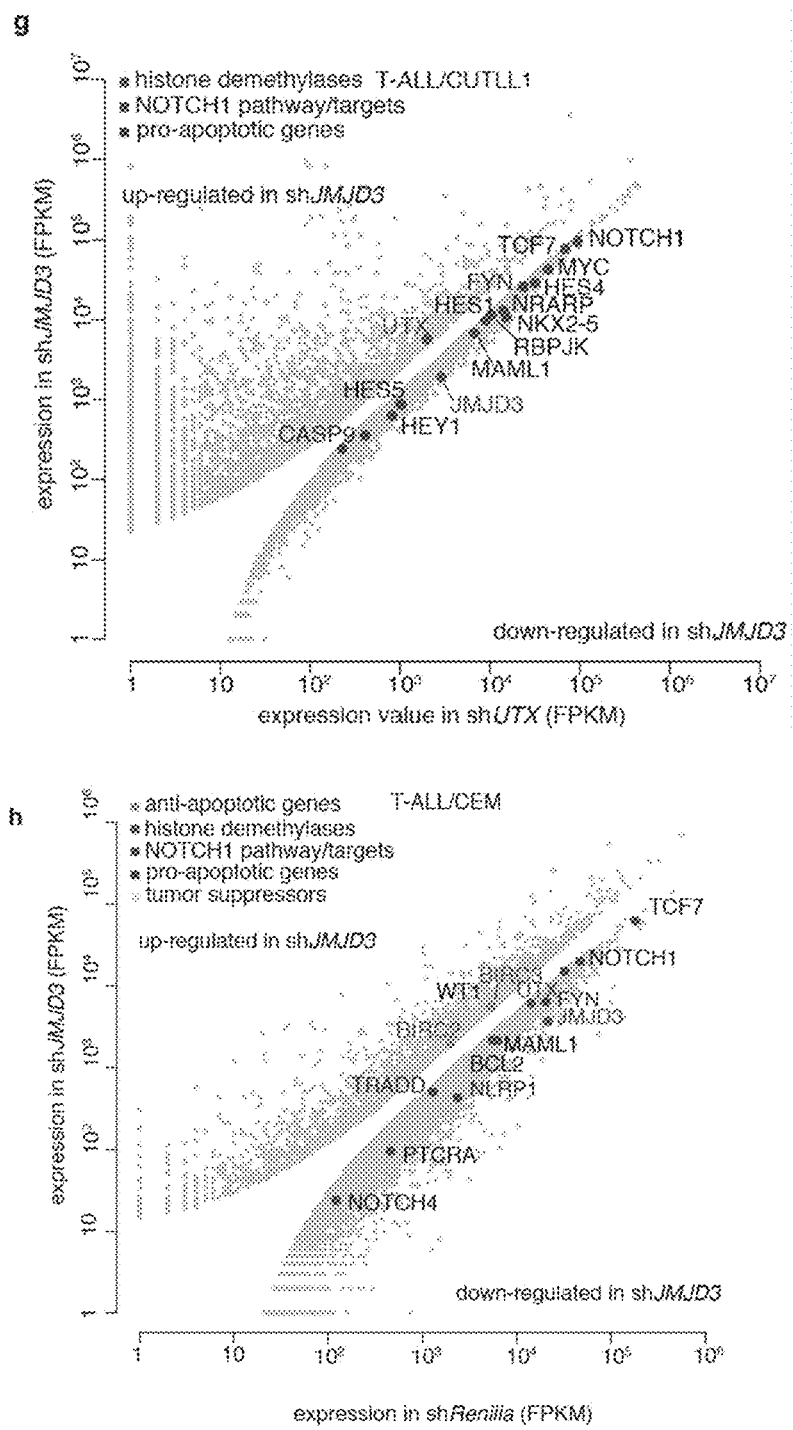
Figure 5I:
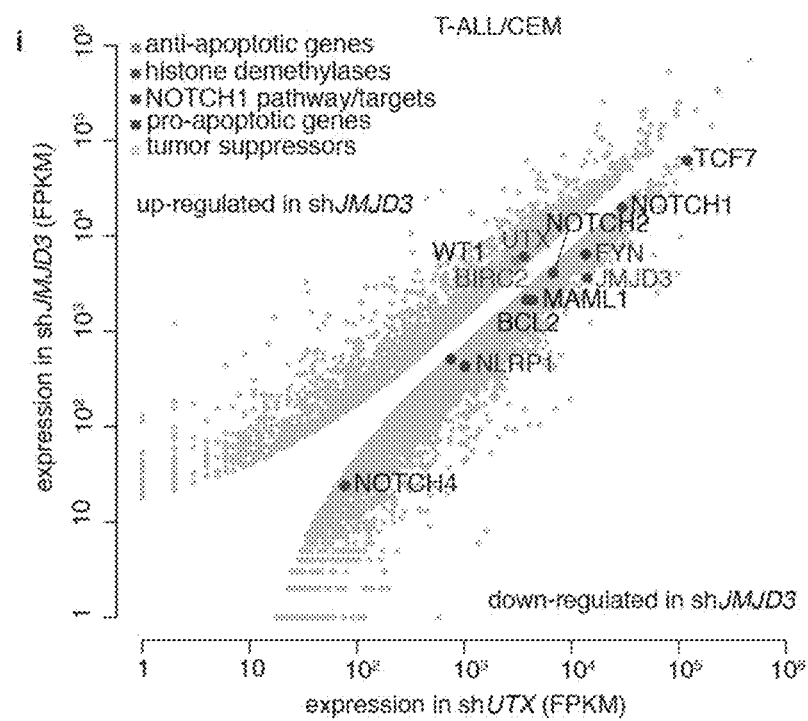
Figure 6A:
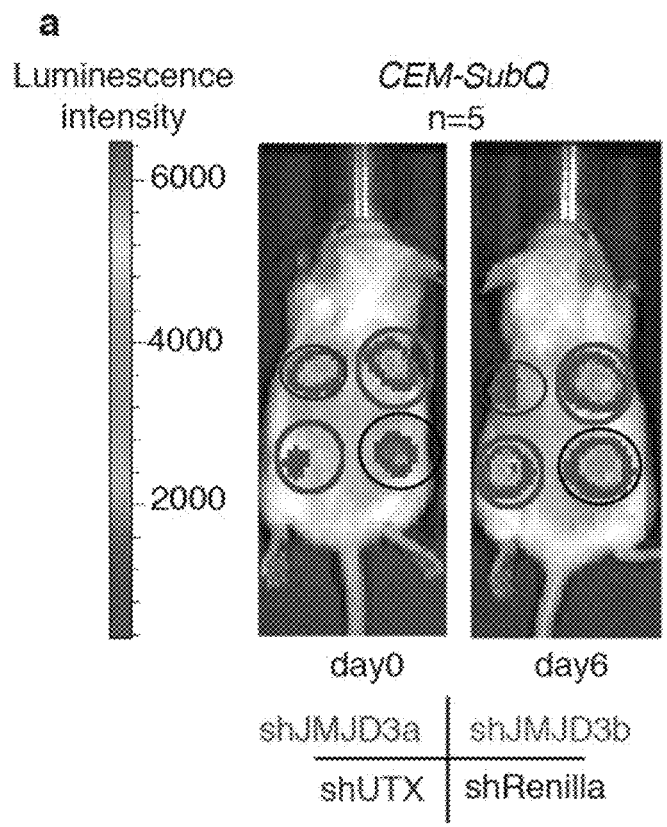
FIGS. 6A-6G show in vivo studies of the role of JMJD3 in T-ALL using luciferase analysis of CEM-, P12- and CUTLL1-based xenograft models in immunocompromised (NRG) mouse recipients.
Figure 6B:
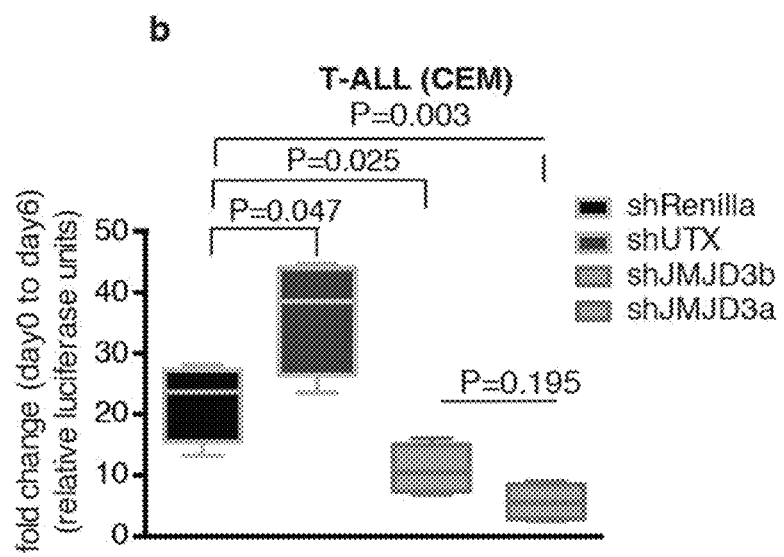
Figure 6C:
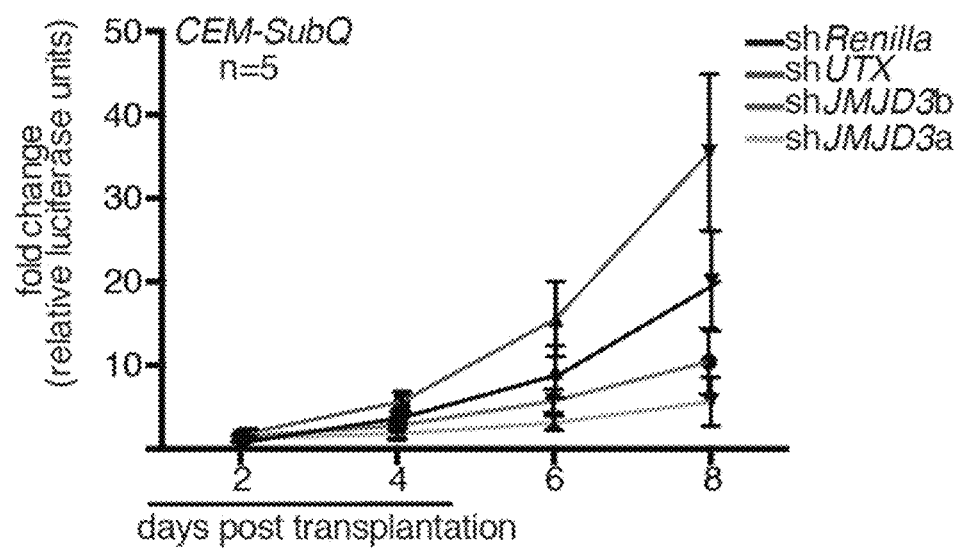
Figure 6D:
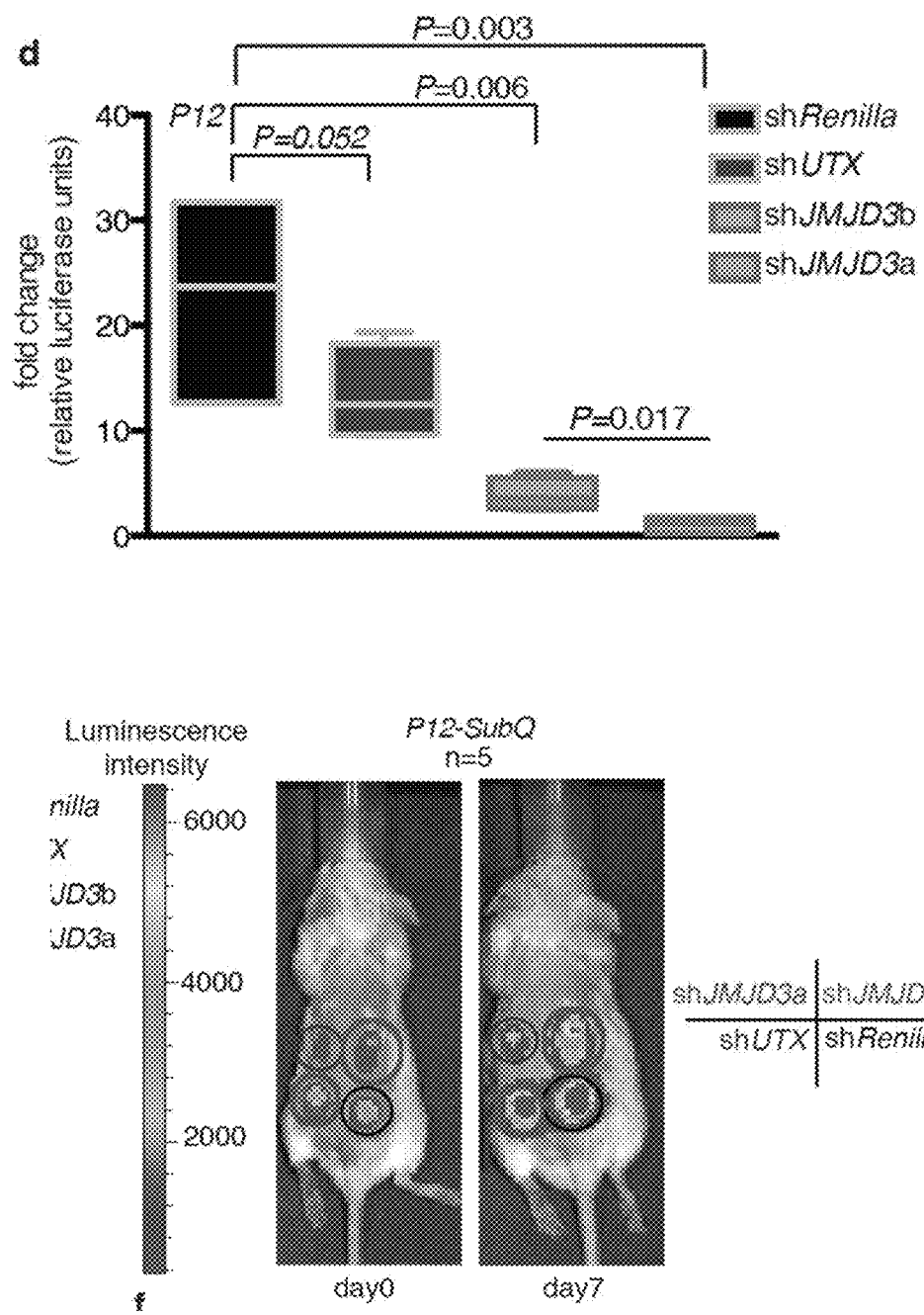
Figures 6E, 6F:
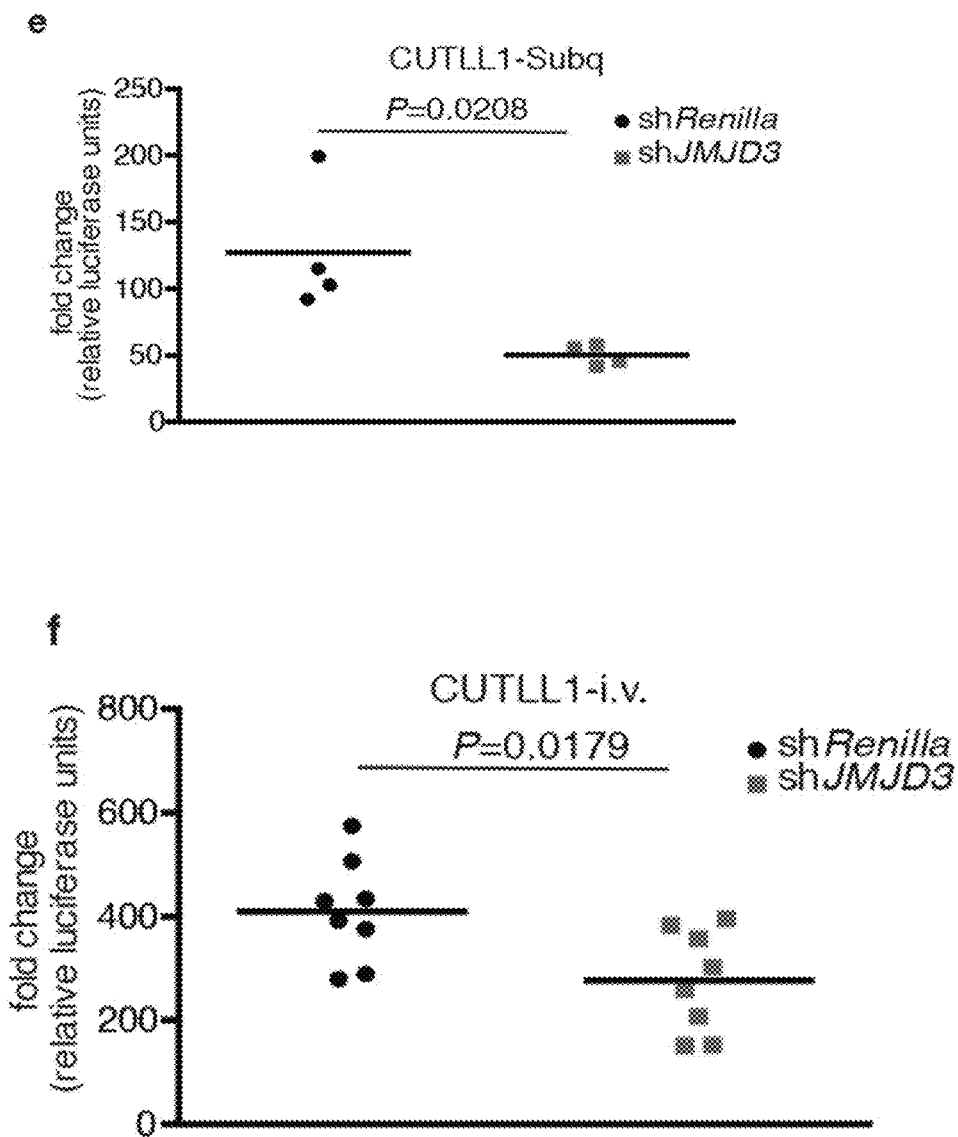
Figure 6G:
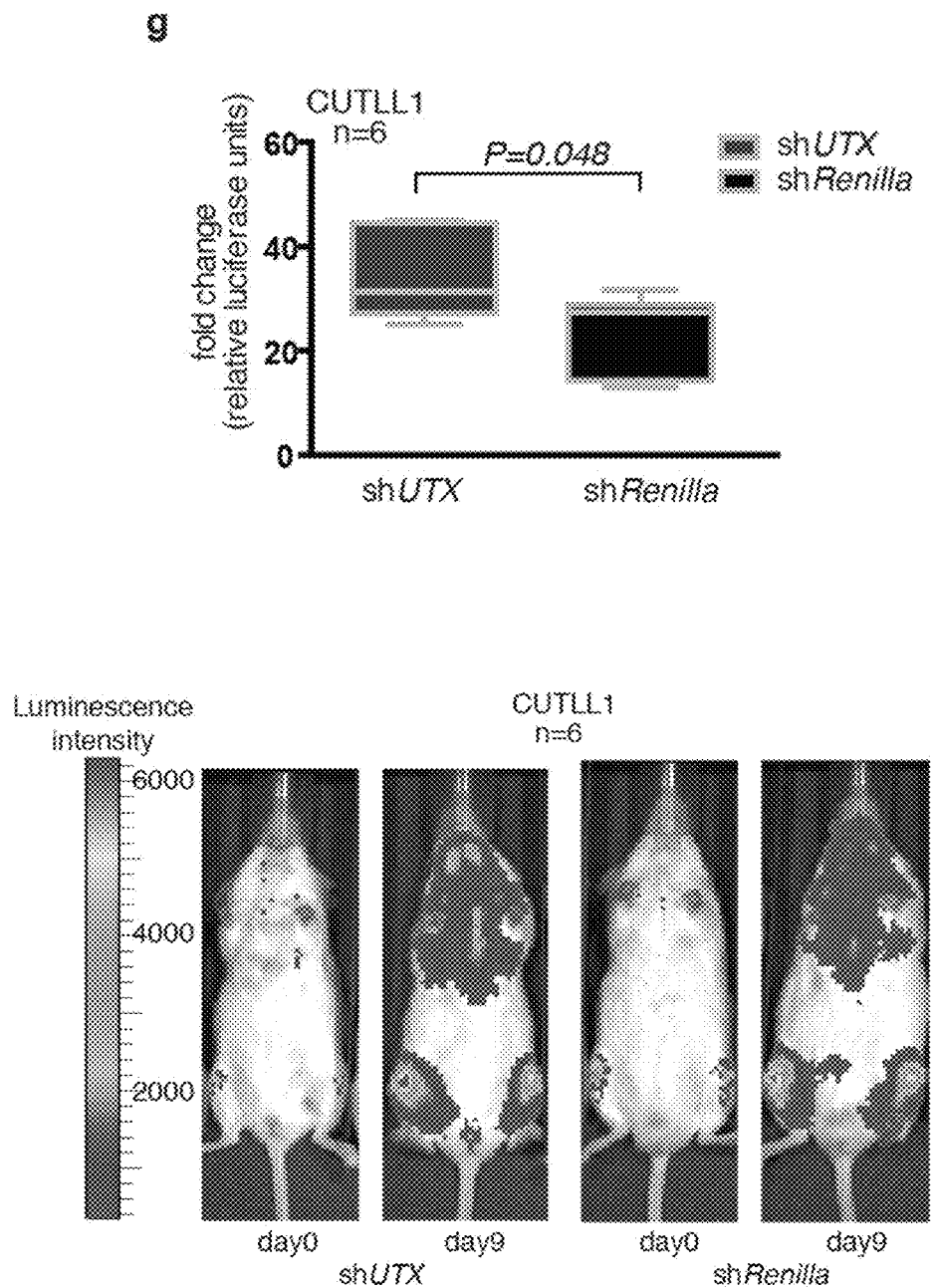

To clarify the role of JMJD3 and UTX in the maintenance of leukaemia, genomic knockdown of JMJD3 in human T-ALL cells was performed using two short hairpin RNAs (shRNAs) (FIGS. 4A-4B and FIG. 3D). Treatment with shJMJD3 but not shUTX affected the viability of leukaemic cells, as shown in loss of representation studies and apoptosis assays, and this finding is in contrast to the viability of myeloid leukaemia lines used as controls (FIG. 4C and FIGS. 3E-3F). The expression of NOTCH1 targets was negatively affected by shJMJD3, and this was accompanied by loss of JMJD3 and gain of H3K27me3 on their promoters (FIGS. 5A-5E). Genome-wide expression analysis showed that more transcripts were significantly downregulated by shJMJD3 treatment than were upregulated (749 protein-coding genes versus 297; FIG. 4D, top, and FIG. 5F), in agreement with the role of JMJD3 as a transcriptional activator. The downregulated genes were found to be significantly enriched in genes that gained H3K27me3 on their promoters (FIG. 4D, bottom; $P=1.02\times10^{-7}$). The shUTX downregulated and shUTX-upregulated gene signatures were reversed in terms of the gene numbers (46 downregulated and 189 upregulated protein-coding genes, compared with both shRenilla (control) and shJMJD3). Intriguingly, JMJD3 expression itself was significantly upregulated upon UTX silencing (FIG. 5A). Well-characterized NOTCH1 targets, as well as genes in the NF-kB pathway were downregulated as part of the JMJD3 signature (FIG. 4D, top, and FIG. 5G). These findings were confirmed using additional human T-ALL cell lines with high levels of oncogenic NOTCH1 activity (Weng et al., "Activating Mutations of NOTCH1 in Human T Cell Acute Lymphoblastic Leukemia," Science 306:269-271 (2004), which is hereby incorporated by reference in its entirety) (FIGS. 5H-5I). Subcutaneous or intravenous xenograft models of T-ALL cell lines (CUTLL1, CEM and P12) treated with either of the two shRNAs against JMJD3 (shJMJD3A and shJMJD3B) and transplanted into immunocompromised mice (NRG mice; NOD Rag1$^{-/-}$Il2rg$^{-/-}$) showed a significant growth disadvantage compared with shRenilla-treated cell lines (FIG. 4E and FIGS. 6A-6F). Interestingly, silencing of UTX led to enhanced proliferation in many cases, suggesting a possible tumour-suppressor function in vivo (FIG. 6G).

Example 3

The Demethylase UTX Acts as a Tumour Suppressor in T-ALL

To examine the potential roles of UTX and JMJD3 in the induction of T-ALL, bone marrow transplantation experiments were performed using haematopoietic stem cells from Utx and Jmjd3 germline knockout mice. Although female Utx$^{-/-}$ mice die at E9.5 because of defects in mesoderm development, a small fraction of male Utx$^{-/Y}$ mice survive to adulthood as a result of compensation by UTY (Welstead et al., "X-linked H3K27me3 Demethylase Utx is Required for Embryonic Development in a Sex-Specific Manner," Proc. Natl. Acad. Sci. USA 109:13004-13009 (2012), which is hereby incorporated by reference in its entirety). Despite T-cell development being largely unaffected (FIGS. 7A-7B), T-ALL kinetics were significantly faster on the Utx$^{-/Y}$ background, as determined by leukaemic burden quantification in the peripheral blood and infiltration of the spleen and liver (FIGS. 8A-8C and FIGS. 7C-7E). Moreover, mice succumbed to the disease with a significantly shorter latency in the absence of Utx than in the Utx$^{+/Y}$ and Utx$^{+/+}$ genotypes (FIG. 8D and FIGS. 7F-7H). These experiments provide the first in vivo analysis of the tumour-suppressor role of UTX in any tumour type.

Figures 7H, 7I:
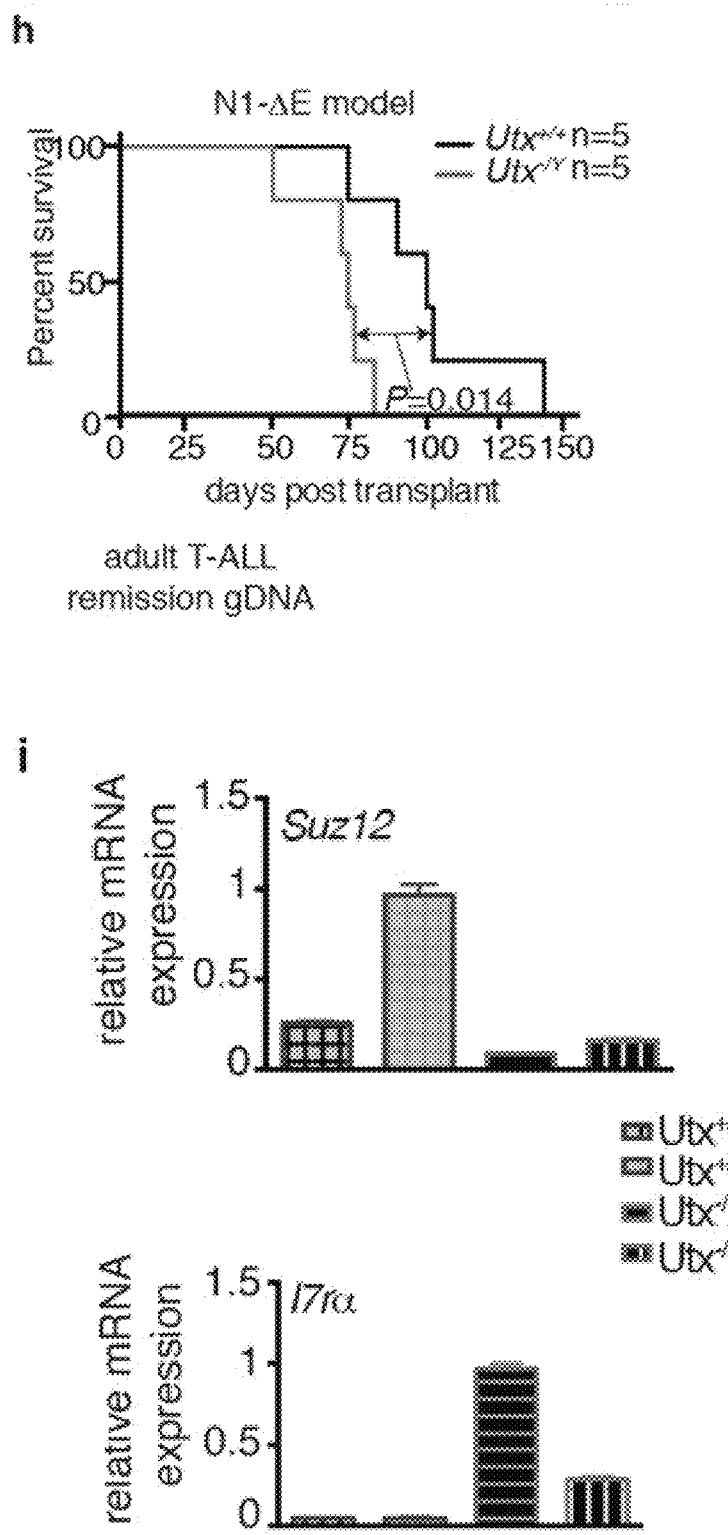
FIG. 7I shows quantitative PCR (qPCR) validation of the expression levels of one downregulated gene (Suz12) and one upregulated gene (Il7r) in $Utx^{-/Y}$(compared with $UTX^{+/Y}$) mice. The average results from three independent samples (studies) are presented.

To delineate the potential mechanism underlying UTX action, the gene expression of sorted leukaemic blasts from the spleen or bone marrow of wild-type (Utx$^{+/Y}$/Utx$^{+/+}$) or knockout (Utx$^{-/Y}$) mice (FIG. 8E) was analyzed. This analysis showed that UTX positively controls important tumour-suppressor genes, such as retinoblastoma binding protein 6 (Rbbp6), the inhibitor of NOTCH1 pathway activity Fbxw7 and the PRC2 member Suz12; by contrast, genes with an oncogenic role in T-ALL, including Jmjd3, were upregulated (FIG. 8E and FIG. 7I). These studies strongly suggested that UTX might act as a tumour suppressor in human T-ALL. Thus, a panel of primary pediatric T-ALL samples (Zhang et al., "The Genetic Basis of Early T-cell Precursor Acute Lymphoblastic Leukaemia," Nature 481:157-163 (2012), which is hereby incorporated by reference in its entirety) were screened for genetic alterations of the UTX locus. Analysis of primary human samples of pediatric T-ALL using single nucleotide polymorphism (SNP) arrays identified two patients with focal deletions of the UTX locus (FIG. 8F). Further targeted sequencing in pediatric and adult T-ALL led to the identification of six more patient cases with UTX mutations (FIG. 8G, FIGS. 7J-7K and Table 2), including in-frame deletions missense (Ile598Val) mutations and frameshift alterations

TABLE 2

Details on the frameshift mutations identified in pediatric T-ALL (Sanger sequencing)

Flanking sequence [wt sequence > mutant sequence] flanking sequence

SJTALL037:R1111fs, TGCTTTTGTG[C-------->GGGGCGTAA]GTGTCGTATC
(SEQ ID NO: 59)

SJTALL177:V1113fs, GTGCGTGTCG[------->GGTGTCG]TATCAGCAGG
(SEQ ID NO: 60)

SJTALL189:V1112fs, TTGTGCGTGT[CGTATCA-->GGCTAATAG]CAGGAAATCT
(SEQ ID NO: 61)

Figures 7J, 7K:
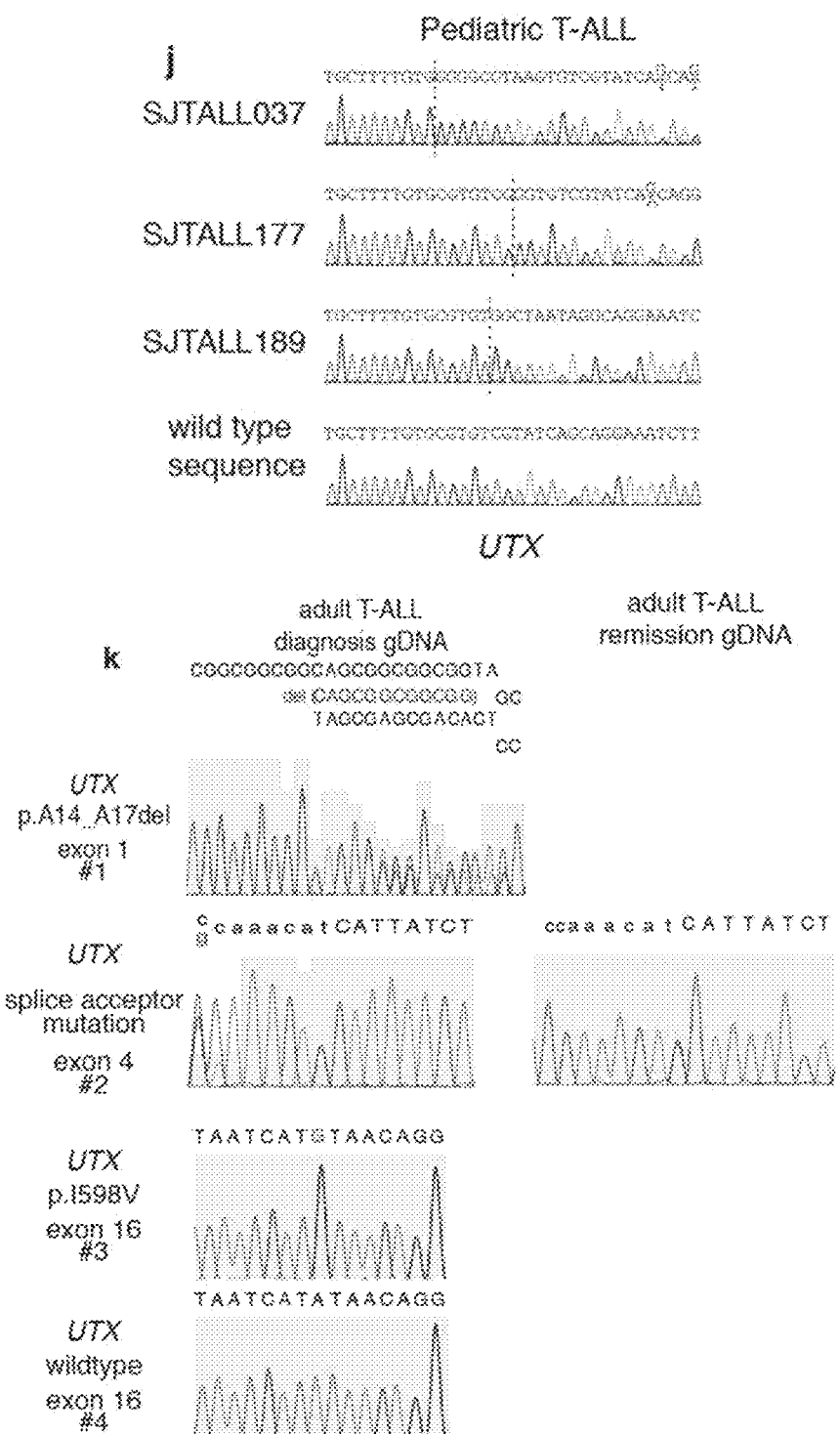
FIG. 7J shows targeted Sanger sequencing in pediatric T-ALL led to the identification of three cases with frameshift mutations. The positions of the mutations are indicated by dashed lines in the electropherograms.
FIG. 7K shows identification of one in-frame deletion (p.Ala14_Ala17del, #1, top panel), one splice acceptor site (#2, second panel) and one missense mutation (#3, third panel) in adult T-ALL. Case #4 is an adult T-ALL case with wild-type UTX (control, bottom panel). Mutations are indicated by red characters.
Figures 7L, 7M:
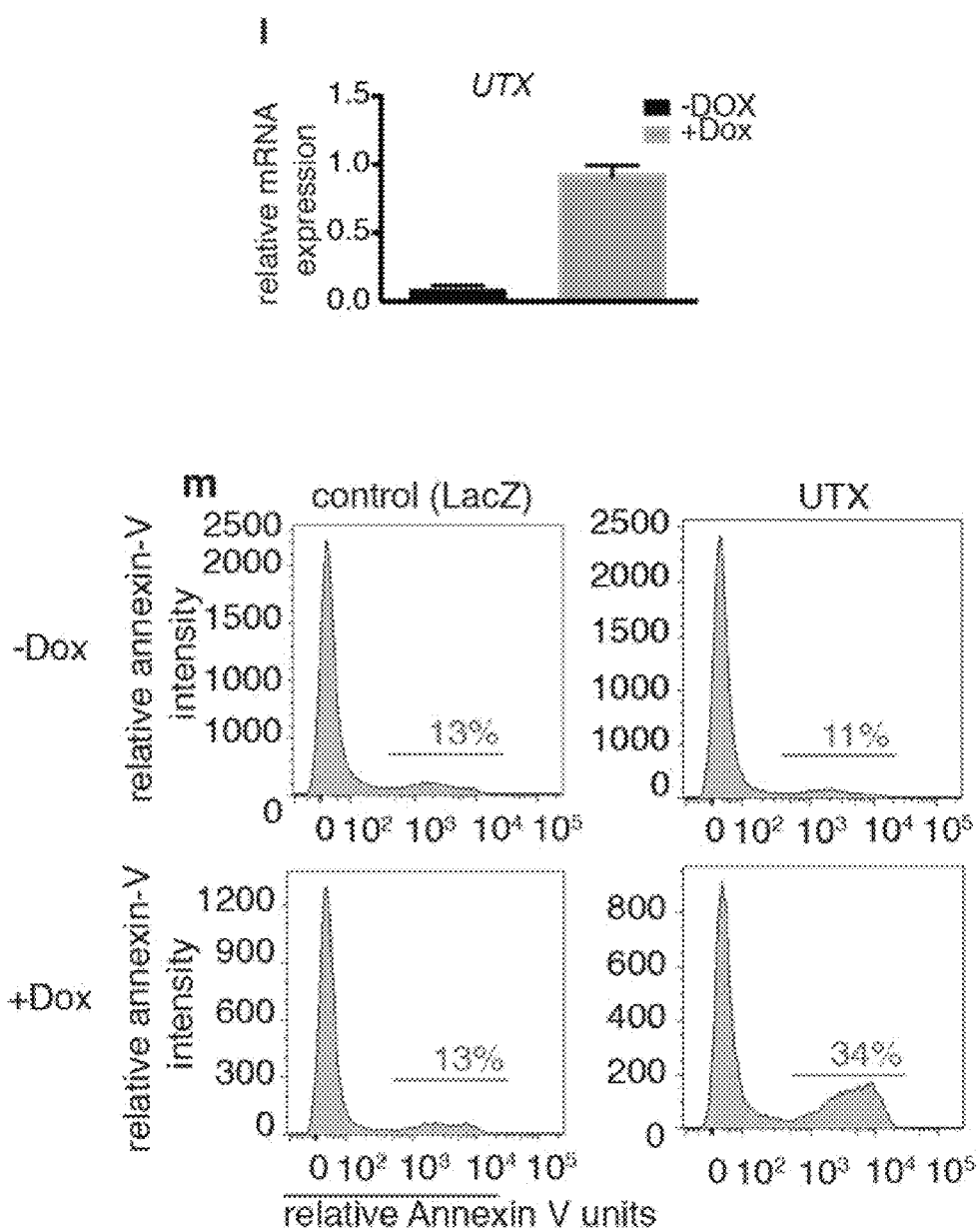
Figure 7N:
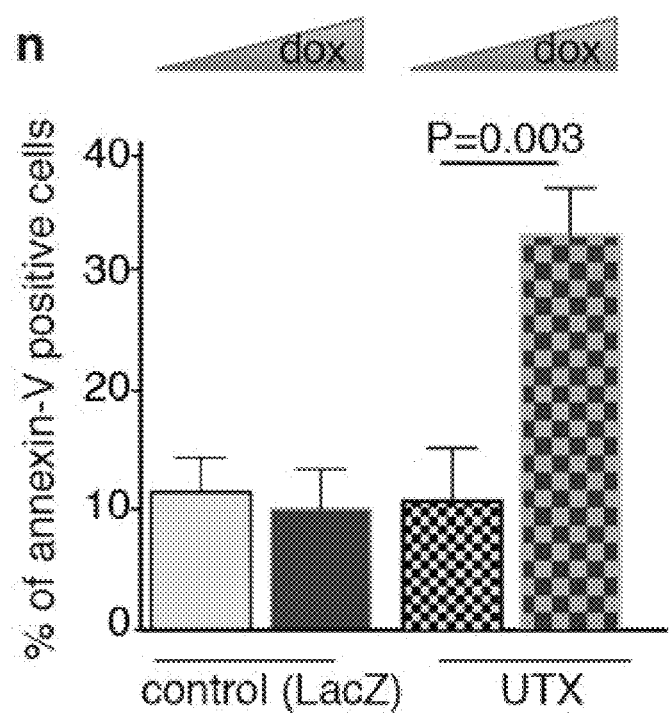
Figures 8A, 8B, 8C:
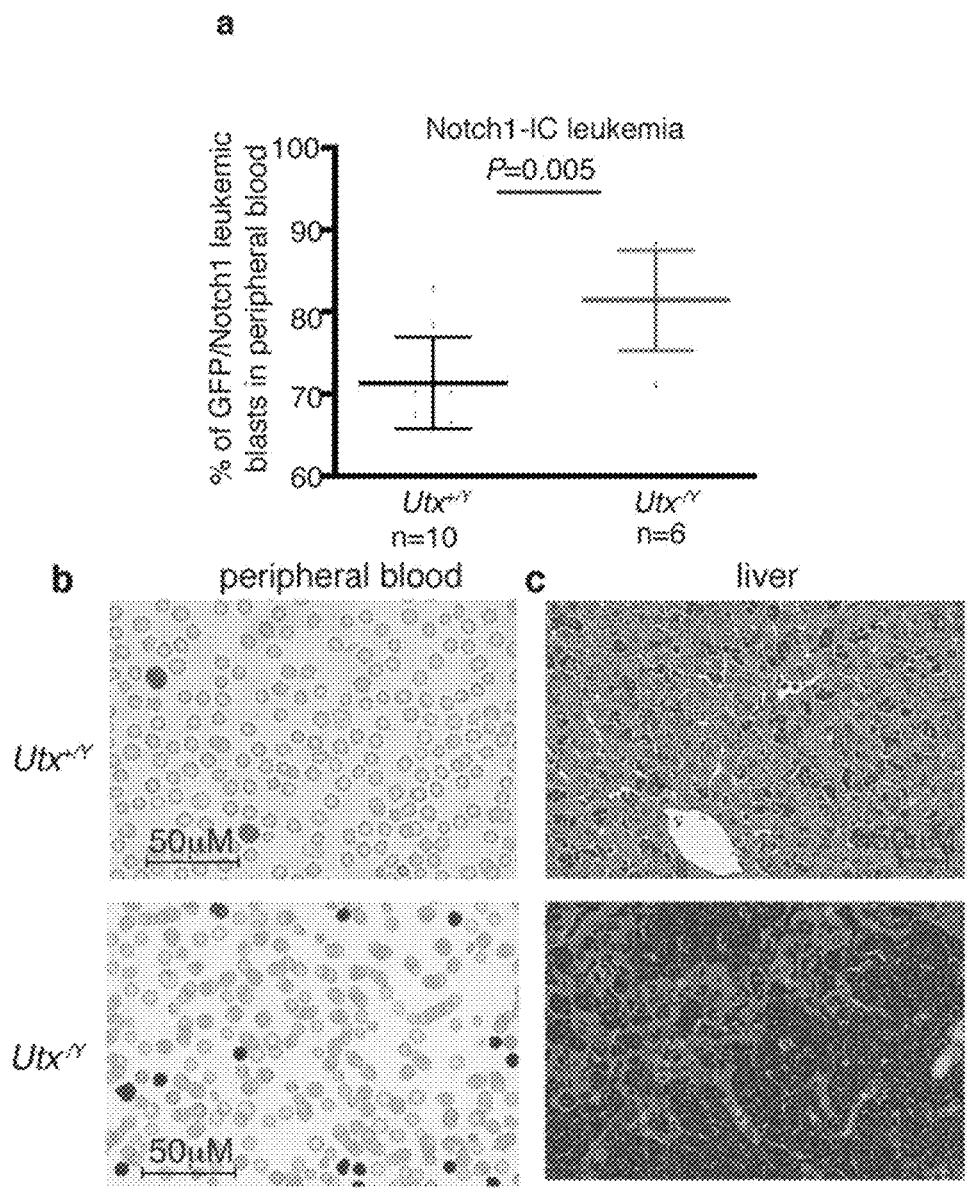
FIGS. 8A-8G show the demethylase UTX acts as a tumor suppressor in T-ALL.
Figure 8D:
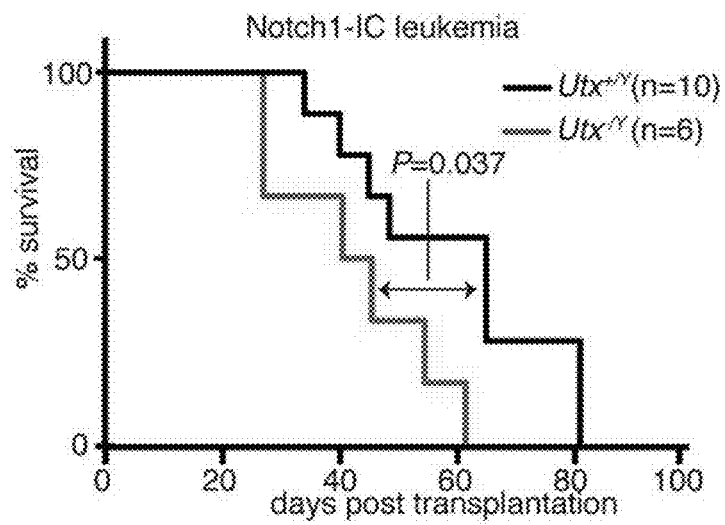
Figure 8E:
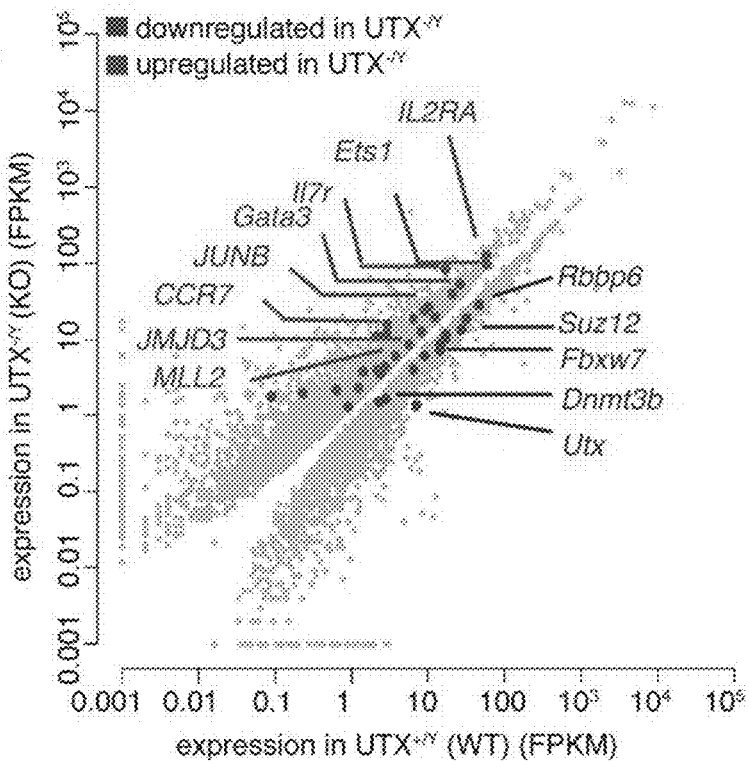
Figures 8F, 8G:
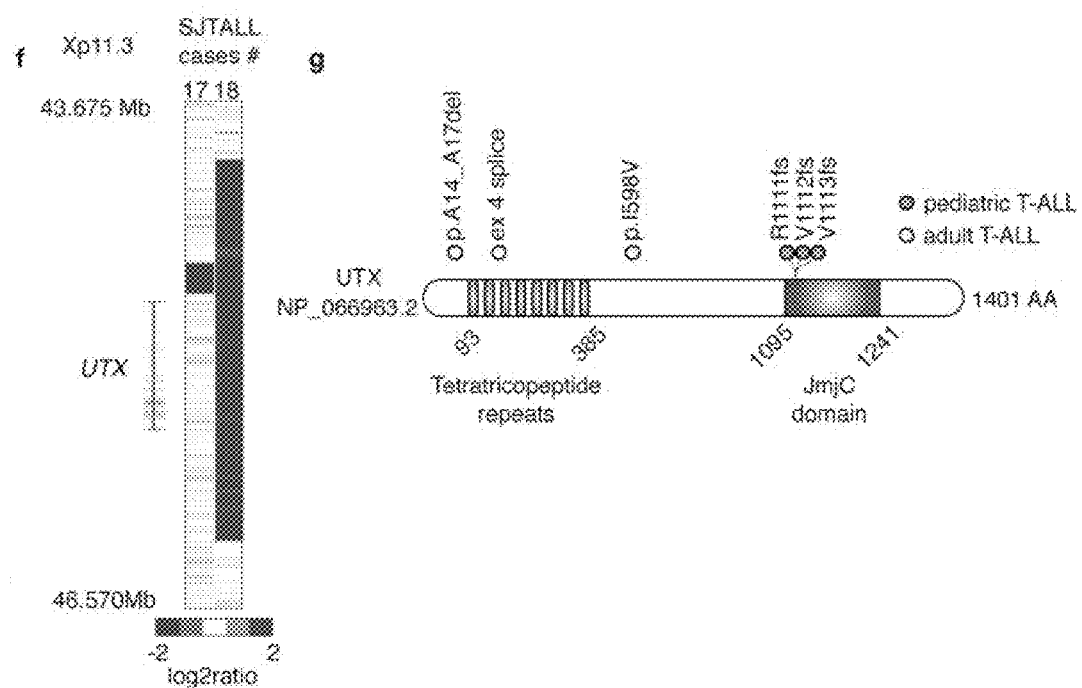

Analysis of bone marrow remission genomic DNA confirmed the somatic origin of the UTX splice site mutation (FIG. 7K). Seven out of the eight alterations belonged to male patients, further underlining that the roles of UTX and UTY do not seem to be interchangeable. These genetic alterations are predicted to have an inactivating role (van Haaften et al., "Somatic Mutations of the Histone H3K27 Demethylase Gene UTX in Human Cancer," Nature Genet. 41:521-523 (2009); Mar et al., "Sequencing Histone-Modifying Enzymes Identifies UTX Mutations in Acute Lymphoblastic Leukemia," Leukemia 26:1881-1883 (2012), which is hereby incorporated by reference in its entirety) and provide further evidence that UTX is a tumour suppressor in T-ALL. Indeed, overexpression of UTX using a doxycycline-inducible lentiviral system in T-ALL cell lines (FIG. 7L) led to suppression of tumour growth and a significant increase in apoptosis (FIGS. 7M-7N).

Example 4

Physiological Development of the Hematopoietic System and T-ALL Initiation in the Absence of JMJD3

Figures 9A, 9B:
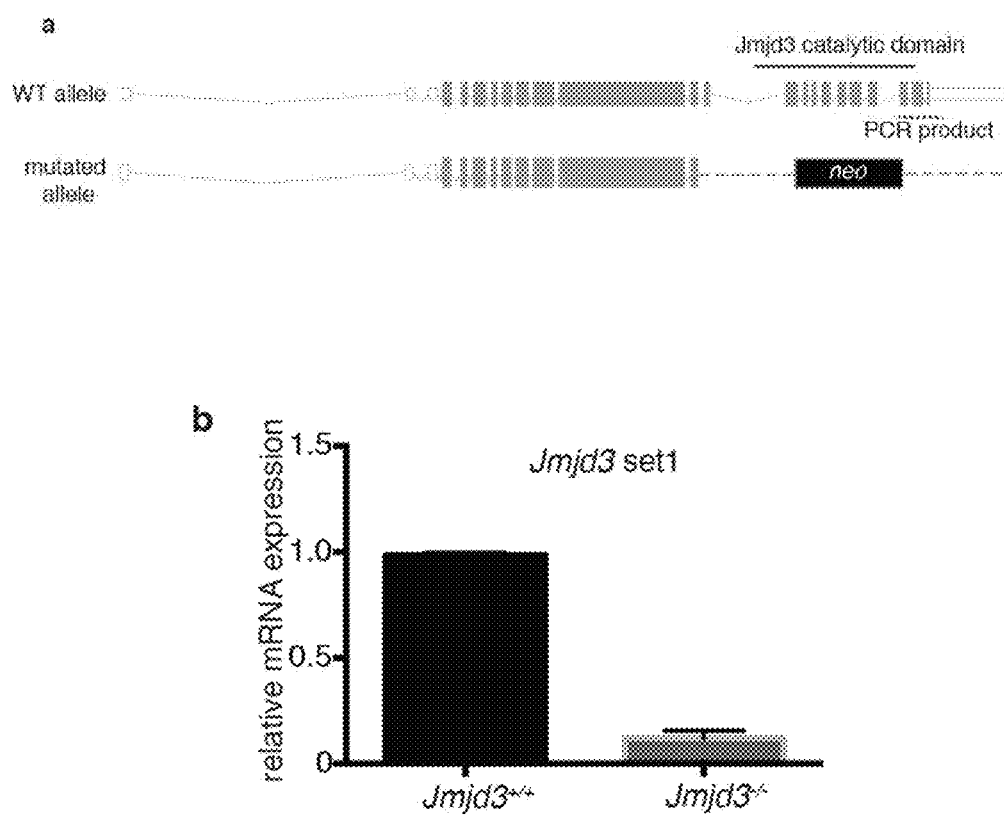
FIGS. 9A-9H show physiological development of the hematopoietic system in the absence of JMJD3.
Figures 9C, 9D:
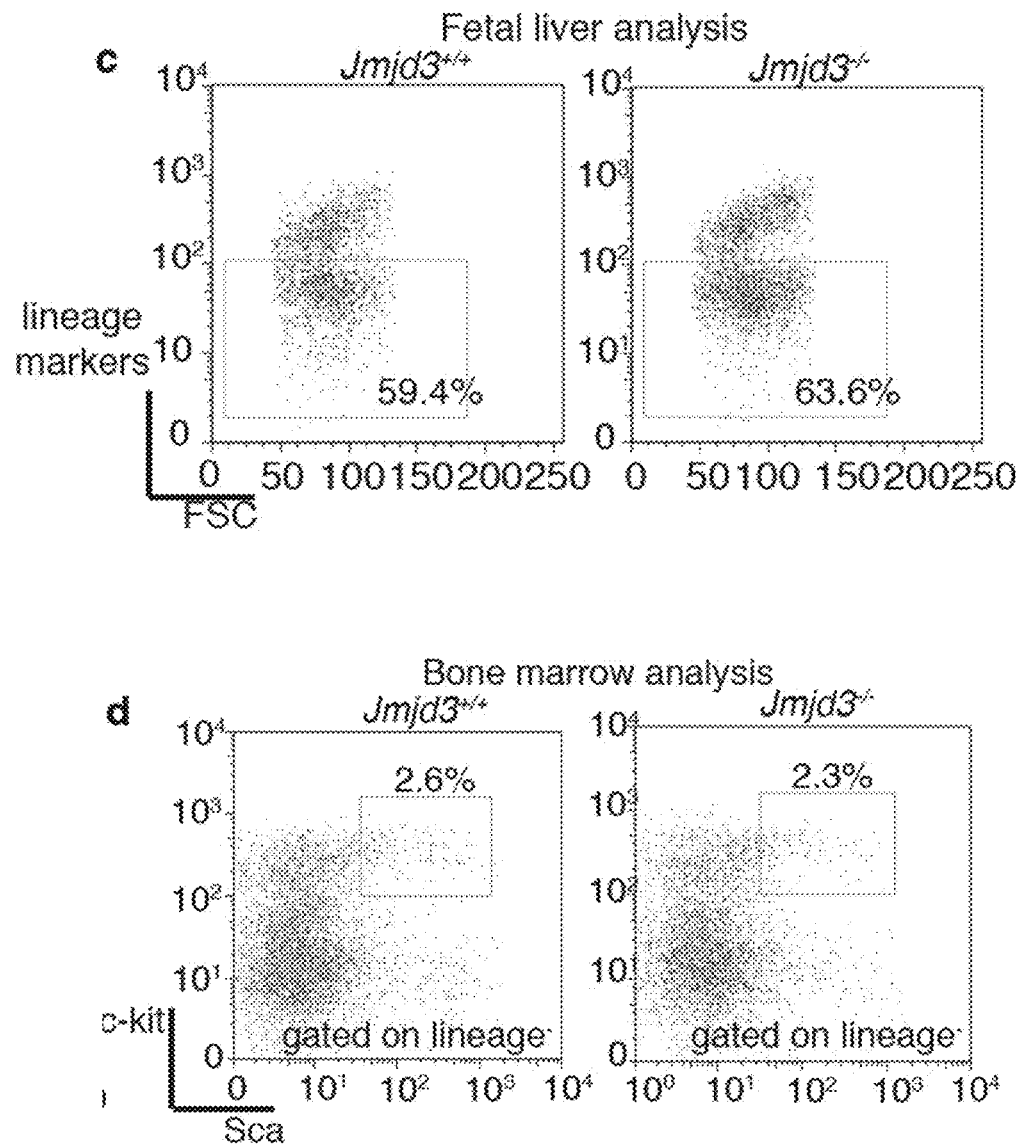
Figures 9E, 9F, 9G:
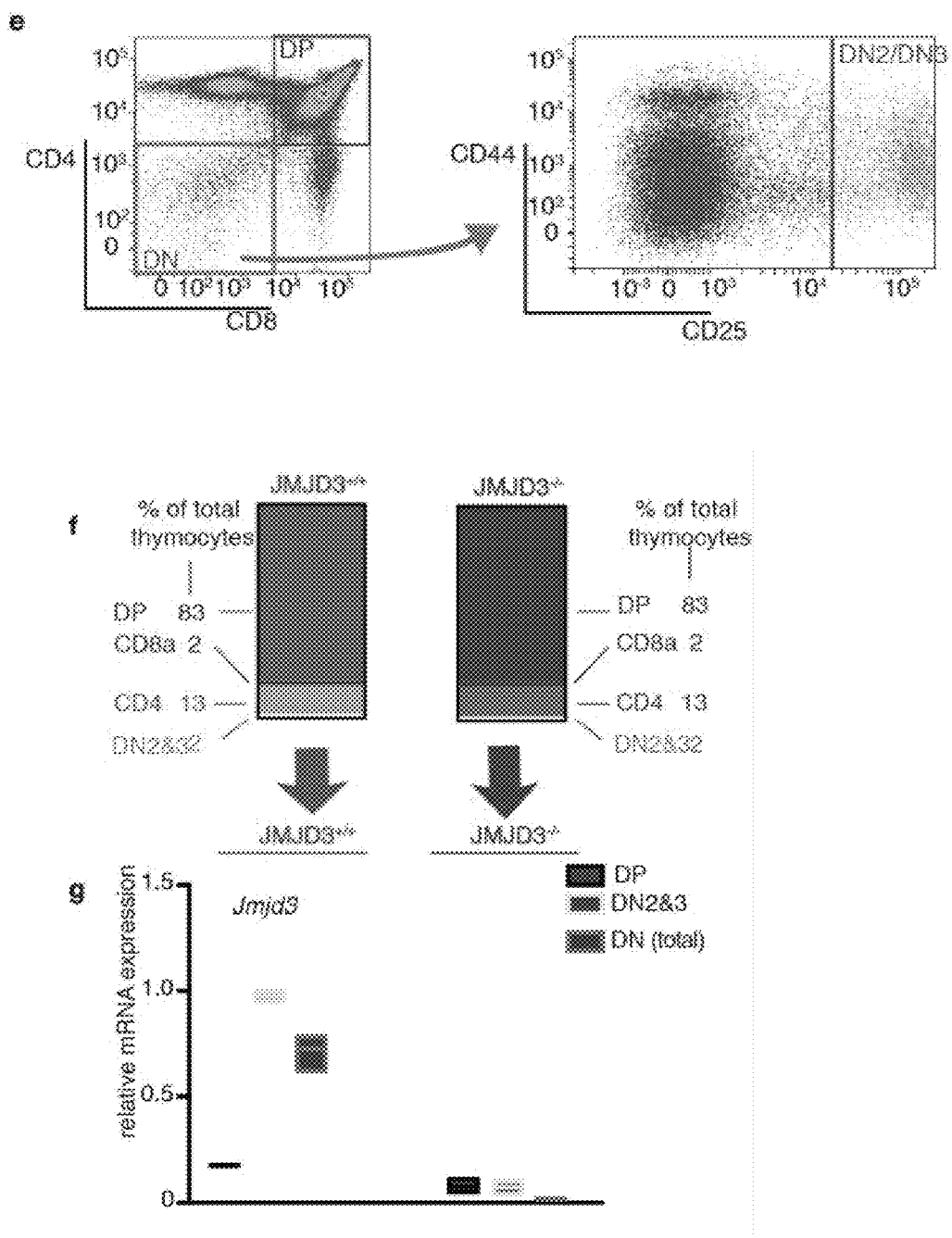
Figure 9H:
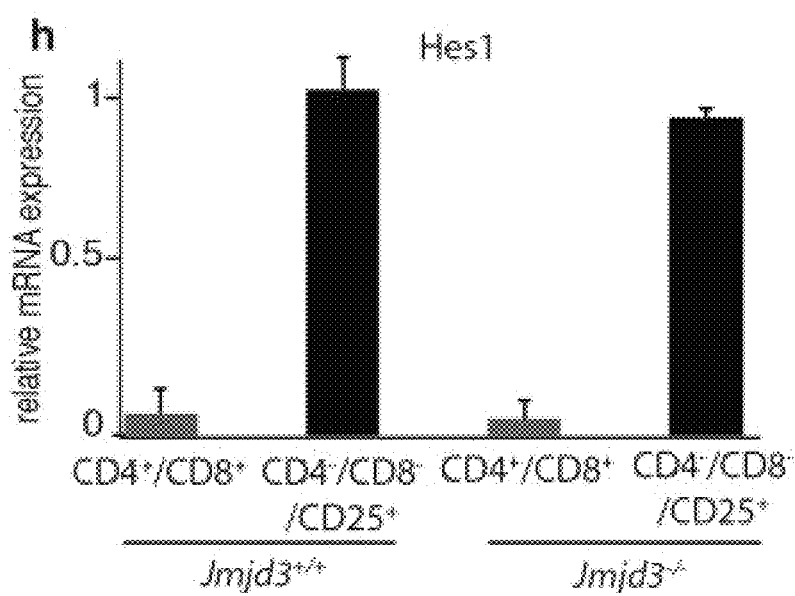
Figures 10A, 10B, 10C, 10D:
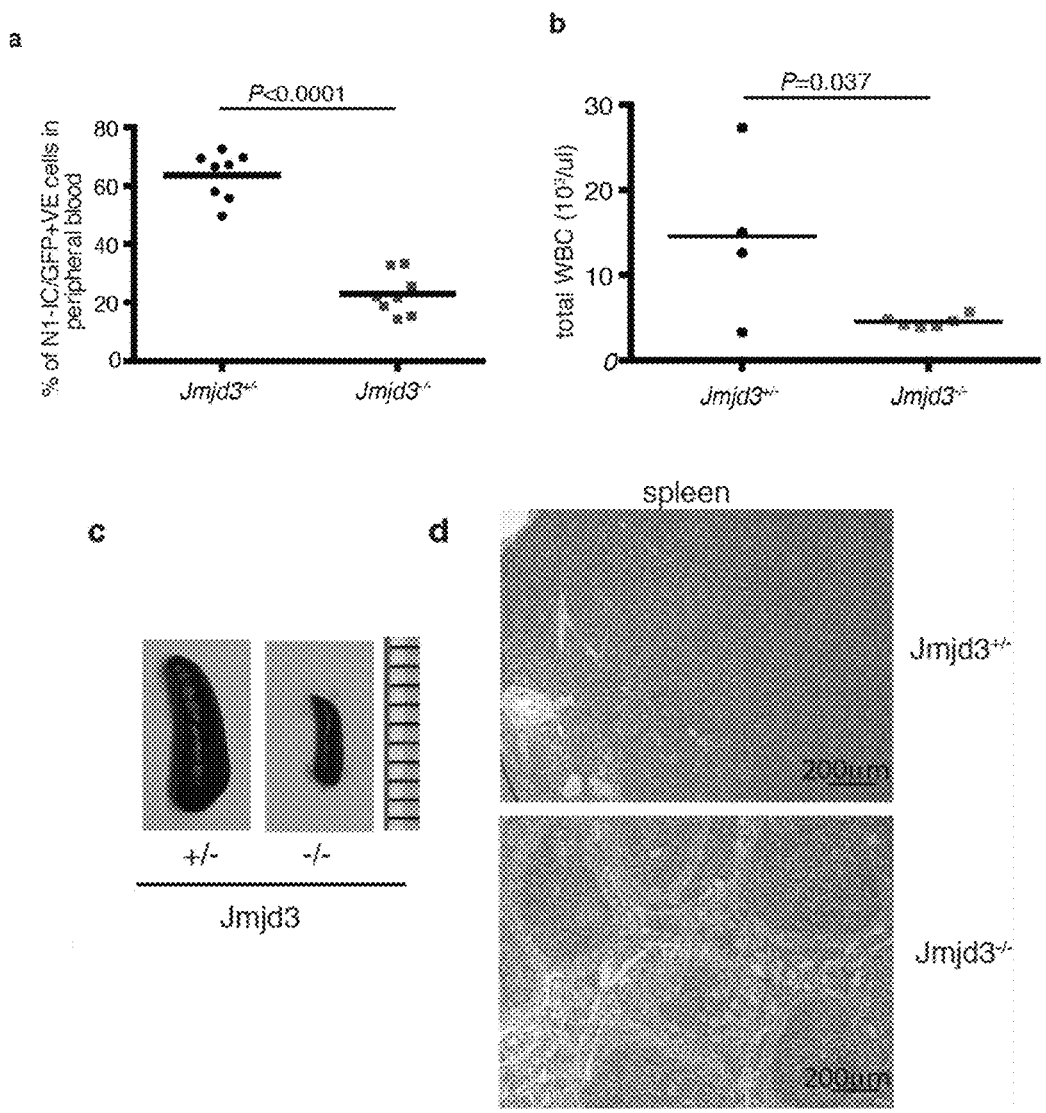
FIGS. 10A-10F demonstrate that JMJD3 is necessary for disease initiation in an animal model of T-ALL. Initiation of the disease was studied by transplanting c-Kit+ hematopoietic progenitors.
Figures 10E, 10F:
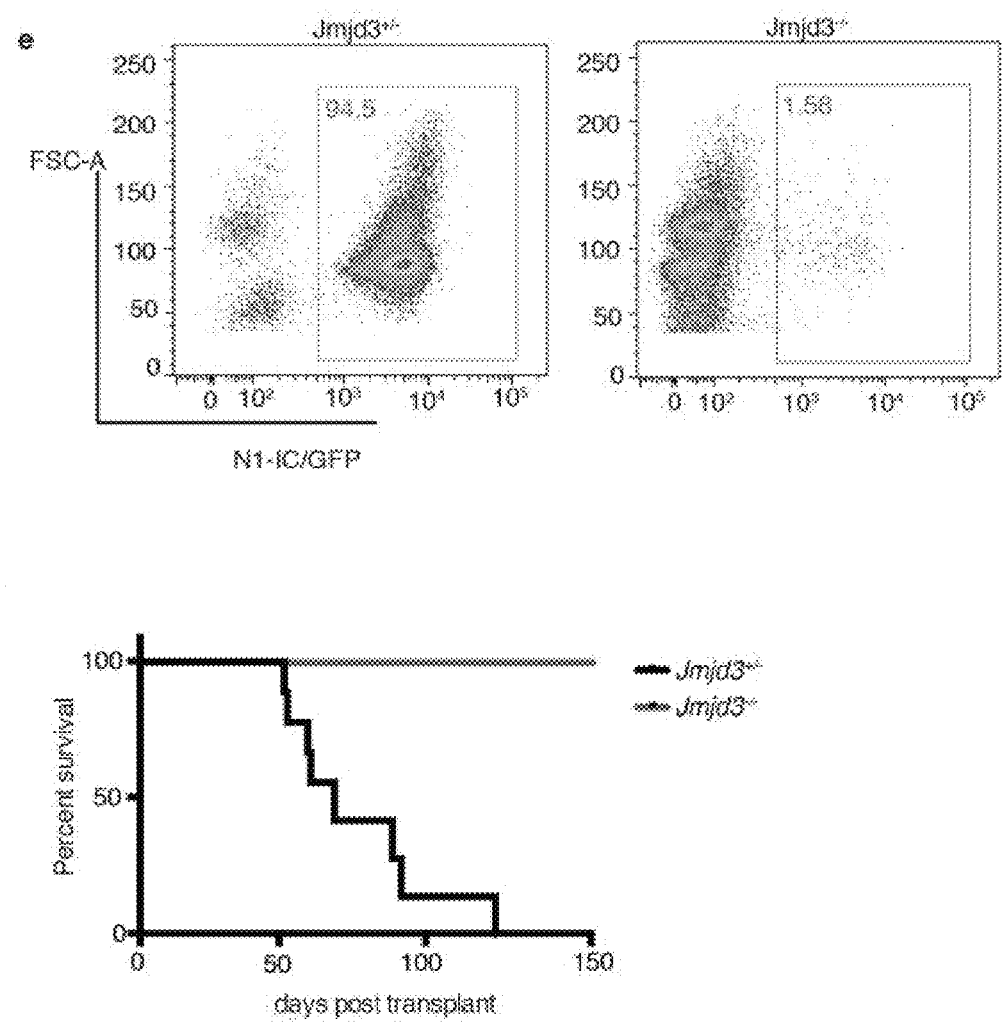

Jmjd3$^{-/-}$ mice (Satoh et al., "The Jmjd3Irf4 Axis Regulates M2 Macrophage Polarization and Host Responses Against Helminth Infection," Nature Immunol. 11:936-944 (2010), which is hereby incorporated by reference in its entirety) lack the catalytic domain of the JMJD3 protein (FIGS. 9A-9B) and die perinatally (Satoh et al., "The Jmjd3Irf4 Axis Regulates M2 Macrophage Polarization and Host Responses Against Helminth Infection," Nature Immunol. 11:936-944 (2010), which is hereby incorporated by reference in its entirety). Haematopoiesis and T-cell development were largely unaffected by the absence of JMJD3 (FIGS. 9C-9H). Genetic ablation of Jmjd3 in T-ALL led to fewer leukaemic blasts in the peripheral blood, significantly reduced leukaemic cell infiltration of the spleen and liver and improved survival rates in the recipients (FIGS. 10A-10F), consistent with Jmjd3 having an oncogenic role. These striking phenotypes supported our previous in vitro and in vivo findings and led to further exploration of the therapeutic potential of targeting JMJD3 activity in T-ALL.

Example 5

Pharmacological Targeting of T-ALL Through Specific Inhibition of the Demethylase Activity of JMJD3

Figure 12A:
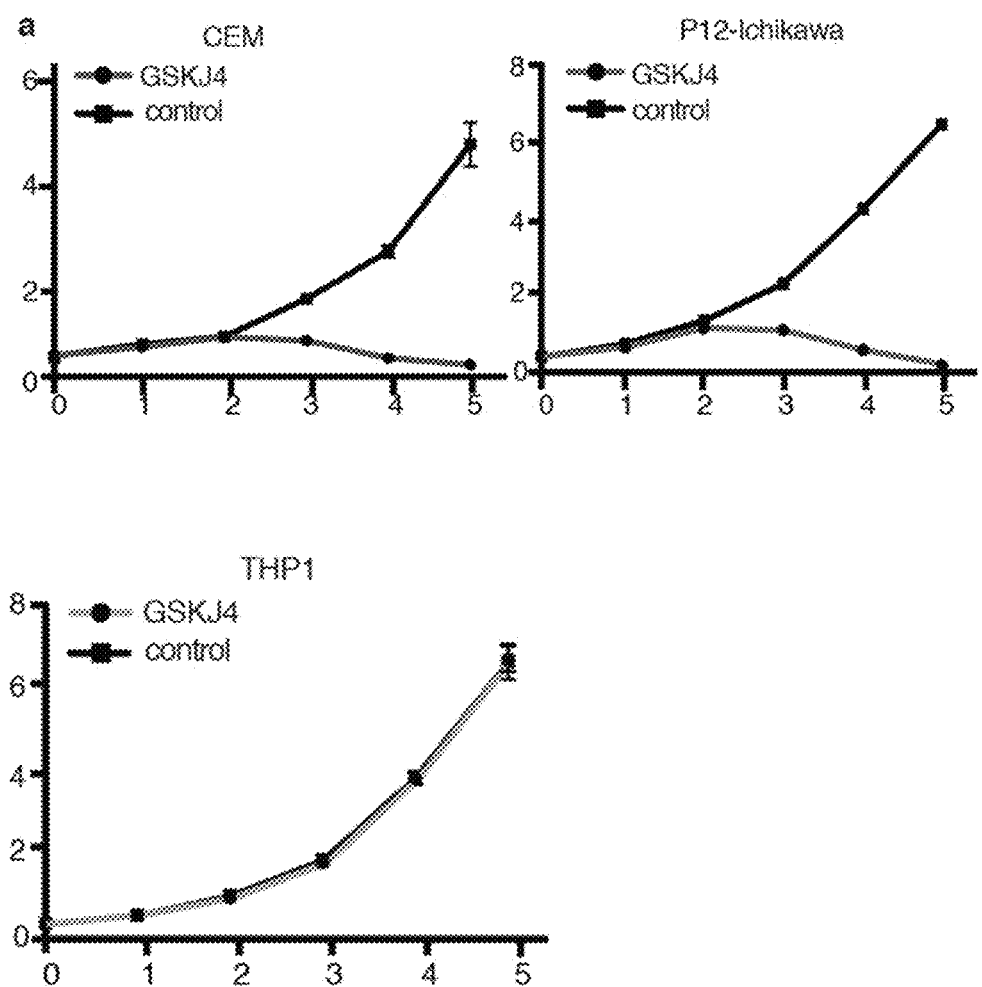
FIGS. 12A-12N show GSKJ4 inhibitor induces apoptosis and cell cycle arrest of T-ALL but not myeloid leukemia or physiological LSK cells.
Figures 12B, 12C, 12D:
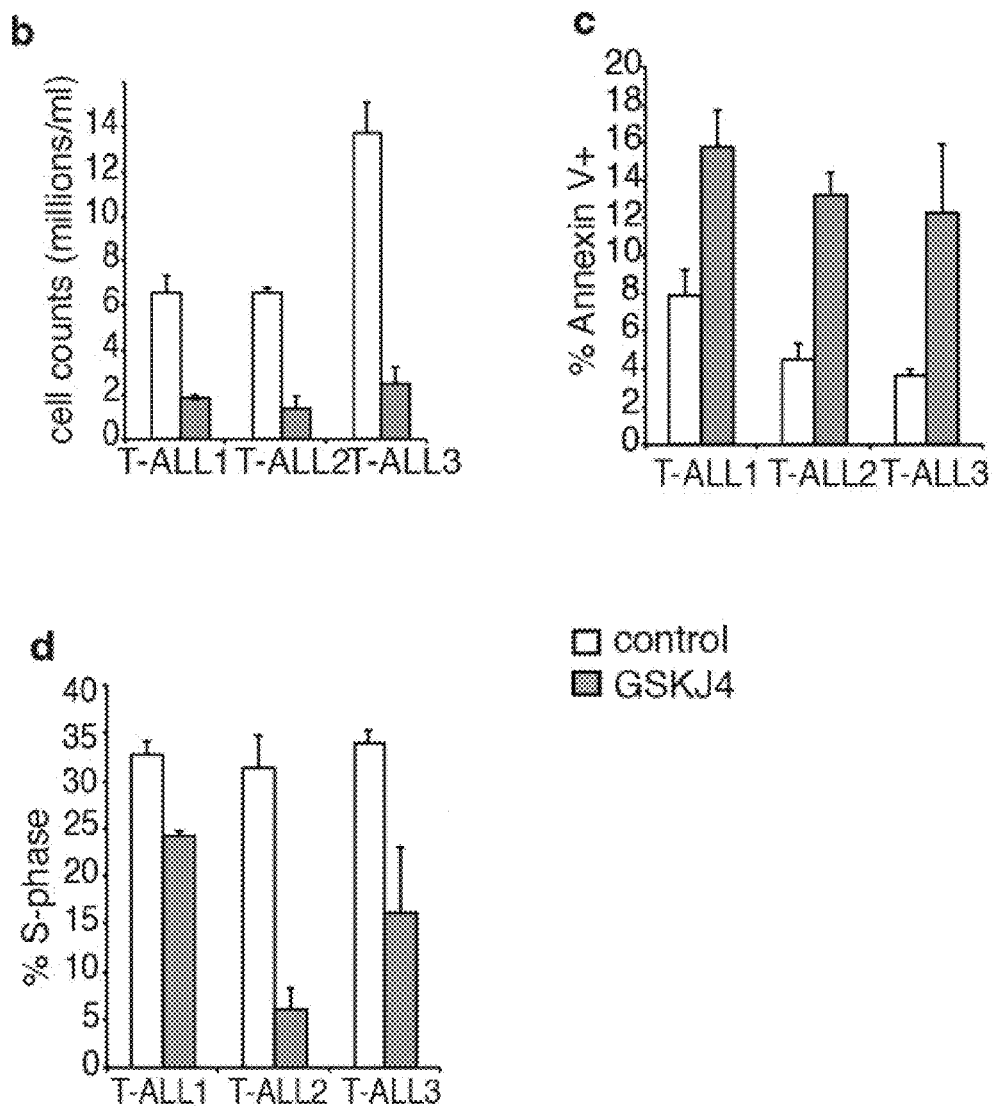
FIGS. 12B-12D shows the effects on cell growth (FIG. 12B), apoptosis (FIG. 12C) and the cell cycle (FIG. 12D) in three primary T-ALL lines. The average results from three representative studies are shown.
Figures 12E, 12F:
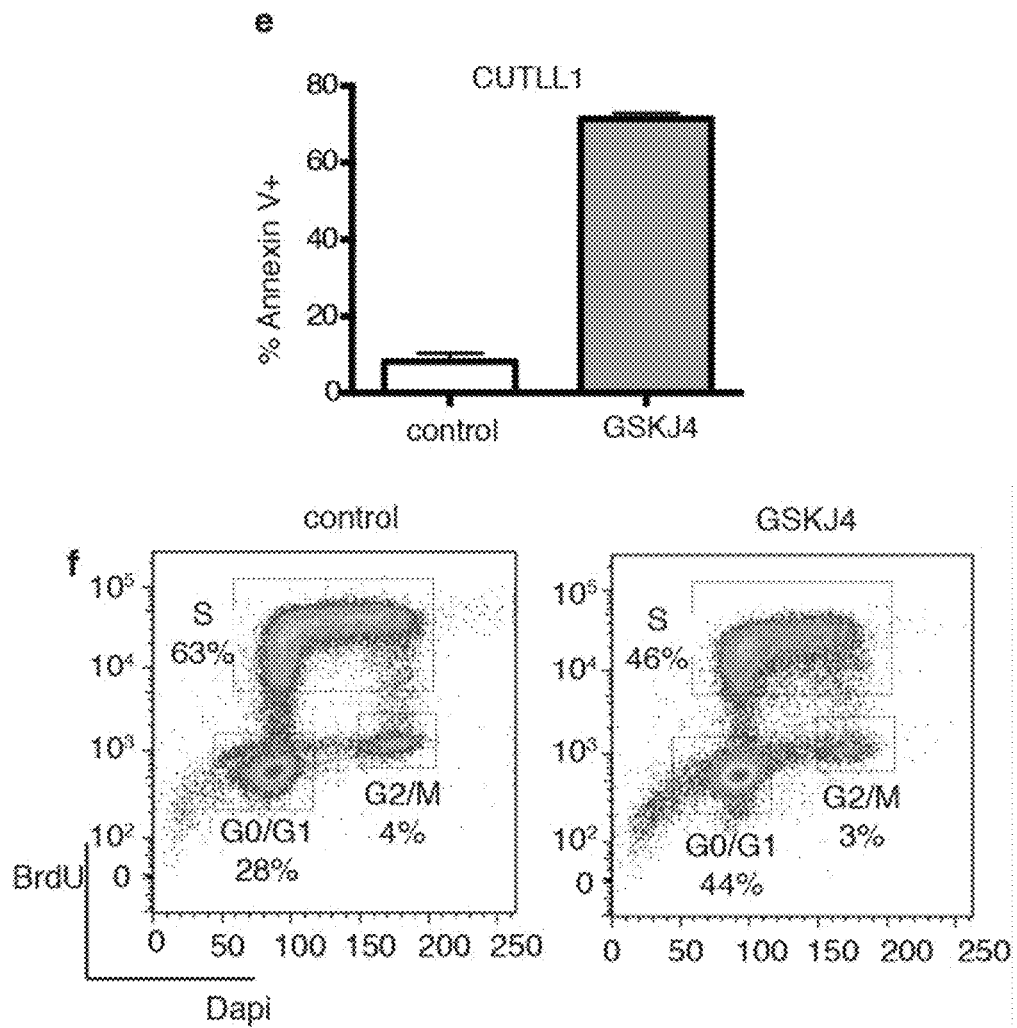
FIGS. 12E-12F show measurement of apoptosis (FIG. 12E, n=3) and cell cycle effects (FIG. 12F, representative study from three experiments) on CUTLL1 cells 72 hours post treatment with the inhibitor.
Figure 12G:
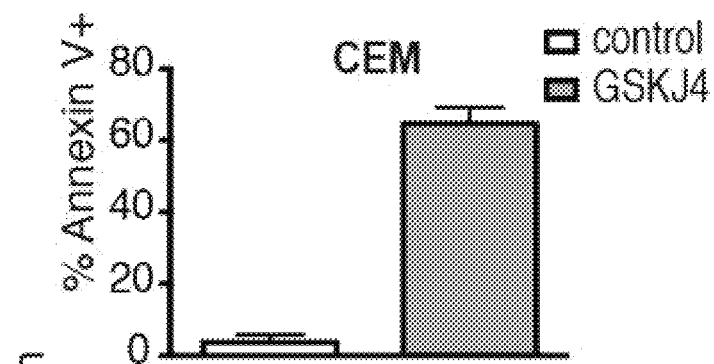
FIGS. 12G-12H show apoptosis assays using annexin V staining of CEM cells (FIG. 12G) after a period of 72 hours of treatment and measuring caspase 7/9 activity upon treatment of CUTLL1 T-ALL cells with GSKJ5 or GSKJ4 over a period of 24 hours (FIG. 12H).
Figure 12H:
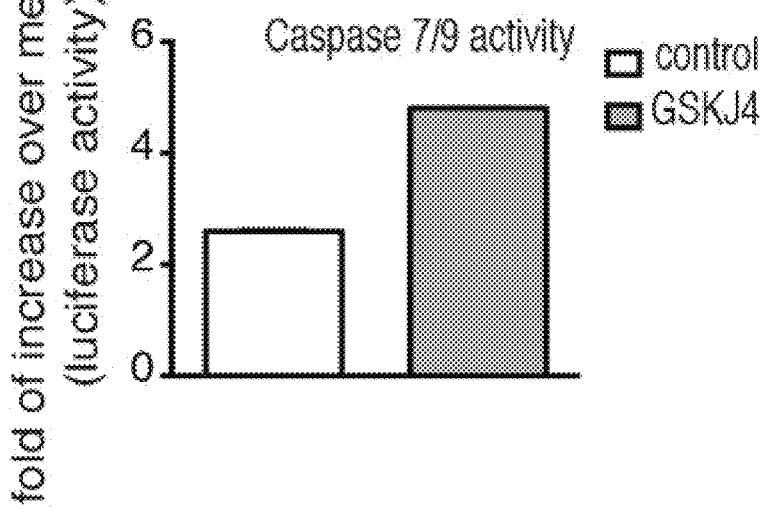
Figures 12I, 12J:
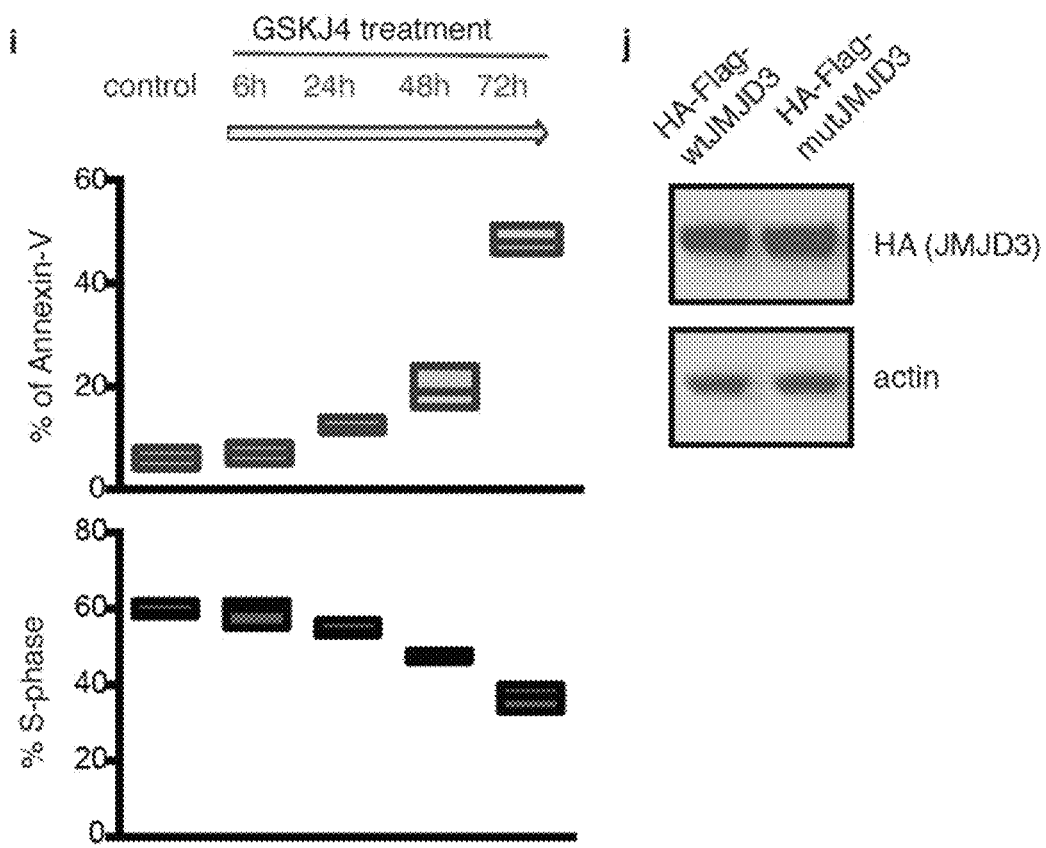
FIG. 12I shows time course studies of annexin V (top) and cell cycle analysis (bottom) of CUTLL1 cells over a period of 72 hours during GSKJ4 treatment according to the scheme on top of the figure.
FIG. 12J shows expression of the wild-type and catalytic mutant of JMJD3 in T-ALL (CEM) cells.
Figures 12K, 12L:
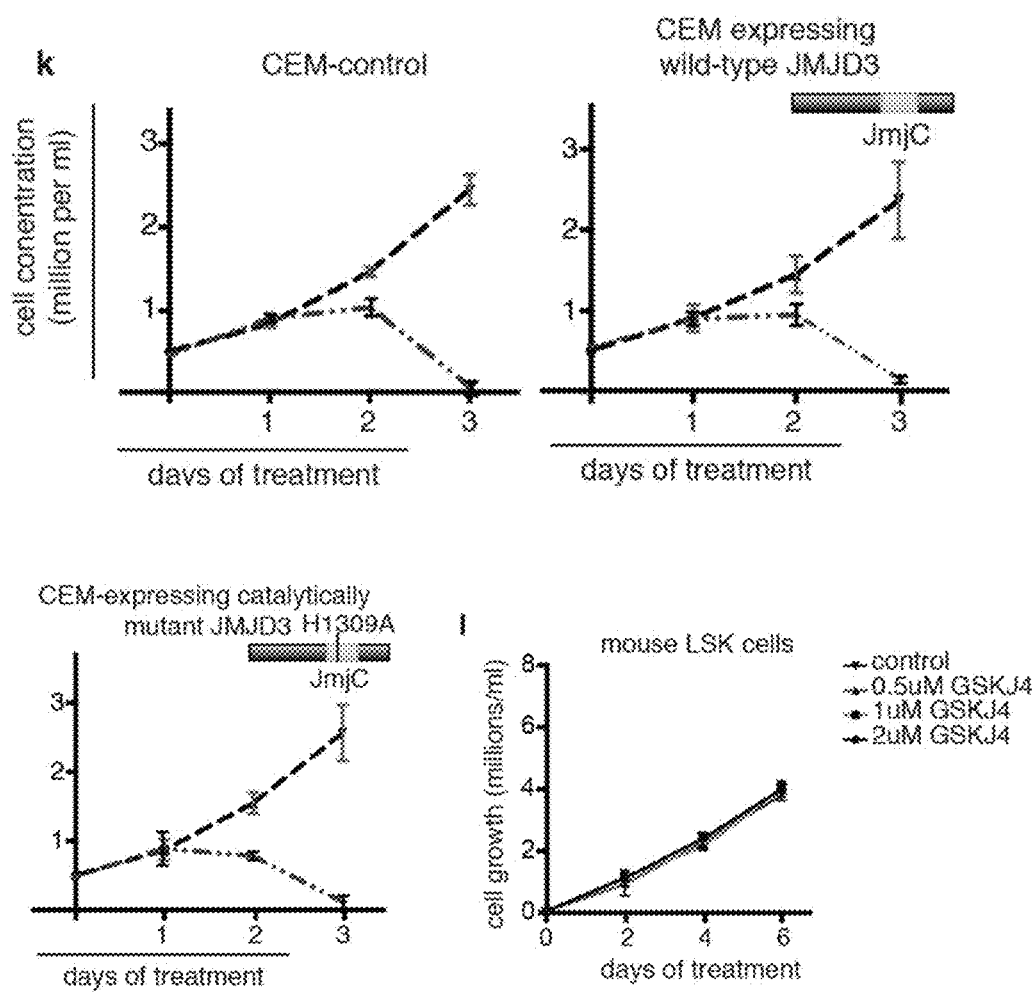
FIG. 12K shows cell growth analysis of T-ALL cells overexpressing wild-type JMJD3 or a catalytic mutant of JMJD3 upon GSKJ4 treatment over a period of 72 hours. Average results from three independent experiments are shown.
FIG. 12L shows cell growth of LSK cells upon treatment with the control (2 mM) and different concentrations of the inhibitor GSKJ4.
Figures 12M, 12N:
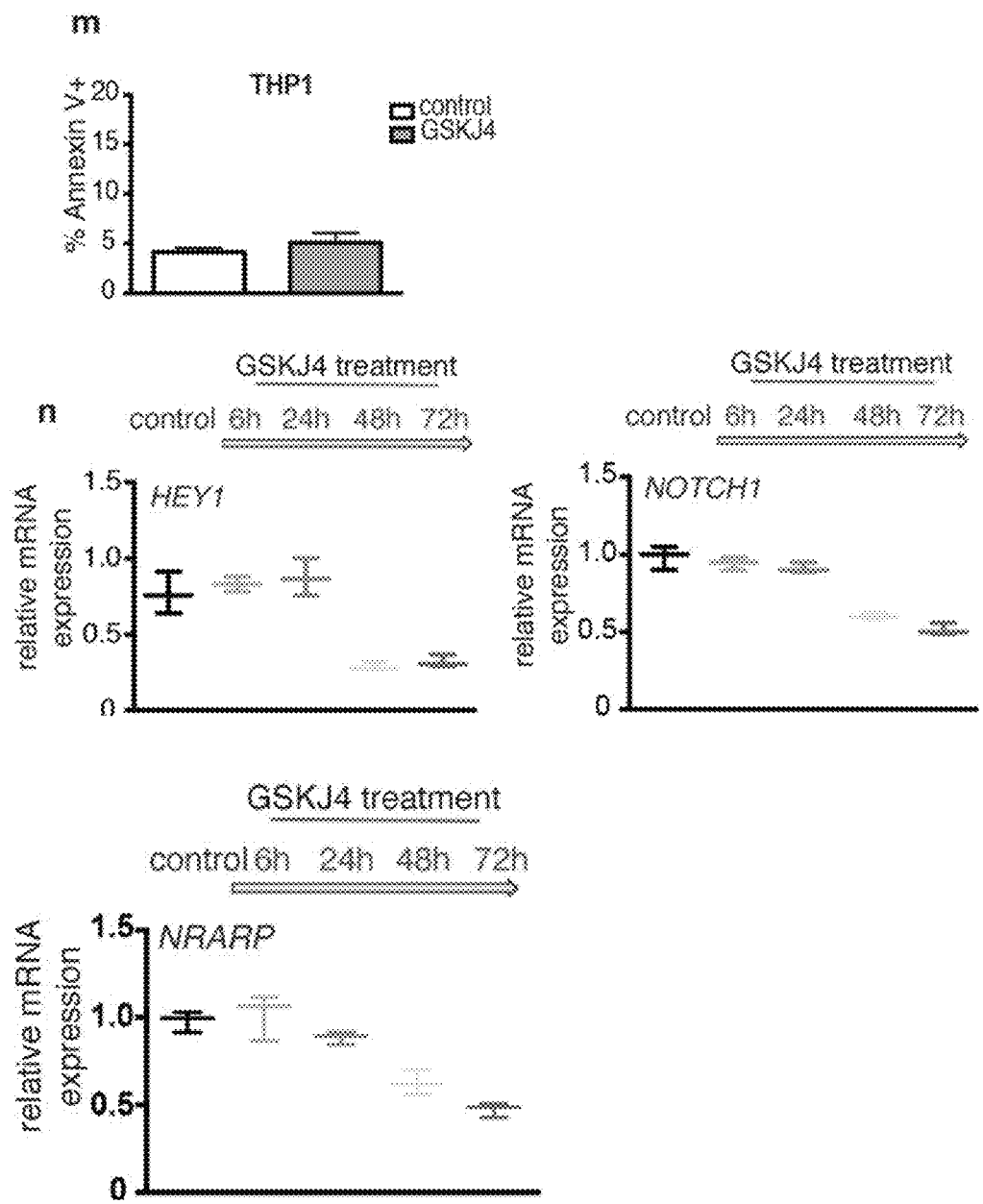
FIG. 12M shows Annexin V staining of THP-1 (AML) cells after a period of 72 hours of GSKJ4 or GSKJ5 (control) treatment at 2 mM concentration. The average results from three independent experiments are shown.
Figure 13A:
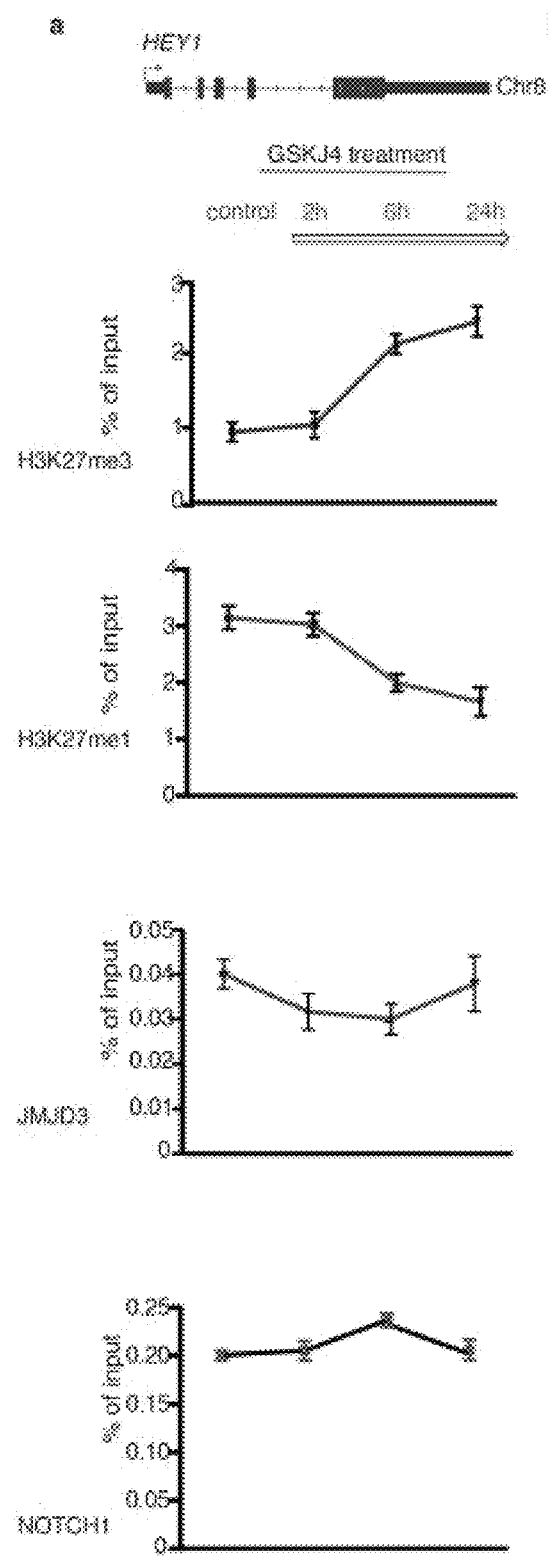
FIGS. 13A-13G show GSKJ4 treatment leads to increased H3K27me3 levels on NOTCH target genes through specific inhibition of JMJD3 activity.
Figure 13B:
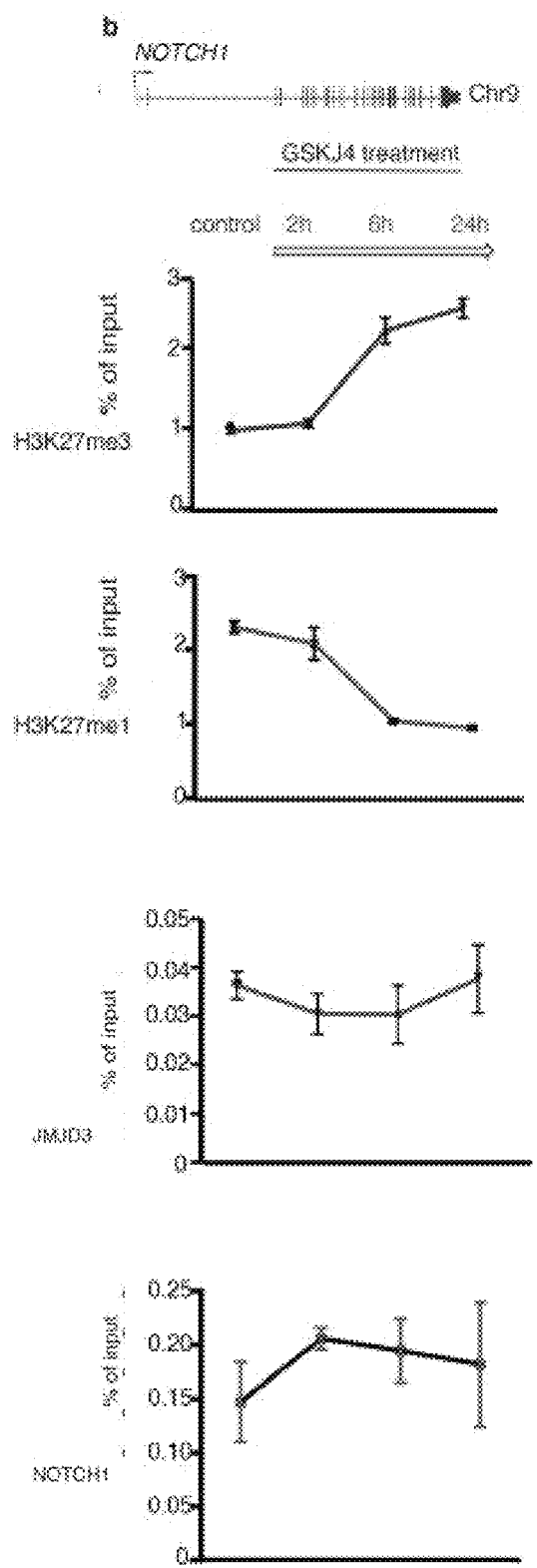
Figure 13C:
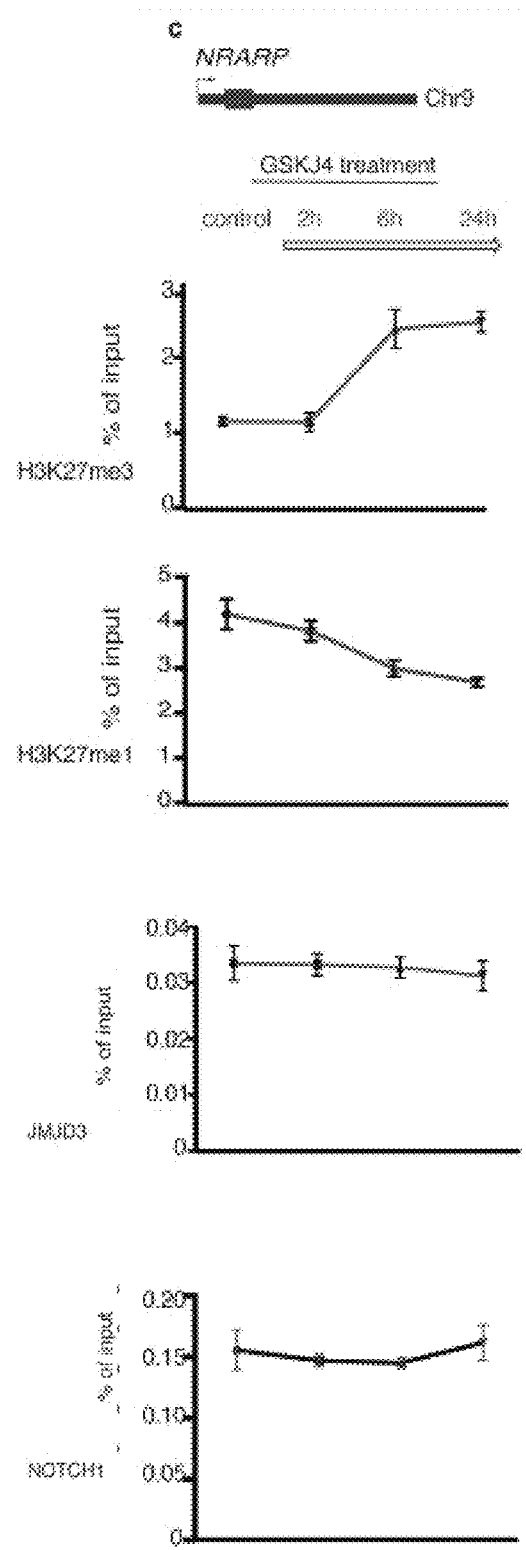
Figures 13D, 13E:
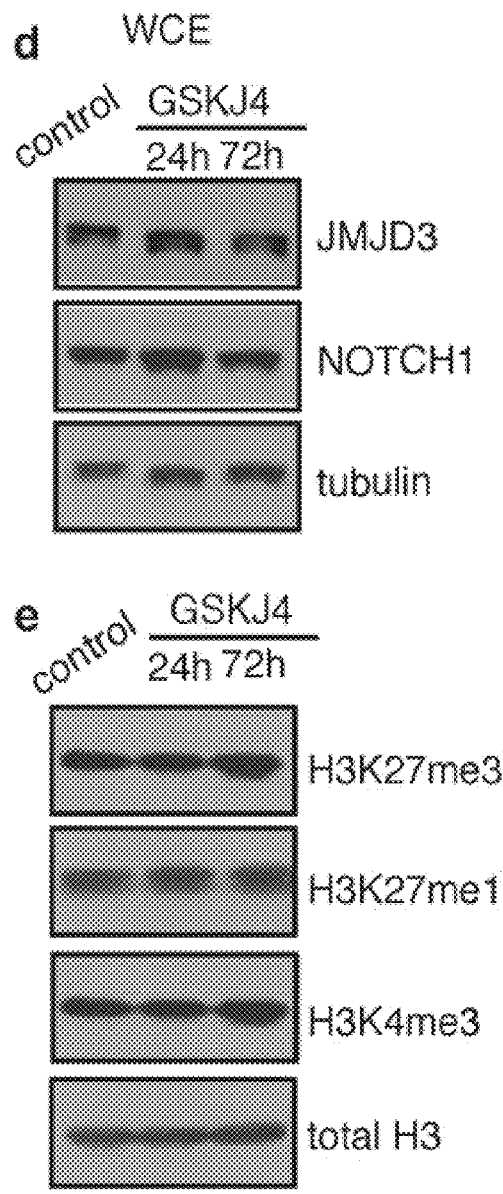

It was next tested whether the small molecule GSKJ4 (Kruidenier et al., "A Selective Jumonji H3K27 Demethylase Inhibitor Modulates the Proinflammatory Macrophage Response," Nature 488:404-408 (2012), which is hereby incorporated by reference in its entirety), which is directed against JMJD3 and UTX (half-maximum inhibitory concentration ($IC_{50}$) as determined by matrix-assisted laser desorption mass spectroscopy, JMJD3, 18 mM; UTX 56 mM; Kruidenier et al., "A Selective Jumonji H3K27 Demethylase Inhibitor Modulates the Proinflammatory Macrophage Response," Nature 488:404-408 (2012), which is hereby incorporated by reference in its entirety), affects maintenance of the disease. GSKJ4 was used at the $IC_{50}$ determined for T-ALL cells (2 mM) (FIG. 11A) to treat a panel of T-ALL cell lines. GSKJ4 significantly affected the growth of human T-ALL cell lines and primary human TALL cells (T-ALL1-3), leading to cell cycle arrest and increased apoptosis compared with control-inhibitor-treated cells (FIG. 11B and FIGS. 12A-12H). The first detectable changes started at 24 hours, and significantly altered phenotypes were observed at 48 hours and 72 hours (FIG. 12I). These GSKJ4 effects appear to be connected to the demethylase activity of JMJD3, as overexpression of catalytically inactive JMJD3 did not rescue the phenotype (FIGS. 12J-12K). The growth of myeloid leukaemia cells, stromal cells and haematopoietic progenitor cells (FIGS. 12L-12M) was unaffected by GSKJ4, demonstrating specificity of function. Mechanistically, gene expression changes were detected starting at 24 hours post-GSKJ4 treatment, and significant changes were noted at 48 hours and 72 hours (FIG. 12N) and were coupled to an increase in the H3K27me3 levels at repressed genes (FIGS. 13A-13C). The NOTCH1 and JMJD3 occupancy at specific NOTCH1 target genes that were tested, as well as the total cellular levels of NOTCH1 and JMJD3 and the chromatin H3K27me3 levels, did not significantly change over the treatment duration (FIGS. 13A-13E).

Figures 11A, 11B, 11C:
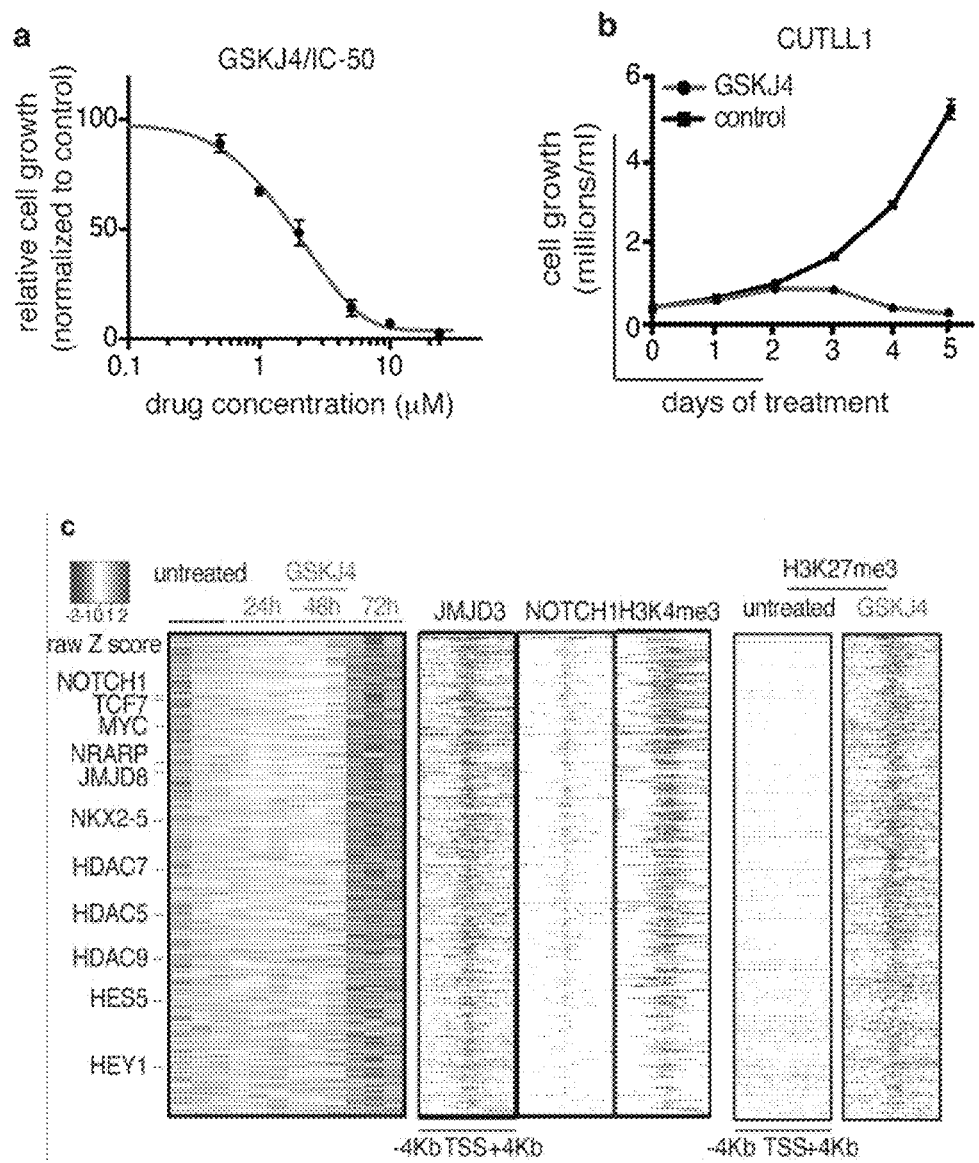
FIGS. 11A-11E show pharmacological targeting of T-ALL through specific inhibition of the demethylase activity of JMJD3.
Figures 11D, 11E:
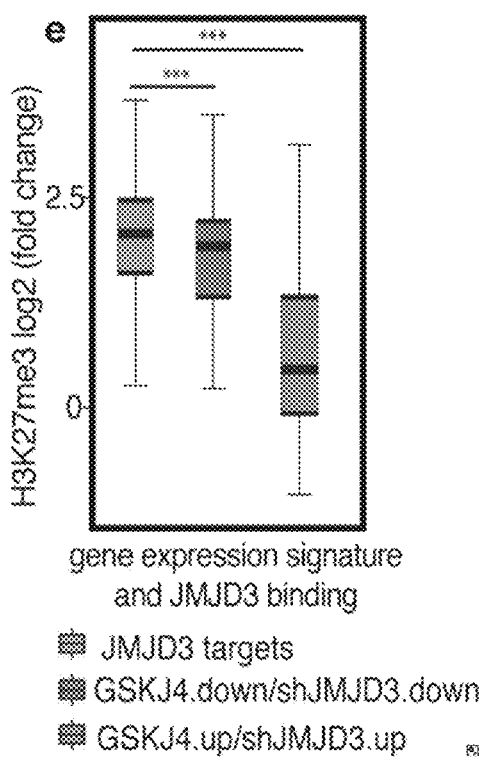

Genome-wide studies identified 486 downregulated genes after 72 hours of treatment of human T-ALL cells (CUTLL1)

with GSKJ4 (FIG. 11C). There was a significant overlap between the shJMJD3 and GSKJ4 signatures for both down-regulated genes (P=4.88×10$^{-44}$; FIG. 11D and Table 3) and upregulated genes (P=2.57×10$^{-20}$).

TABLE 3

Overlap between gene expression changes in knock-downs, GSKJ4, and Utx knockout genotype.

| GENES | LIST-A | LIST-B | INTERSECTION | EXPECTED | P-VALUE | LIST-A | LIST-B |
|---|---|---|---|---|---|---|---|
| 20414 | 749 | 3682 | 373 | 135.1 | 6.53E−91 | shJMJD3_specific.down | CEM_shJMJD3_specific.down |
| 20414 | 297 | 1636 | 62 | 23.8 | 2.01E−12 | shJMJD3_specific.up | CEM_shJMJD3_specific.up |
| 20414 | 749 | 486 | 97 | 17.8 | 4.88E−44 | shJMJD3_specific.down | GSKJ4_vs_untreated.down |
| 20414 | 297 | 486 | 17 | 7.1 | 8.18E−04 | shJMJD3_specific.up | GSKJ4_vs_untreated.down |
| 20414 | 749 | 1751 | 74 | 64.2 | 1.11E−01 | shJMJD3_specific.down | GSKJ4_vs_untreated.up |
| 20414 | 297 | 1751 | 79 | 25.5 | 2.57E−20 | shJMJD3_specific.up | GSKJ4_vs_untreated.up |
| 20414 | 46 | 486 | 7 | 1.1 | 9.95E−05 | shUTX_specific.down | GSKJ4_vs_untreated.down |
| 20414 | 189 | 486 | 24 | 4.5 | 2.51E−11 | shUTX_specific.up | GSKJ4_vs_untreated.down |
| 20414 | 46 | 1751 | 11 | 3.9 | 1.43E−03 | shUTX_specific.down | GSKJ4_vs_untreated.up |
| 20414 | 189 | 1751 | 29 | 16.2 | 1.54E−03 | shUTX_specific.up | GSKJ4_vs_untreated.up |
| 20414 | 1472 | 486 | 48 | 35 | 1.66E−02 | UTXKO_down | GSKJ4.down |
| 20414 | 1789 | 486 | 83 | 42.6 | 2.49E−09 | UTXKO_up | GSKJ4.down |
| 20414 | 1472 | 1751 | 167 | 126.3 | 8.95E−05 | UTXKO_down | GSKJ4.up |
| 20414 | 1789 | 1751 | 210 | 153.5 | 1.02E−06 | UTXKO_up | GSKJ4.up |

Figure 13F:
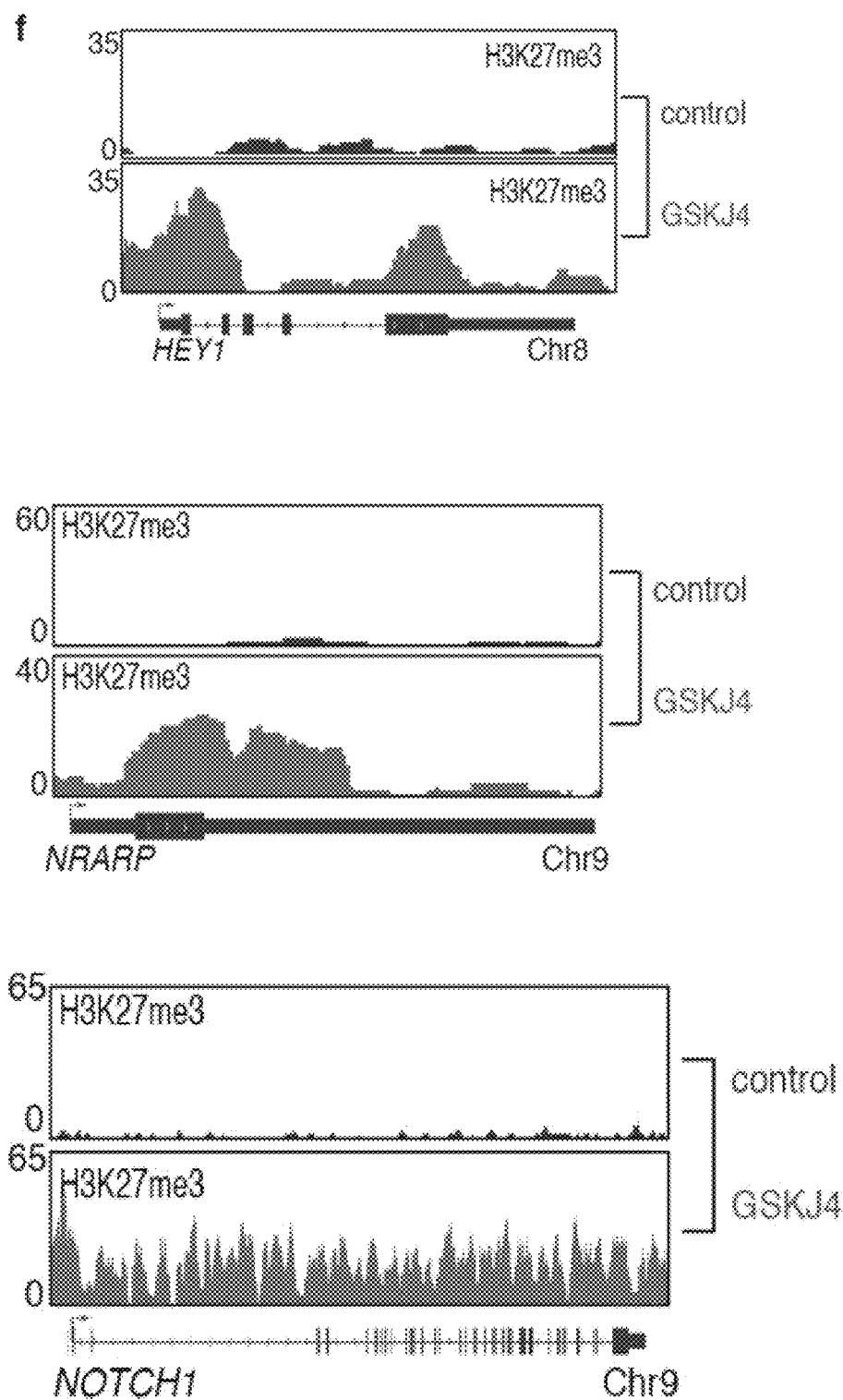
Figure 13G:
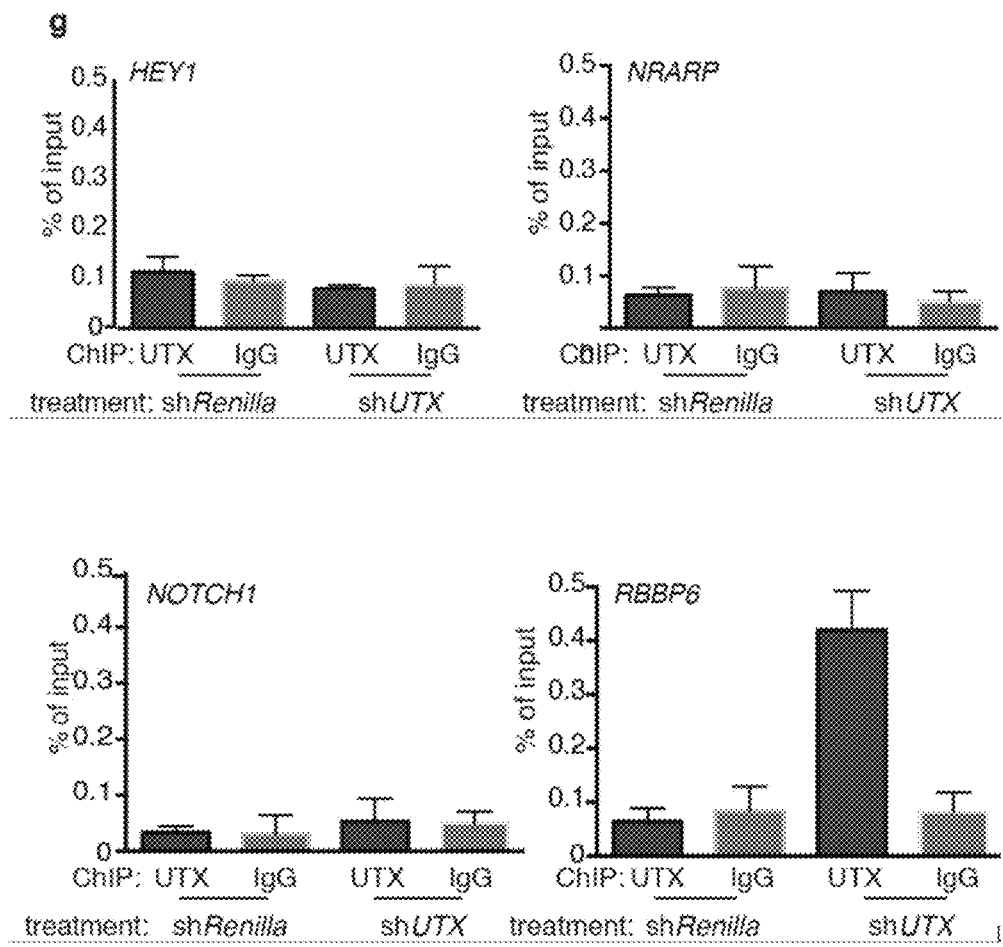

By contrast, the shUTX-upregulated gene signature significantly overlapped with the GSKJ4-downregulated gene signature. Furthermore, there was a significant overlap between genes upregulated in Utx knockout blasts and downregulated by GSKJ4 treatment (P=2.49×10$^{-9}$; FIG. 8E and FIG. 11D and Table 3), suggesting again that UTX and JMJD3 play opposing roles in T-ALL. Genome-wide study of H3K27me3 localization demonstrated that the GSKJ4-downregulated genes experienced gain of H3K27me3 upon GSKJ4 treatment and were marked by the presence of H3K4me3, NOTCH1 and JMJD3 at their promoters (FIG. 11C and FIG. 2J). Well-characterized NOTCH1 and JMDJ3 targets are highlighted as representative examples of the GSKJ4-downregulated/shJMJD3-downregulated signature and show a significant gain in H3K27me3 upon GSKJ4 treatment (FIG. 11E and FIG. 13F). UTX was not involved in the regulation of the oncogenic NOTCH1 targets, as revealed by ChIP studies (FIG. 13G).

Discussion of Examples 1-5

Figures 14A, 14B:
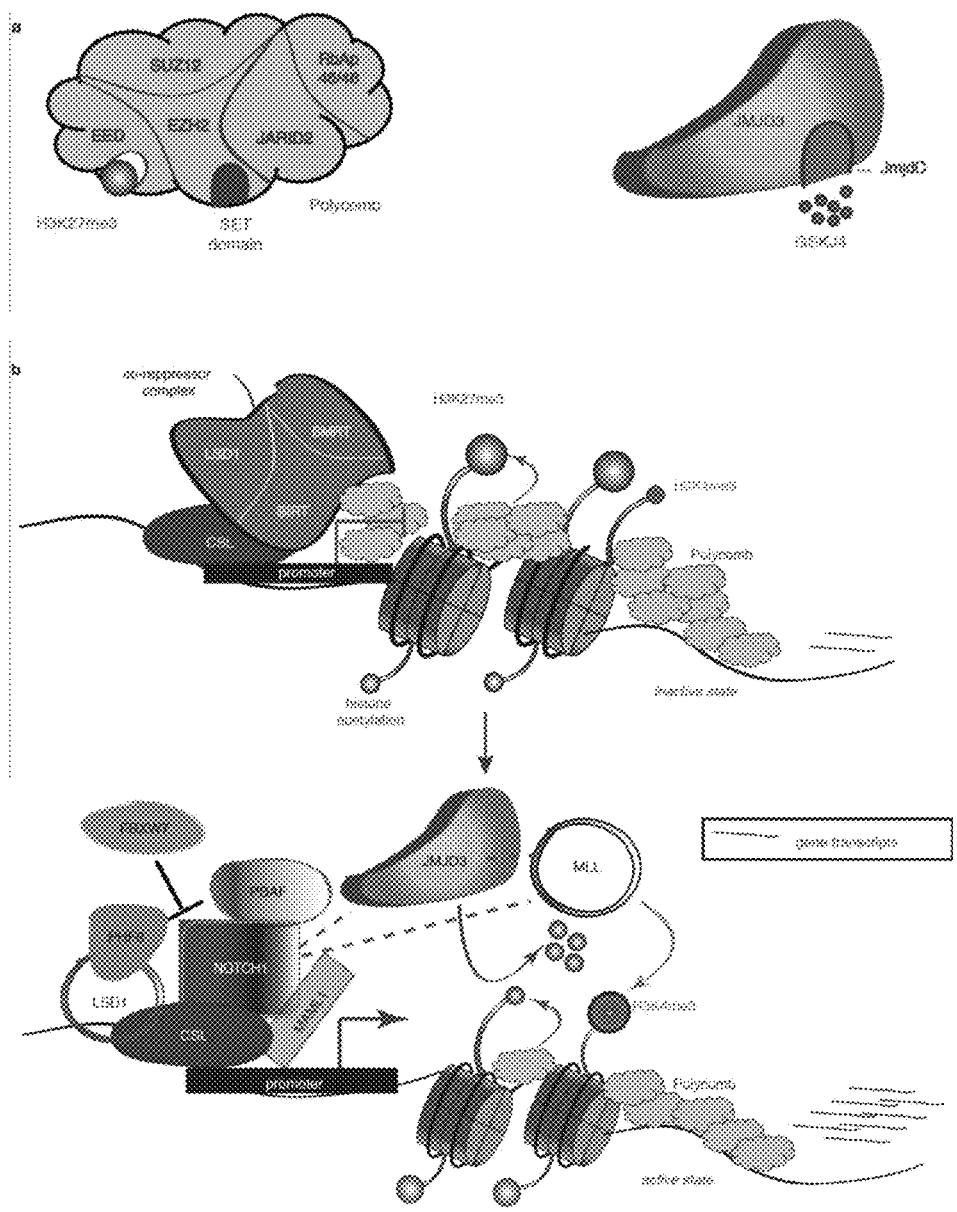
FIGS. 14A-14B show JMJD3 as a pivotal factor in NOTCH1-mediated oncogenic activation in T-cell leukemia.

Acute lymphoblastic leukemia consists of a panel of aggressive hematopoietic malignancies characterized by an array of mutations frequently affecting epigenetic modulators. Currently, there are no targeted therapies available for treatment of this disease, leaving chemotherapy and irradiation as the only available strategies, both exhibiting severe side effects and toxicity. It is proposed here the targeting of JMJD3 as a novel therapy option for pediatric and adult T-ALL. This proposal is based on recent studies (Zhang et al., "The Genetic Basis of Early T-Cell Precursor Acute Lymphoblastic Leukaemia," *Nature* 481:157-163 (2012); Ntziachristos et al., "Genetic Inactivation of the Polycomb Repressive Complex 2 in T Cell Acute Lymphoblastic Leukemia," *Nature Med.* 18:298-301 (2012); Simon et al., "A Key Role for EZH2 and Associated Genes in Mouse and Human Adult T-Cell Acute Leukemia," *Genes Dev.* 26:651-656 (2012), which are hereby incorporated by reference in their entirety) that demonstrate that the repressive chromatin mark trimethylation of lysine 27 on histone H3 (H3K27me3) plays a key role in T-ALL, through interplay with oncogenic NOTCH1. Mechanistically, it has been previously shown that the PRC2 complex antagonizes the NOTCH1 oncogenic action (Ntziachristos et al., "Genetic Inactivation of the Polycomb Repressive Complex 2 in T Cell Acute Lymphoblastic Leukemia," *Nature Med.* 18:298-301 (2012), which is hereby incorporated by reference in its entirety). As NOTCH1 does not exert demethylase activity itself, the exact mechanism through which NOTCH1 leads to H3K27me3 depletion from its target loci was delineated. It is demonstrated here that NOTCH1-mediated JMJD3 recruitment on promoters of key T-ALL gene regulators is at least in part this mechanism (FIG. 14).

Despite the fact that tumor suppressor roles were attributed to JMJD3 in the past (Agger et al., "The H3K27me3 Demethylase JMJD3 Contributes to the Activation of the INK4A ARF Locus in Response to Oncogene- and Stress-Induced Senescence," *Genes Dev.* 23:1171-1176 (2009); Barradas et al., "Histone Demethylase JMJD3 Contributes to Epigenetic Control of INK4a/ARF by Oncogenic RAS," *Genes Dev.* 23:1177-1182 (2009); Ene et al., "Histone Demethylase Jumonji D3 (JMJD3) as a Tumor Suppressor by Regulating p53 Protein Nuclear Stabilization," *PloS One* 7:e51407 (2012), which are hereby incorporated by reference in their entirety), mainly because of the role in oncogene-induced activation of the INK4A/ARF (CDKN2A) locus followed by senescence, it has been shown that this does not apply in T-ALL, where INK4A/ARF is frequently inactivated. The fact that JMJD3, in contrast to UTX, is prone to activation through specific stimuli, renders it an ideal partner and modulator of oncogenic pathways. As in the case of inflammation, T-ALL-specific JMJD3 expression is controlled through NF-κB activation, leading to an intriguing feedback loop between NOTCH1 and NFκB pathways. Indeed, this study provides a link between these two major pathways through a specific epigenetic modulator and underlines molecular similarities between inflammation and cancer in cells of hematopoietic origin.

It is known that in the absence of NOTCH1, RBPJk interacts with co-repressor complexes (including the SMRT complex and histone deacetylases). Part of the repressive activity in these loci is filtered through the activity of PRC2 complex, which leads to high H3K27me3 levels. It is proposed that NOTCH1 recruitment leads to PRC2 eviction due to active demethylation of lysine 27 on histone 3 through the catalytic activity of JMJD3 and the recruitment of JMJD3 to target promoters leading to lower H3K27me3 levels. On the other hand, the reported increased levels of the activating H3K4me3 mark on a large fraction of NOTCH1 targets (Ntziachristos et al., "Genetic Inactivation of the Polycomb Repressive Complex 2 in T Cell Acute Lymphoblastic Leukemia," *Nature Med.* 18:298-301 (2012); Liefke et al., "Histone Demethylase KDM5A is an Integral Part of the Core Notch-RBP-J Repressor Complex," *Genes Dev.* 24:590-601 (2010); Wang et al., "NOTCH1-RBPJ Complexes Drive Target Gene Expression Through Dynamic Interactions With Superenhancers," *Proc. Natl. Acad. Sci. USA* 111:705-710 (2014); Wang et al., "Genome-Wide Analysis Reveals Conserved and Divergent Features of Notch1/RBPJ Binding in Human and Murine T-Lymphoblastic Leukemia Cells," *Proc. Natl. Acad. Sci. USA* 108: 14908-14913 (2011), which are hereby incorporated by reference in their entirety) (FIG. 11) can be explained by the fact that NOTCH1 has the ability to recruit MLL complexes (FIG. 3 and FIG. 14). The findings herein show that both NOTCH1 and JMJD3 interact with WDR5 (FIG. 3), providing a potential link between the fine-tuning of these two histone marks.

The GSKJ4 epigenetic inhibitor, targeting H3K27 demethylase activity, was previously tested in conditions of inflammatory stress (Kruidenier et al., "A Selective Jumonji H3K27 Demethylase Inhibitor Modulates the Proinflammatory Macrophage Response," *Nature* 488:404-408 (2012), which is hereby incorporated by reference in its entirety). It is shown herein for the first time anti-tumorigenic activities and significant specificity towards NOTCH1-transformed T-ALL. It is proposed that GSKJ4 inhibits JMJD3 demethylase activity (see FIG. 14), targeting T-ALL growth without affecting other cell types. Obviously, the possibility that GSKJ4 could potentially affect other important epigenetic modulators or signaling pathways cannot be excluded (Natoli et al., "The Future Therapeutic Potential of Histone Demethylases: A Critical Analysis," *Curr. Op/n. Drug Discov. Devel.* 12:607-615 (2009), which is hereby incorporated by reference in its entirety). Nevertheless it is believed that the main action of this inhibitor passes through the inhibition of JMJD3 activity, as knockdown of members of other Jumonji family-potential candidates did not affect viability of T-ALL cells in shRNA screen. It is proposed that such inhibitors be used either as single drugs or in combination to standard chemotherapy. This notion is further supported by the fact that GSKJ4 is active at achievable concentrations in clinical settings, it is more active against JMJD3 and it affects specifically acute lymphoblastic leukemia but not healthy cells or other types of leukemia, underscoring the specificity of the compound.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating T-cell acute lymphoblastic leukemia in a subject, said method comprising:
   selecting a subject having T-cell acute lymphoblastic leukemia and
   administering, to the selected subject, an inhibitor of jumonji D3 (JMJD3) demethylase activity at a dosage effective to treat the T cell acute lymphoblastic leukemia in the subject.

2. The method of claim 1, wherein the selected subject has an activating NOTCH1 mutation.

3. The method according to claim 1, wherein the JMJD3 inhibitor is ethyl 3-((6-(4,5-dihydro-1H-benzo[d]azepin-3 (2H)-yl)-2-(pyridin-2-yl)pyrimidin-4-yl)amino)propanoate (GSK-J4) or a derivative thereof.

4. The method according to claim 1, wherein the JMJD3 inhibitor is a JMJD3 antisense RNA, shRNA, or siRNA oligonucleotide.

5. The method according to claim 1 further comprising: administering a chemotherapeutic agent to the subject in combination with said JMJD3 inhibitor.

6. The method according to claim 5, wherein the chemotherapeutic agent is selected from the group consisting of cytarabine, vincristine, prednisone, doxorubicin, daunorubicin, PEG asparaginase, methotrexate, cyclophosphamide, L-asparaginase, etoposide, and leucovorin.

7. The method according to claim 1, wherein said administering is repeated periodically.

8. The method according to claim 1, wherein T-cell acute lymphoblastic leukemia is adult T-cell acute lymphoblastic leukemia.

9. The method according to claim 1, wherein T-cell acute lymphoblastic leukemia is pediatric T-cell acute lymphoblastic leukemia.

10. A method of inhibiting T-cell acute lymphoblastic leukemia cell proliferation and/or survival, said method comprising:

administering to a population of T-cell acute lymphoblastic leukemia cells an inhibitor of JMJD3 at a dosage effective to inhibit the T-cell acute lymphoblastic leukemia cell proliferation and/or survival.

11. The method according to claim 10, wherein the JMJD3 inhibitor is ethyl 3-((6-(4,5-dihydro-1H-benzo[d]azepin-3 (2H)-yl)-2-(pyridin-2-yl)pyrimidin-4-yl)amino)propanoate (GSK-J4) or a derivative thereof.

12. The method according to claim 10, wherein the JMJD3 inhibitor is a JMJD3 antisense RNA, shRNA, or siRNA oligonucleotide.

13. The method according to claim 10, wherein said administering is carried out in vivo.

14. The method according to claim 10, wherein said administering is repeated periodically.

* * * * *